US007906278B2

(12) United States Patent
Liew et al.

(10) Patent No.: US 7,906,278 B2
(45) Date of Patent: Mar. 15, 2011

(54) DIAGNOSIS OF OSTEOARTHRITIS BY DETERMINATION OF ASPORIN RNA LEVELS

(75) Inventors: Choong-Chin Liew, Toronto (CA); Wayne Marshall, Toronto (CA); Hongwei Zhang, Toronto (CA)

(73) Assignee: Chondrogene, Inc. (CA)

( * ) Notice: Subject to any disclaimer, the term of this patent is extended or adjusted under 35 U.S.C. 154(b) by 390 days.

(21) Appl. No.: 10/242,535

(22) Filed: Sep. 12, 2002

(65) Prior Publication Data

US 2004/0013663 A1    Jan. 22, 2004

Related U.S. Application Data

(63) Continuation-in-part of application No. 10/085,783, filed on Feb. 28, 2002, now Pat. No. 7,432,049.

(60) Provisional application No. 60/305,340, filed on Jul. 13, 2001, provisional application No. 60/275,017, filed on Mar. 12, 2001, provisional application No. 60/271,955, filed on Feb. 28, 2001.

(51) Int. Cl.
*C12Q 1/68* (2006.01)
*C07H 21/04* (2006.01)

(52) U.S. Cl. ........ 435/6; 536/23.5; 536/24.31; 536/25.4

(58) Field of Classification Search ........................ None
See application file for complete search history.

(56) References Cited

U.S. PATENT DOCUMENTS

2001/0051344 A1* 12/2001 Shalon et al. .................... 435/6

FOREIGN PATENT DOCUMENTS

| EP | 0 705 842 A | 4/1996 |
|---|---|---|
| WO | WO 99 32610 A | 7/1999 |
| WO | WO02085285 | 10/2002 |

OTHER PUBLICATIONS

Gebhard et al. Quantification of expression levels of cellular differentiation markers does not support a general shift in the cellular phenotype of osteoarthritic chondrocytes. Journal of Orthopaedic Research, vol. 21, pp. 96-101, 2003.*

Kroese et al. Genetic tests and their evaluation: can we answer the key questions? Genet Med. 2004 vol. 6, No. 6, pp. 475-80, Nov.-Dec. 2004.*
Lorenzo et al (Identification and characterization of asporin-a novel member of the leucine rich repeat family closely related to decorin and biglycan. The Journal of Biological Chemistry, Manuscript M010932200, pp. 1-47, Jan. 10, 2001.*
McAlinden et al. Age-related changes in the synthesis and mRNA expression of decorin and aggrecan in human meniscus and articular cartilage. OsteoArthritis and Cartilage, vol. 9, pp. 33-41, Jan. 2001.*
Kumar, S. et al., (2001), "Identification and initial characterization of 5000 expressed sequenced tags (ESTs) each from adult human normal and osteoarthritic cartilage cDNA libraries," *Osteoarthritis and Cartilage*, 9: 641-653.
Database EMBL Online!, Van Asseldonk et al., *Homo Sapiens Alpha Gene Sequence*, Database accession No. AF203815, XP002243659, Abstract, Jun. 6, 2003.
Andrews J. et al., *Gene Discovery Using Computational and Microarray Analysis of Transcription in the Drosophila Melanogaster Testis. Genome Research*, vol. 10, Dec. 2000, pp. 2030-2043.
Patel I.R. et al., *TNF-Alpha Convertase Enzyme From Human Arthritis—Affected Cartilage: Isolation of cDNA by Differential Display, Expression of the Active enzyme, and Regulation of TNF—Alpha*, The Journal of Immunology, 1998, 160: pp. 4570-4579.
Shukunami et al., *Expression of Cartilage-Specific Functional Matrix Chondromodulin-I mRNA in Rabbit Growth Plate Chondrocytes and Its Responsiveness to Growth Stimuli in Vitro*, Biochemical and Biophysical Research Communication, vol. 249, No. 3, Aug. 28, 1998, pp. 885-890.
Alizadeh A. et al., *The Lymphochip: A Specialized CDNA Microarray for the Genomic-Scale Analysis of Gene Expression in Normal and Malignant Lymphocytes*, Cold Spring Harbor Symposia on Quantitative Biology, vol. 64, No. 1, 1999, pp. 71-78.
Duggan D. J. et al., *Expression Profiling Using cDNA Microarrays*, Nature Genetics, vol. 21, , Jan. 1999, pp. 10-14.

* cited by examiner

*Primary Examiner* — Jennifer Dunston
(74) *Attorney, Agent, or Firm* — Edwards Angell Palmer & Dodge LLP; Kathleen Williams; Amy DeCloux

(57) ABSTRACT

The invention relates to the identification and selection of sequences which demonstrate particular advantage in identifying individuals having osteoarthritis (OA). The invention also provides a selection of sequences particularly useful in diagnosing the degree of advancement of osteoarthritis of an individual and in the identification of novel therapeutic targets for OA. The invention further provides for the use of these sequences as a tool to diagnose disease progression and to monitor the efficacy of therapeutic regimens.

4 Claims, 9 Drawing Sheets

DIAGNOSIS OF OSTEOARTHRITIS BY DETERMINATION OF ASPORIN RNA LEVELS

RELATED APPLICATIONS

The present application is a continuation-in-part of U.S. patent application with Ser. No. 10/085,783, filed Feb. 28, 2002, now U.S. Pat. No. 7,432,049, which claims priority to U.S. Provisional Application Ser. No. 60/305,340; filed Jul. 13, 2001, U.S. Provisional Application Ser. No. 60/275,017, filed Mar. 12, 2001, and U.S. Provisional Application Ser. No. 60/271,955, filed Feb. 28, 2001, each of which is incorporated herein by reference in its entirety.

This application includes a compact disc in duplicate (2 compact discs: Sequence Listing—Copy 1 Replacement Mar. 27, 2010 and Sequence Listing—Copy 2 Replacement Mar. 27, 2010), which are hereby incorporated by reference in their entirety. Each compact disc is identical and contains the following file: Seq listing Mar2010.TXT.

| Disc | DESCRIPTION | SIZE | CREATED | Text File Name | Machine Format and Operating System |
|---|---|---|---|---|---|
| Copy 1 Replacement Mar. 27, 2010 | Sequence Listing | 28.8MB | Mar. 27, 2010 | Seq listing Mar2010.TXT | IBM PC MS-Windows |
| Copy 2 Replacement Mar. 27, 2010 | Sequence Listing | 28.8MB | Mar. 27, 2010 | Seq listing Mar2010.TXT | IBM PC MS-Windows |

This application includes a compact disc in duplicate (2 compact discs: Table 26—Copy 1 and Table 26—Copy 2), which are hereby incorporated by reference in their entirety. Each compact disc is identical and contains the following file: Table26.TXT.

LENGTHY TABLES

The patent contains a lengthy table section. A copy of the table is available in electronic form from the USPTO web site (http://seqdata.uspto.gov/?pageRequest=docDetail&DocID=US07906278B2). An electronic copy of the table will also be available from the USPTO upon request and payment of the fee set forth in 37 CFR 1.19(b)(3).

| Disc | DESCRIPTION | SIZE | CREATED | Text File Name | Machine Format and Operating System |
|---|---|---|---|---|---|
| Copy 1 Replacement Mar. 10, 2009 | Table 26 | 2.67MB | Mar. 10, 2009 | Table26.TXT | IBM PC MS-Windows |
| Copy 2 Replacement Mar. 10, 2009 | Table 26 | 2.67MB | Mar. 10, 2009 | Table26.TXT | IBM PC MS-Windows |

Disc DESCRIPTION SIZE CREATED Text File Name Machine Format and Operating System Copy 1 Replacement IBM PC Mar. 10, 2009 Table 26 2.67 MB Mar. 10, 2009 Table26.TXT MS-Windows Copy 2 Replacement IBM PC Mar. 10, 2009 Table 26 2.67 MB Mar. 10, 2009 Table26.TXT MS-Windows

FIELD OF THE INVENTION

The invention relates to the identification and selection of sequences which demonstrate particular advantage in identifying individuals having osteoarthritis (OA). The invention also provides a selection of sequences particularly useful in diagnosing the degree of advancement of osteoarthritis of an individual and in the identification of novel therapeutic targets for OA. The invention further provides for the use of these sequences as a tool to diagnose disease progression and to monitor the efficacy of therapeutic regimens.

BACKGROUND OF THE INVENTION

Osteoarthritis (OA) is a chronic disease in which the articular cartilage that lies on the ends of bones that forms the articulating surface of the joints gradually degenerates over time. There are many factors that are believed to predispose a patient to osteoarthritis including genetic susceptibility, obesity, accidental or athletic trauma, surgery, drugs and heavy physical demands. Osteoarthritis is initiated by damage to the cartilage of joints. The two most common injuries to joints are sports-related injuries and long term "repetitive use" joint injuries. Joints most commonly affected by osteoarthritis are the knees, hips and hands. In most cases, due to the essential weight-bearing function of the knees and hips, osteoarthritis in these joints causes much more disability than osteoarthritis of the hands. As cartilage degeneration progresses, secondary changes occur in other tissues in and around joints including bone, muscle, ligaments, menisci and synovium. The net effect of the primary failure of cartilage tissue and secondary damage to other tissues is that the patient experiences pain, swelling, weakness and loss of functional ability in the afflicted joint(s). These symptoms frequently progress to the point that they have a significant impact in terms of lost productivity and or quality of life consequences for the patient.

Articular cartilage is predominantly composed of chondrocytes, type II collagen, proteoglycans and water. Articular cartilage has no blood or nerve supply and chondrocytes are the only type of cell in this tissue. Chondrocytes are responsible for manufacturing the type II collagen and proteoglycans that form the cartilage matrix. This matrix in turn has physical-chemical properties that allow for saturation of the matrix with water. The net effect of this structural-functional relationship is that articular cartilage has exceptional wear characteristics and allows for almost frictionless movement between the articulating cartilage surfaces. In the absence of osteoarthritis, articular cartilage often provides a lifetime of pain-free weight bearing and unrestricted joint motion even under demanding physical conditions.

During fetal development, articular cartilage is initially derived from the interzone of mesenchymal condensations. The mesenchymal cells cluster together and synthesize matrix proteins. The tissue is recognized as cartilage when the accumulation of matrix separates the cells, which are spherical in shape and are now called chondrocytes. During cartilage formation and growth, chondrocytes proliferate rapidly and synthesize large volumes of matrix. Prior to skeletal maturity, chondrocytes are at their highest level of metabolic activity. As skeletal maturation is reached, the rate of chondrocyte metabolic activity and cell division declines. After completion of skeletal growth, most chondrocytes do not divide but do continue to synthesize matrix proteins such as collagens, proteoglycans and other noncollagenous proteins (1, 2).

Like all living tissues, articular cartilage is continually undergoing a process of renewal in which "old" cells and matrix components are being removed (catabolic activity) and "new" cells and molecules are being produced (anabolic activity). Relative to most tissues, the rate of anabolic/catabolic turnover in articular cartilage is low. Long-term maintenance of the structural integrity of mature cartilage relies on the proper balance between matrix synthesis and degradation. Chondrocytes maintain matrix equilibrium by responding to chemical and mechanical stimuli from their environment. Appropriate and effective chondrocyte responses to these stimuli are essential for cartilage homeostasis. Disruption of homeostasis through either inadequate anabolic activity or excessive catabolic activity can result in cartilage degradation and osteoarthritis (3). Most tissues that are damaged and have increased catabolic activity are able to mount an increased anabolic response that allows for tissue healing. Unfortunately, chondrocytes have very limited ability to up-regulate their anabolic activity and increase the synthesis of proteoglycan and type II collagen in response to damage or loss of cartilage matrix. This fundamental limitation of chondrocytes is the core problem that has precluded the development of therapies that can prevent and cure osteoarthritis. Additionally, there is a need for a definitive diagnostic test for detecting early osteoarthritis, and a prognostic test that effectively monitors a patient's response to therapy.

Joint pain is the most common manifestation of early osteoarthritis. The pain tends to be episodic lasting days to weeks and remitting spontaneously. Although redness and swelling of joints is uncommon, joints become tender during a flare-up of osteoarthritis.

"Mild" or "early stage osteoarthritis" is difficult to diagnose. The physician relies primarily on the patient's history and physical exam to make the diagnosis of mild osteoarthritis. X-rays do not show the underlying early changes in articular cartilage. There are no recognized biochemical markers used to confirm the diagnosis of early stage osteoarthritis.

X-ray changes confirm the diagnosis of moderate osteoarthritis. X-rays of normal joints reveal well preserved symmetrical joint spaces. Changes seen on the x-rays of patients with osteoarthritis include new bone formation (osteophytes), joint space narrowing and sclerosis (bone thickening). There are no recognized biochemical markers used to confirm the diagnosis of "moderate osteoarthritis" at this stage.

The clinical exam of a joint with severe osteoarthritis reveals tenderness, joint deformity and a loss of mobility. Passive joint movement during examination may elicit crepitus or the grinding of bone-on-bone as the joint moves. X-ray changes are often profound: the joint space may be obliterated and misalignment of the joint can be seen. New bone formation (osteophytes) is prominent. Again, there are no recognized biochemical markers used to confirm the diagnosis of "severe osteoarthritis".

"Osteoarthritis" is the most common chronic joint disease. It is characterized by progressive degeneration and eventual loss of cartilage. Currently, there is a need for an effective therapy that will alter the course of osteoarthritis. Further advances in preventing, modifying or curing the osteoarthritic disease process critically depends, at least in part, on a thorough understanding of the molecular mechanisms underlying anabolic and catabolic processes in cartilage. Since cellular functions are substantially determined by the genes that the cells express, elucidating the genes expressed in articular cartilage at different developmental and disease stages will inevitably provide new insights into the molecules and mechanisms involved in cartilage formation, injury, disease and repair.

cDNA libraries from putatively normal and severely osteoarthritic human cartilage tissue have been constructed (Kumar et al., $46^{th}$ Annual Meeting, Orthopaedic Res. Soc., Abstract, p. 1031). However, this work does not adequately address the differentiation of chondrocyte gene expression from differing severities of osteoarthritic human cartilage (mild, moderate, marked and severe). In addition, the "normal cartilage" samples were obtained from deceased donors more than 24 hours after death. Thus, this cDNA library does not truly reflect normal chondrocyte gene expression due to the rapid degeneration of RNA that occurs after cessation of perfusion to the sampled joint, as demonstrated by baboon studies, presented herein below.

Even upon construction of cDNA libraries from individuals demonstrating differing severities of osteoarthritis, it has been difficult to identify sequences which will be particularly useful in the diagnosis of osteoarthritis. More importantly previous studies have not identified sequences which will be either effective in diagnosing the degree of advancement of osteoarthritis so as to aid in both early detection and treatment, or in identifying novel therapeutic targets.

Even upon construction of cDNA libraries from individuals demonstrating differing severities of osteoarthritis, it has been difficult to identify sequences which will be particularly useful in the diagnosis of osteoarthritis. More importantly previous studies have not identified sequences which will be effective in diagnosing the degree of advancement of osteoarthritis so as to aid in both early detection, and treatment. Additionally previous studies have not identified sequences which will be effective in identifying agents which will be useful in treating osteoarthritis.

SUMMARY OF THE INVENTION

The invention relates to the identification and selection of sequences which demonstrate particular advantage in identifying individuals having osteoarthritis (OA). The invention also provides a selection of sequences particularly useful in diagnosing the degree of advancement of osteoarthritis of an individual and in the identification of novel therapeutic targets for OA. The invention further provides for the use of these sequences as a tool to diagnose disease progression and to monitor the efficacy of therapeutic regimens.

In one aspect, the present invention provides a composition comprising one or more nucleic acid sequences selected from the group consisting of nucleic acids identified in Table 29, Table 33, Table 37, Table 40, Table 44 and Table 48 and whose sequences are disclosed in Table 26. In another aspect, the present invention provides a vector comprising one or more nucleic acid sequences selected from the group consisting of nucleic acids identified in Table 29, Table 33, Table 37, Table 40, Table 44 and Table 48 and whose sequences are disclosed in Table 26.

In yet another aspect, the present invention provides a host cell comprising the vector comprising one or more nucleic acid sequences selected from the group consisting of nucleic acids identified in Table 29, Table 33, Table 37, Table 40, Table 44 and Table 48 and whose sequences are disclosed in Table 26.

In another aspect, the present invention provides an array comprising a plurality of nucleic acid members, and a solid substrate, each nucleic acid member having a unique position on the array and being stably associated with the solid substrate, where at least one member comprises a sequence of a nucleic acid selected from the group consisting of nucleic acids identified in Table 29, Table 33, Table 37, Table 40, Table 44 and Table 48 and whose sequences are disclosed in Table 26.

In another aspect, the present invention provides an array comprising a plurality of nucleic acid members, and a solid substrate, each nucleic acid member having a unique position on the array and being stably associated with the solid substrate, where at least one member comprises a sequence of a nucleic acid selected from the group consisting of nucleic acids identified in Table 29, 33, 40 and 44 and whose sequences are disclosed in Table 26.

In another aspect, the present invention provides an array comprising a plurality of nucleic acid members, and a solid substrate, each nucleic acid member having a unique position on the array and being stably associated with the solid substrate, where at least one member comprises a sequence of a nucleic acid selected from the group consisting of nucleic acids identified in Tables 29, 37 and 40 and 48 and whose sequences are disclosed in Table 26.

In another aspect, the present invention provides an array comprising a plurality of nucleic acid members, and a solid substrate, each nucleic acid member having a unique position on the array and being stably associated with the solid substrate, where at least one member comprises a sequence of a nucleic acid selected from the group consisting of nucleic acids identified in Tables 33 and 44 and whose sequences are disclosed in Table 26.

In another aspect, the present invention provides an array comprising a plurality of nucleic acid members, and a solid substrate, each nucleic acid member having a unique position on the array and being stably associated with the solid substrate, where at least one member comprises a sequence of a nucleic acid selected from the group consisting of nucleic acids identified in Tables 37 and 48 and whose sequences are disclosed in Table 26.

In another aspect, the present invention provides an array comprising a plurality of nucleic acid members, and a solid substrate, each nucleic acid member having a unique position on the array and being stably associated with the solid substrate, where at least one member comprises a sequence of a nucleic acid selected from the group consisting of nucleic acids identified in Tables 29 and 40 and whose sequences are disclosed in Table 26.

In another aspect, the present invention provides an array comprising a plurality of nucleic acid members, and a solid substrate, each nucleic acid member having a unique position on the array and being stably associated with the solid substrate, where at least one member comprises a sequence of a nucleic acid selected from the group consisting of nucleic acids identified in Table 40 and whose sequences are disclosed in Table 26.

In another aspect, the present invention provides an array comprising a plurality of nucleic acid members, and a solid substrate, each nucleic acid member having a unique position on the array and being stably associated with the solid substrate, where at least one member comprises a sequence of a nucleic acid selected from the group consisting of nucleic acids identified in Table 44 and whose sequences are disclosed in Table 26.

In another aspect, the present invention provides an array comprising a plurality of nucleic acid members, and a solid substrate, each nucleic acid member having a unique position on the array and being stably associated with the solid substrate, where at least one member comprises a sequence of a nucleic acid selected from the group consisting of nucleic acids identified in Table 48 and whose sequences are disclosed in Table 26.

In another aspect, the present invention provides an array comprising a plurality of nucleic acid members, and a solid substrate, each nucleic acid member having a unique position on the array and being stably associated with the solid substrate, where at least one member comprises a sequence of a nucleic acid selected from the group consisting of nucleic acids identified in Table 29 and whose sequences are disclosed in Table 26.

In another aspect, the present invention provides an array comprising a plurality of nucleic acid members, and a solid substrate, each nucleic acid member having a unique position on the array and being stably associated with the solid substrate, where at least one member comprises a sequence of a nucleic acid selected from the group consisting of nucleic acids identified in Table 33 and whose sequences are disclosed in Table 26.

In another aspect, the present invention provides an array comprising a plurality of nucleic acid members, and a solid substrate, each nucleic acid member having a unique position on the array and being stably associated with the solid substrate, where at least one member comprises a sequence of a nucleic acid selected from the group consisting of nucleic acids identified in Table 37 and whose sequences are disclosed in Table 26.

In one embodiment, the subject array of the present invention comprises a majority of the nucleic acid members which are selected from the group consisting of nucleic acids identified in Table 29, Table 33, Table 37, Table 40, Table 44 and Table 48 and whose sequences are disclosed in Table 26.

In one embodiment, the subject array of the present invention comprises a majority of the nucleic acid members which are selected from the group consisting of nucleic acids identified in Tables 29, 33, 40 and 44 and whose sequences are disclosed in Table 26.

In another embodiment, the subject array of the present invention comprises a majority of the nucleic acid members which are selected from the group consisting of nucleic acids identified in Tables 29, 37 and 40 and 48 and whose sequences are disclosed in Table 26.

In another embodiment, the subject array of the present invention comprises a majority of the nucleic acid members which are selected from the group consisting of nucleic acids identified in Tables 33 and 44 and whose sequences are disclosed in Table 26.

In another embodiment, the subject array of the present invention comprises a majority of the nucleic acid members which are selected from the group consisting of nucleic acids identified in Tables 37 and 48 and whose sequences are disclosed in Table 26.

In another embodiment, the subject array of the present invention comprises a majority of the nucleic acid members which are selected from the group consisting of nucleic acids identified in Tables 29 and 40 and whose sequences are disclosed in Table 26.

In another embodiment, the subject array of the present invention comprises a majority of the nucleic acid members which are selected from the group consisting of nucleic acids identified in Table 40 and whose sequences are disclosed in Table 26.

In another embodiment, the subject array of the present invention comprises a majority of the nucleic acid members which are selected from the group consisting of nucleic acids identified in Table 44 and whose sequences are disclosed in Table 26.

In another embodiment, the subject array of the present invention comprises a majority of the nucleic acid members which are selected from the group consisting of nucleic acids identified in Table 48 and whose sequences are disclosed in Table 26.

In another embodiment, the subject array of the present invention comprises a majority of the nucleic acid members which are selected from the group consisting of nucleic acids identified in Table 29 and whose sequences are disclosed in Table 26.

In another embodiment, the subject array of the present invention comprises a majority of the nucleic acid members which are selected from the group consisting of nucleic acids identified in Table 33 and whose sequences are disclosed in Table 26.

In another embodiment, the subject array of the present invention comprises a majority of the nucleic acid members which are selected from the group consisting of nucleic acids identified in Table 37 and whose sequences are disclosed in Table 26.

The present invention provides a method for diagnosing osteoarthritis in a patient comprising hybridizing a nucleic acid sample corresponding to RNA to an array comprising a solid substrate and a plurality of nucleic acid members, where at least one member is differentially expressed in cartilage isolated from a patient diagnosed with osteoarthritis, as compared to cartilage isolated from a normal individual, where cartilage isolated from the normal individual is isolated from cartilage tissue less than 14 hours post-mortem, and where each nucleic acid member has a unique position and is stably associated with the solid substrate and at least one member comprises a sequence of a nucleic acid selected from the group consisting of nucleic acids identified in Table 29, Table 33, Table 37, Table 40, Table 44 and Table 48 and whose sequences are disclosed in Table 26, and where hybridization of the nucleic acid sample to one or more the differentially expressed nucleic acid members is indicative of osteoarthritis.

The present invention also provides a method for diagnosing osteoarthritis in a patient comprising hybridizing a nucleic acid sample corresponding to RNA to an array comprising a solid substrate and a plurality of nucleic acid members, where at least one member is differentially expressed in cartilage isolated from a patient diagnosed with osteoarthritis, as compared to cartilage isolated from a normal individual, where cartilage isolated from the normal individual is isolated from cartilage tissue less than 14 hours post-mortem, and where each nucleic acid member has a unique position and is stably associated with the solid substrate and at least one member comprises a sequence of a nucleic acid selected from the group consisting of nucleic acids identified in Table 29 and Table 40 and whose sequences are disclosed in Table 26, and where hybridization of the nucleic acid sample to one or more the differentially expressed nucleic acid members is indicative of osteoarthritis.

The present invention also provides a method for diagnosing osteoarthritis in a patient comprising hybridizing a nucleic acid sample corresponding to RNA to an array comprising a solid substrate and a plurality of nucleic acid members, where at least one member is differentially expressed in cartilage isolated from a patient diagnosed with osteoarthritis, as compared to cartilage isolated from a normal individual, where cartilage isolated from the normal individual is isolated from cartilage tissue less than 14 hours post-mortem, and where each nucleic acid member has a unique position and is stably associated with the solid substrate and at least one member comprises a sequence of a nucleic acid selected from the group consisting of nucleic acids identified in Table 40 and whose sequences are disclosed in Table 26, and where hybridization of the nucleic acid sample to one or more the differentially expressed nucleic acid members is indicative of osteoarthritis.

The present invention also provides a method for diagnosing mild osteoarthritis in a patient comprising hybridizing a nucleic acid sample corresponding to RNA to an array comprising a solid substrate and a plurality of nucleic acid members, where at least one member is differentially expressed in cartilage isolated from a patient diagnosed with mild osteoarthritis, as compared to cartilage isolated from a normal individual, where cartilage isolated from the normal individual is isolated from cartilage tissue less than 14 hours post-mortem, and where each nucleic acid member has a unique position and is stably associated with the solid substrate and at least one member comprises a sequence of a nucleic acid selected from the group consisting of nucleic acids identified in Table 29, Table 33, Table 40, and Table 44 and whose sequences are disclosed in Table 26, and where hybridization of the nucleic acid sample to one or more the differentially expressed nucleic acid members is indicative of mild osteoarthritis.

The present invention also provides a method for diagnosing mild osteoarthritis in a patient comprising hybridizing a nucleic acid sample corresponding to RNA to an array comprising a solid substrate and a plurality of nucleic acid members, where at least one member is differentially expressed in cartilage isolated from a patient diagnosed with mild osteoarthritis, as compared to cartilage isolated from a normal individual, where cartilage isolated from the normal individual is isolated from cartilage tissue less than 14 hours post-mortem, and where each nucleic acid member has a unique position and is stably associated with the solid substrate and at least one member comprises a sequence of a nucleic acid selected from the group consisting of nucleic acids identified in Table 33 and Table 44 and whose sequences are disclosed in Table 26, and where hybridization of the nucleic acid sample to one or more the differentially expressed nucleic acid members is indicative of mild osteoarthritis.

The present invention also provides a method for diagnosing mild osteoarthritis in a patient comprising hybridizing a nucleic acid sample corresponding to RNA to an array comprising a solid substrate and a plurality of nucleic acid members, where at least one member is differentially expressed in cartilage isolated from a patient diagnosed with mild osteoarthritis, as compared to cartilage isolated from a normal individual, where cartilage isolated from the normal individual is isolated from cartilage tissue less than 14 hours post-mortem, and where each nucleic acid member has a unique position and is stably associated with the solid substrate and at least one member comprises a sequence of a nucleic acid selected from the group consisting of nucleic acids identified in Table 44 and whose sequences are disclosed in Table 26, and where hybridization of the nucleic acid sample to one or more the differentially expressed nucleic acid members is indicative of mild osteoarthritis.

The present invention also provides a method for diagnosing mild osteoarthritis in a patient comprising hybridizing a nucleic acid sample corresponding to RNA to an array comprising a solid substrate and a plurality of nucleic acid members, where at least one member is differentially expressed in cartilage isolated from a patient diagnosed with mild osteoarthritis, as compared to cartilage isolated from a normal individual, where cartilage isolated from the normal individual is isolated from cartilage tissue less than 14 hours post-mortem, and where each nucleic acid member has a unique position and is stably associated with the solid substrate and at least one member comprises a sequence of a nucleic acid selected from the group consisting of nucleic acids identified in Table 29 and whose sequences are disclosed in Table 26, and where hybridization of the nucleic acid sample to one or more the differentially expressed nucleic acid members is indicative of mild osteoarthritis.

The present invention also provides a method for diagnosing mild osteoarthritis in a patient comprising hybridizing a nucleic acid sample corresponding to RNA to an array comprising a solid substrate and a plurality of nucleic acid members, where at least one member is differentially expressed in cartilage isolated from a patient diagnosed with mild osteoarthritis, as compared to cartilage isolated from a normal individual, where cartilage isolated from the normal individual is isolated from cartilage tissue less than 14 hours post-mortem, and where each nucleic acid member has a unique position and is stably associated with the solid substrate and at least one member comprises a sequence of a nucleic acid selected from the group consisting of nucleic acids identified in Table 33 and whose sequences are disclosed in Table 26, and where hybridization of the nucleic acid sample to one or more the differentially expressed nucleic acid members is indicative of mild osteoarthritis.

The present invention also provides a method for diagnosing severe osteoarthritis in a patient comprising hybridizing a nucleic acid sample corresponding to RNA to an array comprising a solid substrate and a plurality of nucleic acid members, where at least one member is differentially expressed in cartilage isolated from a patient diagnosed with severe osteoarthritis, as compared to cartilage isolated from a normal individual, where cartilage isolated from the normal individual is isolated from cartilage tissue less than 14 hours post-mortem, and where each nucleic acid member has a unique position and is stably associated with the solid substrate and at least one member comprises a sequence of a nucleic acid selected from the group consisting of nucleic acids identified in Table 29, Table 37, Table 40, and Table 48 and whose sequences are disclosed in Table 26, and where hybridization of the nucleic acid sample to one or more the differentially expressed nucleic acid members is indicative of severe osteoarthritis.

The present invention also provides a method for diagnosing severe osteoarthritis in a patient comprising hybridizing a nucleic acid sample corresponding to RNA to an array comprising a solid substrate and a plurality of nucleic acid members, where at least one member is differentially expressed in cartilage isolated from a patient diagnosed with severe osteoarthritis, as compared to cartilage isolated from a normal individual, where cartilage isolated from the normal individual is isolated from cartilage tissue less than 14 hours post-mortem, and where each nucleic acid member has a unique position and is stably associated with the solid substrate and at least one member comprises a sequence of a nucleic acid selected from the group consisting of nucleic acids identified in Table 37 and Table 48 and whose sequences are disclosed in Table 26, and where hybridization of the nucleic acid sample to one or more the differentially expressed nucleic acid members is indicative of severe osteoarthritis.

The present invention also provides a method for diagnosing severe osteoarthritis in a patient comprising hybridizing a nucleic acid sample corresponding to RNA to an array comprising a solid substrate and a plurality of nucleic acid members, where at least one member is differentially expressed in cartilage isolated from a patient diagnosed with severe osteoarthritis, as compared to cartilage isolated from a normal individual, where cartilage isolated from the normal individual is isolated from cartilage tissue less than 14 hours post-mortem, and where each nucleic acid member has a unique position and is stably associated with the solid substrate and at least one member comprises a sequence of a nucleic acid selected from the group consisting of nucleic acids identified in Table 48 and whose sequences are disclosed in Table 26, and where hybridization of the nucleic acid sample to one or more the differentially expressed nucleic acid members is indicative of severe osteoarthritis.

The present invention also provides a method for diagnosing severe osteoarthritis in a patient comprising hybridizing a nucleic acid sample corresponding to RNA to an array comprising a solid substrate and a plurality of nucleic acid members, where at least one member is differentially expressed in cartilage isolated from a patient diagnosed with severe osteoarthritis, as compared to cartilage isolated from a normal individual, where cartilage isolated from the normal individual is isolated from cartilage tissue less than 14 hours post-mortem, and where each nucleic acid member has a unique position and is stably associated with the solid substrate and at least one member comprises a sequence of a nucleic acid selected from the group consisting of nucleic acids identified in Table 37 and whose sequences are disclosed in Table 26, and where hybridization of the nucleic acid sample to one or more the differentially expressed nucleic acid members is indicative of severe osteoarthritis.

In another embodiment, the invention provides for a kit comprising one or more arrays of the invention.

As another aspect, the present invention provides a method for monitoring efficacy of a drug for the treatment of osteoarthritis comprising hybridizing a nucleic acid sample taken from a first individual treated with the drug to an array comprising a solid substrate and a plurality of nucleic acid members, where each nucleic acid member has a unique position and is stably associated with the solid substrate and at least one member comprises a sequence of a nucleic acid selected from the group consisting of nucleic acids identified in Table 29, Table 33, Table 37, Table 40, Table 44, and Table 48 and whose sequences are disclosed in Table 26, and where one or more the nucleic acid members on the array being differentially expressed in the sample taken from the first individual treated with the drug, compared to a sample taken from a second individual not treated with the drug, is indicative of the efficacy of the drug for the treatment of osteoarthritis.

In one embodiment, when monitoring for drug efficacy in the treatment of osteoarthritis, the array preferably comprises at least one sequence selected from Table 33, Table 37, Table 40 and Table 44, more preferably a majority of sequences selected from Table 33, Table 37, Table 40 and Table 44 are chosen.

In one embodiment, the second individual is an individual prior to the treatment with said drug and the first individual is the same individual as the first individual during or after the treatment with said drug.

In another embodiment, when monitoring for drug efficacy in the treatment of severe osteoarthritis, the array preferably comprises at least one sequence selected from Table 37 and Table 48. More preferably the array comprises a majority of sequences selected from Table 37 and Table 48.

In another embodiment, when monitoring for drug efficacy in the treatment of mild osteoarthritis, the array preferably comprises at least one sequence selected from Table 33 and Table 44. More preferably the array comprises a majority of sequences selected from Table 33 and Table 44.

In some embodiment, the first and second individual in the method of monitoring drug efficacy is the same individual prior to the treatment with the drug and during or after the treatment with the drug.

The present invention also provides a method of identifying an agent that increases or decreases the expression of a nucleic acid sequence that is differentially expressed in a chondrocyte derived from any two or more of the following chondrocyte disease or developmental stages: fetal, mild osteoarthritic, moderate osteoarthritic, marked osteoarthritic and severe osteoarthritic, comprising: incubating a chondrocyte derived from a normal individual with a candidate agent, where the chondrocyte is isolated from a cartilage sample obtained from the normal individual less than 14 hours postmortem; isolating RNA from the chondrocyte; and hybridizing a probe to the RNA, the probe corresponding to a nucleic acid sequence selected from the group consisting of nucleic acids identified in Table 29, Table 33, Table 37, Table 40, Table 44 and Table 48 and whose sequences are disclosed in Table 26, where, as a result of the incubation in the presence of the candidate agent, a change in the level of expression of the nucleic acid sequence as compare to an incubation in the absence of the candidate agent, is indicative of the candidate agent increasing or decreasing the expression of the nucleic acid sequence that is differentially expressed in a chondrocyte derived from any two or more of the following chondrocyte disease or developmental stages: fetal, mild osteoarthritic, moderate osteoarthritic, marked osteoarthritic and severe osteoarthritic.

In one embodiment, the probe in the subject method of identifying an agent that increases or decreases the expression of a nucleic acid sequence that is differentially expressed in a chondrocyte corresponds to a nucleic acid sequence selected from the group consisting of nucleic acids identified in Table 29, Table 33, Table 40, Table 44.

In another embodiment, the probe in the subject method of identifying an agent that increases or decreases the expression of a nucleic acid sequence that is differentially expressed in a chondrocyte corresponds to a nucleic acid sequence selected from the group consisting of nucleic acids identified in Table 29, Table 37, Table 40, and Table 48.

In another embodiment, the probe in the subject method of identifying an agent that increases or decreases the expression of a nucleic acid sequence that is differentially expressed in a chondrocyte corresponds to a nucleic acid sequence selected from the group consisting of nucleic acids identified in Table 33 and Table 44.

In another embodiment, the probe in the subject method of identifying an agent that increases or decreases the expression of a nucleic acid sequence that is differentially expressed in a chondrocyte corresponds to a nucleic acid sequence selected from the group consisting of nucleic acids identified in Tables 37 and 48.

In another embodiment, the probe in the subject method of identifying an agent that increases or decreases the expression of a nucleic acid sequence that is differentially expressed in a chondrocyte corresponds to a nucleic acid sequence selected from the group consisting of nucleic acids identified in Tables 29 and 40.

In another embodiment, the probe in the subject method of identifying an agent that increases or decreases the expression of a nucleic acid sequence that is differentially expressed in a chondrocyte corresponds to a nucleic acid sequence selected from the group consisting of nucleic acids identified in Table 40.

In another embodiment, the probe in the subject method of identifying an agent that increases or decreases the expression of a nucleic acid sequence that is differentially expressed in a chondrocyte corresponds to a nucleic acid sequence selected from the group consisting of nucleic acids identified in Table 44.

In another embodiment, the probe in the subject method of identifying an agent that increases or decreases the expression of a nucleic acid sequence that is differentially expressed in a chondrocyte corresponds to a nucleic acid sequence selected from the group consisting of nucleic acids identified in Table 48.

In another embodiment, the probe in the subject method of identifying an agent that increases or decreases the expression of a nucleic acid sequence that is differentially expressed in a chondrocyte corresponds to a nucleic acid sequence selected from the group consisting of nucleic acids identified in Table 29.

In another embodiment, the probe in the subject method of identifying an agent that increases or decreases the expression of a nucleic acid sequence that is differentially expressed in a chondrocyte corresponds to a nucleic acid sequence selected from the group consisting of nucleic acids identified in Table 33.

In another embodiment, the probe in the subject method of identifying an agent that increases or decreases the expression of a nucleic acid sequence that is differentially expressed in a chondrocyte corresponds to a nucleic acid sequence selected from the group consisting of nucleic acids identified in Table 37.

BRIEF DESCRIPTION OF THE DRAWINGS

The objects and features of the invention can be better understood with reference to the following detailed description and drawings.

DETAILED DESCRIPTION OF THE INVENTION

Figure 1:
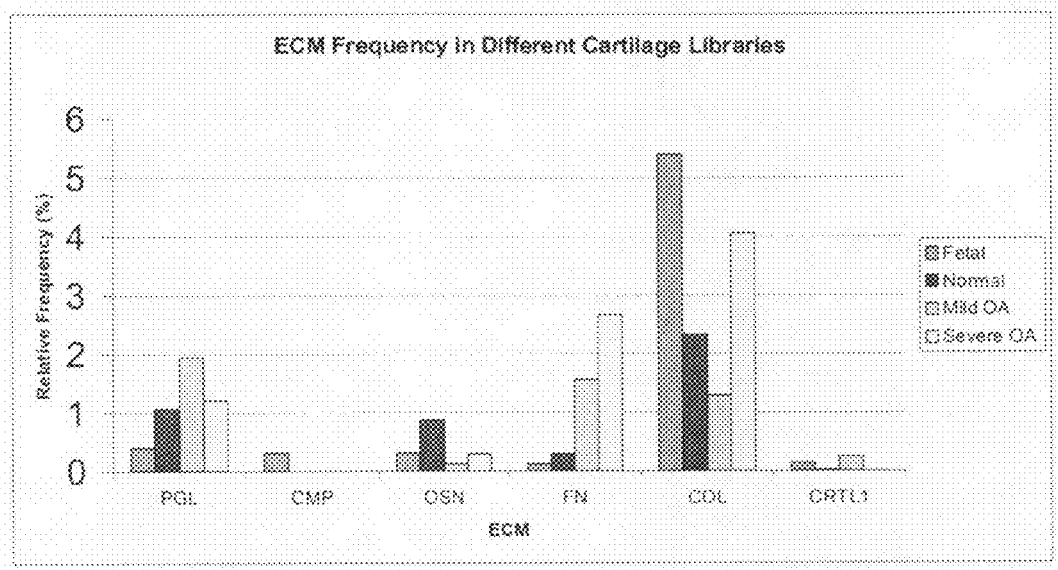
FIG. 1 is a graph according to one embodiment of the invention showing the relative EST frequency level of selected extracellular matrix (ECM) proteins among the fetal, normal, mild osteoarthritic and severe osteoarthritic cartilage cDNA libraries. ESTs per library. Legend: COL=collagen, PGL=proteoglycan, CMP=cartilage matrix proteins, OSN=osteonectin, FN=fibronectin, CRTL 1=cartilage link protein.

The invention relates to methods of profiling gene sequences expressed in human chondrocytes to identify differential gene expression in chondrocytes at different stages of development and disease. Differentially expressed genes and their products (e.g., mRNAs and proteins) can be used in methods for diagnosis, prognosis, screening, or treatment of osteoarthritis.

Definitions

The following definitions are provided for specific terms which are used in the following written description.

As used herein, "osteoarthritis" refers to a chronic disease in which the articular cartilage that lies on the ends of bones that form the articulating surface of the joints gradually degenerates over time. Cartilage degeneration can be caused by an imbalanced catabolic activity (removal of "old" cells and matrix components) and anabolic activity (production of "new" cells and molecules) (Westacott et al., 1996, *Semin Arthritis Rheum*, 25:254-72).

As used herein, "cartilage" or "articular cartilage" refers to elastic, translucent connective tissue in mammals, including human and other species. Cartilage is composed predominantly of chondrocytes, type II collagen, small amounts of other collagen types, other noncollagenous proteins, proteoglycans and water, and is usually surrounded by a perichondrium, made up of fibroblasts, in a matrix of type I and type II collagen as well as other proteoglycans. Although most cartilage becomes bone upon maturation, some cartilage remains in its original form in locations such as the nose, ears, knees, and other joints. The cartilage has no blood or nerve supply and chondrocytes are the only type of cell in this tissue.

As used herein, "chondrocyte" refers to cartilage cells.

As used herein, "synovial fluid" refers to fluid secreted from the "synovial sac" which surrounds each joint. Synovial fluid serves to protect the joint, lubricate the joint and provide nourishment to the articular cartilage. Synovial fluid useful according to the invention contains cells from which RNA can be isolated according to methods well known in the art as described herein.

As used herein, the term "osteoarthritis (OA) staging" or "osteoarthritis (OA) grading" refers to determining the degree of advancement or progression of the disease in the cartilage. In order to classify cartilage into different disease stages, a scoring system is used according to known methods in the art. Preferably the scoring system described in Marshall (Marshall W., 1996, *The Journal of Rheumatology*, 23:582-584, incorporated by reference) is used. According to this method, each of the 6 articular surfaces (patella, femoral trochlea, medial femoral condyle, medial tibial plateau, lateral femoral condyle and lateral tibial plateau) is assigned a cartilage grade based on the worst lesion present on that specific surface. A scoring system is then applied in which each articular surface receives an OA severity number value that reflects the cartilage severity grade for that surface. For example, if the medial femoral condyle has a grade I lesion as its most severe cartilage damage a value of 1 is assigned. A total score for the patient is then derived from the sum of the scores on the 6 articular surfaces. Based on the total score, each patient is placed into one of 40A groups: mild (early) (1-6), moderate (7-12), marked (13-18) and severe (>18).

As used herein, "diagnosis" refers to a process of determining if an individual is afflicted with a disease or ailment. "Diagnosis of OA" or "OA diagnosis", according to the invention, means determining if an individual is afflicted with OA, or, once a patient is diagnosed, determining the OA stage or grade as used herein based on the medical history and physical examination of the patient using methods known in the art (i.e., joint X ray). Preferably, OA stages are measured using the scoring system described by Marshall, supra. "Prognosis of OA" refers to a prediction of the probable occurrence and/or progression of OA in a patient, as well as the likelihood of recovery from OA, or the likelihood of ameliorating symptoms of OA or the likelihood of reversing the effects of OA.

As used herein, "patient" refers to a mammal who is diagnosed with a mild, moderate, marked, or severe form of OA.

As used herein, "normal" refers to an individual who has not shown any OA symptoms or has not been diagnosed with cartilage injury or OA. "Normal", according to the invention, also refers to a sample taken from normal individuals within 14 hours post-mortem. A normal cartilage tissue sample, for example, refers to the whole or a piece of cartilage isolated from cartilage tissue within 14 hours post-mortem from an individual who was not diagnosed with OA and whose corpse does not show any symptoms of OA at the time of tissue removal. In alternative embodiments of the invention, the "normal" cartilage tissue sample is isolated from cartilage tissue less than 14 hours post-mortem, e.g., within 13 hours, 12 hours, 11 hours, 10 hours, 9 hours, 8 hours, 7 hours, 6 hours, 5 hours, 4 hours, 3 hours, 2 hours, or 1 hour post-mortem. In one embodiment of the invention, the "normal" cartilage sample is isolated at 14 hours post-mortem and the integrity of mRNA samples extracted is confirmed.

As used herein, "mRNA integrity" refers to the quality of mRNA extracts from cartilage samples. mRNA extracts with good integrity do not appear to be degraded when examined by methods well known in the art, for example, by RNA agarose gel electrophoresis (e.g., Ausubel et al., John Weley & Sons, Inc., 1997, *Current Protocols in Molecular Biology*). Preferably, the mRNA samples have good integrity (e.g., less than 10%, preferably, less than 5%, and more preferably, less than 1% of the mRNA is degraded) to truly represent the gene expression levels of the cartilage samples from which they are extracted.

As used herein, "fetal" cartilage samples refer to samples taken from a fetus. The chondrocytes of fetal cartilage have a higher level of metabolic activity and cell division rates as compared to chondrocytes from cartilage derived from either a normal adult or from an adult diagnosed with any stage of OA (mild, moderate, marked and severe).

As used herein, "nucleic acid(s)" is interchangeable with the term "polynucleotide(s)" and it generally refers to any polyribonucleotide or poly-deoxyribonucleotide, which may be unmodified RNA or DNA or modified RNA or DNA. "Nucleic acids" include, without limitation, single- and double-stranded nucleic acids. As used herein, the term "nucleic acid(s)" also includes DNAs or RNAs as described above, that contain one or more modified bases. Thus, DNAs or RNAs with backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells. A "nucleic acid" or "nucleic acid sequence" may also be an expressed sequence tag (EST) according to some embodiments of the invention. An EST is a small part of the expressed sequence of a gene (i.e., the "tag" of a sequence), made from cDNA. An EST can be used to fish the rest of the gene out of the chromosome, by matching base pairs with part of the expressed sequence of the gene.

As used herein, "isolated" or "purified" when used in reference to a nucleic acid means that a naturally occurring sequence has been removed from its normal cellular (e.g., chromosomal) environment or is synthesized in a non-natural environment (e.g., artificially synthesized). Thus, an "isolated" or "purified" sequence may be in a cell-free solution or placed in a different cellular environment. The term "purified" does not imply that the sequence is the only nucleotide present, but that it is essentially free (about 90-95% pure) of non-nucleotide material naturally associated with it, and thus is distinguished from isolated chromosomes.

As used herein, the term "probe" refers to an oligonucleotide which forms a duplex structure with a sequence in the target nucleic acid, due to complementarity of at least one sequence in the probe with a sequence in the target region.

As defined herein, a "nucleic acid array" refers a plurality of unique nucleic acids (or "nucleic acid members") attached to one surface of a solid support at a density exceeding 20 different nucleic acids/cm$^2$ where each of the nucleic acid members is attached to the surface of the solid support in a non-identical pre-selected region. In one embodiment, the nucleic acid member attached to the surface of the solid support is DNA. In a preferred embodiment, the nucleic acid member attached to the surface of the solid support is cDNA. In another preferred embodiment, the nucleic acid member attached to the surface of the solid support is cDNA synthesized by polymerase chain reaction (PCR). Preferably, a nucleic acid member of the array according to the invention is at least 50 nucleotides in length. Preferably, a nucleic acid member of the array is less than 6,000 nucleotides in length. More preferably, a nucleic acid member of the array comprises an array less than 500 nucleotides in length. In one embodiment, the array comprises at least 500 different nucleic acid members attached to one surface of the solid support. In another embodiment, the array comprises at least 10 different nucleic acid members attached to one surface of the solid support. In yet another embodiment, the array comprises at least 10,000 different nucleic acid members attached to one surface of the solid support. In yet another embodiment, the array comprises at least 15,000 different nucleic acid members attached to one surface of the solid support. The term "nucleic acid", as used herein, is interchangeable with the term "polynucleotide".

As used herein, "a plurality of" or "a set of" refers to more than two, for example, 3 or more, 100 or more, or 1000 or more, or 10,000 or more.

As used herein, the term "majority" refers to a number representing more than 50% (e.g., 51%, 60%, or 70%, or 80% or 90% or up to 100%) of the total members of a composition. The term "majority", when referring to an array, it means more than 50% (e.g., 51%, 60%, or 70%, or 80% or 90% or up to 100%) of the total nucleic acid members that are stably associated with the solid substrate of the array.

As used herein, "attaching" or "spotting" refers to a process of depositing a nucleic acid onto a solid substrate to form a nucleic acid array such that the nucleic acid is irreversibly bound to the solid substrate via covalent bonds, hydrogen bonds or ionic interactions.

As used herein, "stably associated" refers to a nucleic acid that is irreversibly bound to a solid substrate to form an array via covalent bonds, hydrogen bonds or ionic interactions such that the nucleic acid retains its unique pre-selected position relative to all other nucleic acids that are stably associated with an array, or to all other pre-selected regions on the solid substrate under conditions in which an array is typically analyzed (i.e., during one or more steps of hybridization, washes, and/or scanning, etc.).

As used herein, "solid substrate" or "solid support" refers to a material having a rigid or semi-rigid surface. The terms "substrate" and "support" are used interchangeably herein with the terms "solid substrate" and "solid support". The solid support may be biological, non-biological, organic, inorganic, or a combination of any of these, existing as particles, strands, precipitates, gels, sheets, tubing, spheres, beads, containers, capillaries, pads, slices, films, plates, slides, chips, etc. Often, the substrate is a silicon or glass surface, (poly) tetrafluoroethylene, (poly)vinylidendifluoride, polystyrene, polycarbonate, a charged membrane, such as nylon 66 or nitrocellulose, or combinations thereof. In a preferred embodiment, the solid support is glass. Preferably, at least one surface of the substrate will be substantially flat. Preferably, the surface of the solid support will contain reactive groups, including, but not limited to, carboxyl, amino, hydroxyl, thiol, and the like. In one embodiment, the surface is optically transparent.

As used herein, "pre-selected region", "predefined region", or "unique position" refers to a localized area on a substrate which is, was, or is intended to be used for the deposit of a nucleic acid and is otherwise referred to herein in the alternative as a "selected region" or simply a "region." The preselected region may have any convenient shape, e.g., circular, rectangular, elliptical, wedge-shaped, etc. In some embodiments, a pre-selected region is smaller than about 1 cm$^2$, more preferably less than 1 mm$^2$, still more preferably less than 0.5 mm$^2$, and in some embodiments less than 0.1 mm$^2$. A nucleic acid member at a "pre-selected region", "predefined region", or "unique position" is one whose identity (e.g., sequence) can be determined by virtue of its position at the region or unique position.

As used herein, a "nucleic acid target" or "a target nucleic acid" is defined as a nucleic acid capable of binding to a nucleic acid member of complementary sequence through one or more types of chemical bonds, usually through complementary base pairing, i.e., through hydrogen bond formation. As used herein, a nucleic acid target may include natural (i.e., A, G, C, or T) or modified bases (7-deazaguanosine, inosine, etc.). In addition, the bases in nucleic acid probe may be joined by a linkage other than a phosphodiester bond, so long as it does not interfere with hybridization (i.e., the probe still specifically binds to its complementary sequence under standard stringent or selective hybridization conditions). Thus, nucleic acid targets may be peptide nucleic acids in which the constituent bases are joined by peptide bonds rather than phosphodiester linkages. Preferably, the nucleic acid targets are derived from human cartilage, blood or synovial fluid extracts. More preferably, the nucleic acid targets are single- or double-stranded DNA, RNA, or DNA-RNA hybrids, from human cartilage, blood or synovial fluid RNA extracts, and preferably from mRNA extracts.

As used herein, a "cartilage nucleic acid sample", refers to nucleic acids derived from cartilage. Preferably, a cartilage nucleic acid sample is RNA or is a nucleic acid corresponding to RNA, for example, cDNA.

As used herein, the term "hybridizing to" or "hybridization" refers to the hydrogen binding with a complementary nucleic acid, via an interaction between for example, a target nucleic acid sequence and a nucleic acid member in an array.

As used herein, "specific hybridization" or "selective hybridization" refers to hybridization which occurs when two nucleic acid sequences are substantially complementary (at least about 65% complementary over a stretch of at least 14 to 25 nucleotides, preferably at least about 75%, more preferably at least about 90% complementary). See Kanehisa, M., 1984, *Nucleic acids Res.*, 12:203, incorporated herein by reference. As a result, it is expected that a certain degree of mismatch is tolerated. Such mismatch may be small, such as a mono-, di- or tri-nucleotide. Alternatively, a region of mismatch can encompass loops, which are defined as regions in which there exists a mismatch in an uninterrupted series of four or more nucleotides. Numerous factors influence the efficiency and selectivity of hybridization of two nucleic acids, for example, a nucleic acid member on a array, to a target nucleic acid sequence. These factors include nucleic acid member length, nucleotide sequence and/or composition, hybridization temperature, buffer composition and potential for steric hindrance in the region to which the nucleic acid member is required to hybridize. A positive correlation exists between the nucleic acid member length and both the efficiency and accuracy with which a nucleic acid member will anneal to a target sequence. In particular, longer sequences have a higher melting temperature ($T_M$) than do shorter ones, and are less likely to be repeated within a given target sequence, thereby minimizing promiscuous hybridization. Hybridization temperature varies inversely with nucleic acid member annealing efficiency, as does the concentration of organic solvents, e.g., formamide, that might be included in a hybridization mixture, while increases in salt concentration facilitate binding. Under stringent annealing conditions, longer nucleic acids, hybridize more efficiently than do shorter ones, which are sufficient under more permissive conditions.

As used herein, the term "differential hybridization" refers to a probe that can hybridize to a same polynucleotide sequence obtained from two or more samples at different levels. A "differential hybridization" means that the ratio of the level of hybridization of the probe to the polynucleotide sequence isolated from one sample as compared to the polynucleotide sequence isolated from another sample is not equal to 1.0. For example, the ratio of the level of hybridization of the probe to the polynucleotide sequence isolated from one sample as compared to the polynucleotide sequence isolated from another sample is greater than or less than 1.0 and includes greater than 1.5 and less than 0.7 greater than 2 and less than 0.5. A differential hybridization also exists if the hybridization is detectable in one sample but not another sample.

As used herein, the term "up regulated" or "increased level of expression" in the context of this invention refers to a sequence which is expressed and which demonstrates an increased level of expression, as can be determined using microarray analysis or other similar analysis, in cartilage isolated from an individual having an identified disease state of osteoarthritis as determined by osteoarthritis staging as compared with cartilage isolated from normal individuals. An "increased level of expression" according to the present invention, is an increase in expression of at least 10% or more, for example, 20%, 30%, 40%, or 50%, 60%, 70%, 80%, 90% or more, or 2-fold, 3-fold, 4-fold, 5-fold, 10-fold, 50-fold, 100-fold or more as measured, for example, by the intensity of hybridization according to methods of the present invention. Up regulated sequences includes sequences having an increased level of expression in cartilage isolated individuals characterized as having mild OA or severe OA as compared with cartilage isolated from normal individuals.

As used herein, the term "down regulated" or "decreased level of expression" in the context of this invention refers to sequences which are expressed and which demonstrate a decreased level of expression, as can be determined using microarray analysis or other similar analysis, in cartilage isolated from cartilage of an individual having an identified disease state of osteoarthritis as determined by osteoarthritis staging as compared with cartilage isolated from normal individuals. An "decreased level of expression" according to the present invention, is a decrease in expression of at least 10% or more, for example, 20%, 30%, 40%, or 50%, 60%, 70%, 80%, 90% or more, or 2-fold, 3-fold, 4-fold, 5-fold, 10-fold, 50-fold, 100-fold or more as measured, for example, by the intensity of hybridization according to methods of the present invention. Down regulated sequences include sequences having a decreased level of expression in cartilage isolated individuals characterized as having mild OA or severe OA as compared with cartilage isolated from normal individuals.

As herein used, the term "standard stringent conditions" means hybridization will occur only if there is at least 95% and preferably, at least 97% identity between the sequences, wherein the region of identity comprises at least 10 nucleotides. In one embodiment, the sequences hybridize under stringent conditions following incubation of the sequences overnight at 42° C., followed by stringent washes (0.2×SSC at 65° C.). As several factors affect the stringency of hybridization, the combination of parameters is more important than the absolute measure of a single factor.

As used herein, the term "level of expression" refers to the measurable expression level of a given nucleic acid. The level of expression of a nucleic acid is determined by methods well known in the art. The term "differentially expressed" or "changes in the level of expression" refers to an increase or decrease in the measurable expression level of a given nucleic acid. As used herein, "differentially expressed" when referring to microarray analysis means the ratio of the level of expression of a given polynucleotide in one sample and the expression level of the given polynucleotide in another sample is not equal to 1.0. "Differentially expressed" when referring to microarray analysis according to the invention also means the ratio of the expression level of a given polynucleotide in one sample and the expression level of the given polynucleotide in another sample where the ratio is greater than or less than 1.0 and includes greater than 1.5 and less than 0.7, as well as greater than 2.0 and less than 0.5. A nucleic acid also is said to be differentially expressed in two samples if one of the two samples contains no detectable expression of the nucleic acid. Absolute quantification of the level of expression of a nucleic acid can be accomplished by including known concentration(s) of one or more control nucleic acid species, generating a standard curve based on the amount of the control nucleic acid and extrapolating the expression level of the "unknown" nucleic acid species from the hybridization intensities of the unknown with respect to the standard curve. The level of expression is measured by hybridization analysis using labeled target nucleic acids according to methods well known in the art. The label on the target nucleic acid can be a luminescent label, an enzymatic label, a radioactive label, a chemical label or a physical label. Preferably, target nucleic acids are labeled with a fluorescent molecule. Preferred fluorescent labels include, but are not limited to: fluorescein, amino coumarin acetic acid, tetramethylrhodamine isothiocyanate (TRITC), Texas Red, Cy3 and Cy5.

As used herein "differentially expressed" when referring to EST analysis refers to the relative expression level of a gene based on the frequency of ESTs representing the gene derived from a cDNA library as compared to the frequency of ESTs representing the same gene derived from another cDNA library. As described herein, the "relative EST frequency" of an EST is calculated by dividing the number of ESTs representing each specific gene by the total number of ESTs analyzed. Differences in "relative EST frequency" may be used as an indication of differential gene expression.

As used herein, the term "significant match", when referring to nucleic acid sequences, means that two nucleic acid sequences exhibit at least 65% identity, at least 70%, at least 75%, at least 80%, at least 85%, and preferably, at least 90% identity, using comparison methods well known in the art (i.e., Altschul, S. F. et al., 1997, *Nucl. Acids Res.*, 25:3389-3402; Schäffer, A. A. et al., 1999, *Bioinformatics* 15:1000-1011). As used herein, "significant match" encompasses non-contiguous or scattered identical nucleotides so long as the sequences exhibit at least 65%, and preferably, at least 70%, at least 75%, at least 80%, at least 85%, and preferably at least 90% identity, when maximally aligned using alignment methods routine in the art.

As used herein, a "novel sequence" or "novel expressed sequence tag (EST)" refers to a nucleic acid sequence which has no significant match to any existing sequence in the "nt", "nr", "est", "gss" and "htg" databases available through NCBI at the time each novel sequence was compared. "No significant match" preferably refers to a less than 65% match between a novel sequence being queried against other sequences in the database, and preferably, a less than 50% match, a less than 40% match, or a less than 30% match, after maximally aligning sequences using methods routine in the art.

As used herein, a "known sequence" refers to a nucleic acid sequence which has significant match to at least one existing sequence in the "nt", "nr", "est", "gss" and "htg" databases available through NCBI. "Known sequence with a function" refers to a nucleic acid with significant match to an existing sequence which encodes a polypeptide with a known function. "Known sequence with no function" refers to a nucleic acid that exhibits a significant match to an existing sequence which encodes a polypeptide of unknown function.

As used herein, a "chondrocyte-specific nucleic acid" is a nucleic acid sequence which is expressed at a detectable level in a chondrocyte and is not expressed at a detectable level in any other cell types as indicated by having no significant match to any sequence in any of the available databases comprising sequences from other cell types.

As used herein, a "chondrocyte enriched nucleic acid" or "chondrocyte enriched sequence" refers to a sequence which is differentially expressed in chondrocytes as compared to non-chondrocytes.

As used herein, "indicative of disease" refers to an expression pattern which is diagnostic of disease such that the expression pattern is found significantly more often in patients with a disease than in patients without the disease (as determined using routine statistical methods setting confidence levels at 95%). Preferably, an expression pattern which is indicative of disease is found in at least 70% of patients who have the disease and is found in less than 10% of patients who do not have the disease. More preferably, an expression pattern which is indicative of disease is found in at least 75%, at least 80%, at least 85%, at least 90%, at least 95% or more in patients who have the disease and is found in less than 10%, less than 8%, less than 5%, less than 2.5%, or less than 1% of patients who do not have the disease.

As used herein, a "gene expression pattern" or "gene expression profile" comprises the pattern of expression of one or more of a set of nucleic acid sequences where one or more members of the set are differentially expressed.

As used herein, "a nucleic acid array expression profile" is generated from the hybridization of nucleic acids derived from a sample to one or more nucleic acid members comprising an array according to the invention.

As used herein, a "therapeutic agent" or "agent" refers to a compound that increases or decreases the expression of a polynucleotide sequence that is differentially expressed in a chondrocyte from any two of the following developmental or osteoarthritis disease stages: (a) fetal, (b) mild, (c) moderate, (d) marked and (e) severe, or (f) chondrocyte from a normal individual, as defined herein. A therapeutic agent according to the invention also refers to a compound that increases or decreases the anabolic activity of a chondrocyte. The invention provides for a "therapeutic agent" that 1) prevents the onset of osteoarthritis; 2) reduces, delays, or eliminates osteoarthritis symptoms such as pain, swelling, weakness and loss of functional ability in the afflicted joints; 3) reduces, delays, or eliminates cartilage degeneration, and/or enhances chondrocyte metabolic activity and cell division rates; and/or 4) restores one or more expression profiles of one or more disease-indicative nucleic acids of a patient to a profile more similar to that of a normal individual when administered to a patient.

As used herein, the term "drug efficacy" refers to the effectiveness of a drug. "Drug efficacy" is usually measured by the clinical response of the patient who has been or is being treated with a drug. A drug is considered to have a high degree of efficacy, if it achieves desired clinical results, for example, the reduction of the symptoms of osteoarthritis or the prevention of osteoarthritis progression as described in the present specification. The amount of drug absorbed may be used to predict a patient's response. A general rule is that as the dose of a drug is increased, a greater effect is seen in the patient until a maximum desired effect is reached. If more drug is administered after the maximum point is reached, the side effects will normally increase.

Identifying Chondrocyte Enriched and Chondrocyte-Specific Polynucleotide Sequences cDNA libraries were constructed from human fetal, normal, mild osteoarthritic and severe osteoarthritic cartilage samples. The known and novel clones derived from these libraries were then used to construct human chondrocyte-specific microarrays to generate differential gene expression profiles useful as a diagnostic tool for detection of mild (early stage) osteoarthritis. Arrays of the invention are useful as a gold standard for osteoarthritis diagnosis and for use to identify and monitor therapeutic efficacy of new drug targets.

One effective and rapid way of characterizing gene expression patterns in a given tissue is through large-scale partial sequencing of a cDNA library produced from such a tissue to generate expressed sequence tags (ESTs). This approach has provided both quantitative and qualitative information on gene expression in a variety of tissues and cells (4-7). Since cDNA libraries represent gene transcription in the cells of the tissue used to construct the library, gene expression profiles generated by random sampling and sequencing is used for detailed genetic-level comparison between developmental, normal and pathological states of the tissue examined.

Many human genes are expressed at different levels in cartilage of different developmental (fetal vs. mature) or disease states. In some cases, a gene is not expressed at all in some developmental or disease states, and at high levels in others (see Tables 13, 27 and 28 for examples). According to the invention, differential analysis of chondrocyte gene expression during different stages of cartilage developmental and in different disease states using an EST-based approach has identified genes that play important roles in osteoarthritis pathogenesis and cartilage repair. The advantage of this method is that it provides gene expression information on a larger scale than other methods. The cDNA clones generated by this approach are also useful for functional studies of certain genes. This type of genomic-based approach has provided important novel insights into our understanding of the osteoarthritis disease process and provides for novel diagnostic, prognostic and therapeutic approaches.

Samples

Cartilage

In one aspect, cartilage is obtained from a fetus using methods known in the art. The chondrocytes of fetal cartilage have a higher level of metabolic activity and cell division rates as compared to chondrocytes from cartilage from either a normal adult or from an individual diagnosed with any stage of osteoarthritis (mild, moderate, marked and severe).

In another aspect, cartilage is obtained from a normal individual who is alive or is obtained from cartilage tissue less than 14 hours post mortem, according to methods known in the art and described below. Normal articular cartilage from human adults are obtained using any known method. However, truly normal cartilage cannot generally be sampled from live donors due to ethical considerations. Preferably, normal cartilage samples are obtained from deceased donors, within a fourteen-hour post-mortem window after cessation of perfusion to the sampled joint, to minimize the degradation of RNA observed beyond the window. In other embodiments, the "normal" tissue is obtained less than 14 hours post-mortem, such as 13, 12, 11, 10, 9, 8, 6, 4, 2, or 1 hour post-mortem. A baboon study was conducted to confirm this approach and is described herein below in Example 11. Preferably the normal cartilage is obtained less than 14 hours post-mortem. More preferably, the normal cartilage is obtained less than 12 hours post-mortem.

Preferably, cartilage also is isolated from the following disease stages of osteoarthritis: mild, marked, moderate and severe. Human cartilage samples from osteoarthritic individuals are obtained using any known method. Preferably the cartilage is obtained from individuals undergoing arthroscopy or total knee replacements and samples are stored in liquid nitrogen until needed. In a preferred embodiment, a minimum of 0.05 g of cartilage sample is isolated to obtain 2 μg total RNA extract for the construction of a cDNA library. In another preferred embodiment, a minimum of 0.025 g cartilage sample is isolated to obtain 1 μg total RNA extract to use as a target sample for a microarray. A cartilage sample that is useful according to the invention is in an amount that is sufficient for the detection of one or more nucleic acid sequences according to the invention.

Blood and Synovial Fluid

Samples useful according to the invention also include blood and synovial fluid samples.

In one aspect, blood is obtained from a normal patient or from an individual diagnosed with, or suspected of having, osteoarthritis according to methods of phlebotomy well known in the art. A blood sample useful according to the invention is in an amount ranging from 1 μl to 100 ml, preferably 10 μl to 50 ml, more preferably 10 μl to 25 ml and most preferably 10 μl to 1 ml. A blood sample that is useful according to the invention is in an amount that is sufficient for the detection of one or more nucleic acid sequences according to the invention. In one embodiment, nucleic acids contained within the blood sample are amplified, for example, by polymerase chain reaction (PCR) or by RT-PCR. Other amplification methods known in the art are also encompassed within the scope of the invention (e.g., ligase chain reaction, NASBA, 3SR, and the like).

A synovial fluid sample is obtained from an individual diagnosed with, or suspected of having osteoarthritis according to methods well known in the art. Preferably, synovial fluid is collected from a human knee joint by aspiration at arthroscopy. A synovial fluid sample useful according to the invention is in an amount ranging from 0.1 ml to 20 ml and preferably 0.5 ml to 10 ml. A synovial fluid sample that is useful according to the invention is in an amount that is sufficient for the detection of one or more nucleic acid sequences according to the invention.

Developmental and Disease Stages of Articular Cartilage

Chondrocytes are preferably obtained from any of the following developmental and disease stages: fetal, normal, mild osteoarthritic, moderate osteoarthritic, marked osteoarthritic or severe osteoarthritic.

Cartilage isolated from a human fetus (e.g., during fetal development) is characterized above, and is useful according to the invention for analysis of fetal chondrocytes.

Cartilage isolated from a "normal" individual, defined herein, also is useful according to the invention for isolation and analysis of "normal" chondrocytes.

Cartilage isolated from a patient diagnosed with any one of: mild, moderate, marked and severe osteoarthritis also is useful in the present invention.

In order to classify cartilage according to disease state, a scoring system is used, whereby subjective decisions by the arthroscopist are minimized. The scoring system which defines disease states described herein is that of Marshall, supra, incorporated herein by reference. According to this method, each of the 6 articular surfaces (patella, femoral trochlea, medial femoral condyle, medial tibial plateau, lateral femoral condyle and lateral tibial plateau) is assigned a cartilage grade based on the worst lesion present on that specific surface. A scoring system is then applied in which each articular surface receives an osteoarthritis severity number value that reflects the cartilage severity grade for that surface, as described in Table 1.

TABLE 1

Articular Cartilage Grading System

| Grade | Articular Cartilage | Points |
|---|---|---|
| 0 | Normal | 0 |
| I | Surface intact-softening, edema | 1 |
| II | Surface-disrupted-partial thickness lesions (no extension to bone) | 2 |
| III | Full thickness lesions-extensions to intact bone | 3 |
| IV | Bone erosion or eburnation | 4 |

For example, if the medial femoral condyle has a grade I lesion as its most severe cartilage damage, a value of 1 is assigned. A total score for the patient is then derived from the sum of the scores of the 6 articular surfaces. Based on the total score, each patient is placed into one of 4 osteoarthritis groups: mild (1-6), moderate (7-12), marked (13-18) and severe (>18).

RNA Preparation

In one aspect, RNA is isolated from cartilage samples from various disease or developmental stages as described herein. Samples can be from single patients or can be pooled from multiple patients.

In another aspect, RNA is isolated directly from synovial fluid of persons with various disease or developmental stages of osteoarthritis as described herein. Samples can be from single patients or can be pooled from multiple patients.

In another aspect, RNA is isolated directly from blood samples of persons with various disease or developmental stages of osteoarthritis as described herein. Samples can be from single patients or can be pooled from multiple patients.

Total RNA is extracted from the cartilage samples according to methods well known in the art. In one embodiment, RNA is purified from cartilage tissue according to the following method. Following removal of a tissue of interest from an individual or patient, the tissue is quick frozen in liquid nitrogen, to prevent degradation of RNA. Upon the addition of a volume of tissue guanidinium solution, tissue samples are ground in a tissuemizer with two or three 10-second bursts. To prepare tissue guanidinium solution (1 L) 590.8 g guanidinium isothiocyanate is dissolved in approximately 400 ml DEPC-treated $H_2O$. 25 ml of 2 M Tris-Cl, pH 7.5 (0.05 M final) and 20 ml $Na_2EDTA$ (0.01 M final) is added, the solution is stirred overnight, the volume is adjusted to 950 ml, and 50 ml 2-ME is added.

Homogenized tissue samples are subjected to centrifugation for 10 min at 12,000×g at 12° C. The resulting supernatant is incubated for 2 min at 65° C. in the presence of 0.1 volume of 20% Sarkosyl, layered over 9 ml of a 5.7M CsCl solution (0.1 g CsCl/ml), and separated by centrifugation overnight at 113,000×g at 22° C. After careful removal of the supernatant, the tube is inverted and drained. The bottom of the tube (containing the RNA pellet) is placed in a 50 ml plastic tube and incubated overnight (or longer) at 4° C. in the presence of 3 ml tissue resuspension buffer (5 mM EDTA, 0.5% (v/v) Sarkosyl, 5% (v/v) 2-ME) to allow complete resuspension of the RNA pellet. The resulting RNA solution is extracted sequentially with 25:24:1 phenol/chloroform/isoamyl alcohol, followed by 24:1 chloroform/isoamyl alcohol, precipitated by the addition of 3 M sodium acetate, pH 5.2, and 2.5 volumes of 100% ethanol, and resuspended in DEPC water (Chirgwin et al., 1979, *Biochemistry*, 18:5294).

Alternatively, RNA is isolated from cartilage tissue according to the following single step protocol. The tissue of interest is prepared by homogenization in a glass teflon homogenizer in 1 ml denaturing solution (4M guanidinium thiosulfate, 25 mM sodium citrate, pH 7.0, 0.1 M 2-ME, 0.5% (w/v) N-laurylsarkosine) per 100 mg tissue. Following transfer of the homogenate to a 5-ml polypropylene tube, 0.1 ml of 2 M sodium acetate, pH 4, 1 ml water-saturated phenol, and 0.2 ml of 49:1 chloroform/isoamyl alcohol are added sequentially. The sample is mixed after the addition of each component, and incubated for 15 min at 0-4° C. after all components have been added. The sample is separated by centrifugation for 20 min at 10,000×g, 4° C., precipitated by the addition of 1 ml of 100% isopropanol, incubated for 30 minutes at −20° C. and pelleted by centrifugation for 10 minutes at 10,000×g, 4° C. The resulting RNA pellet is dissolved in 0.3 ml denaturing solution, transferred to a microfuge tube, precipitated by the addition of 0.3 ml of 100% isopropanol for 30 minutes at −20° C., and centrifuged for 10 minutes at 10,000×g at 4° C. The RNA pellet is washed in 70% ethanol, dried, and resuspended in 100-200 μl DEPC-treated water or DEPC-treated 0.5% SDS (Chomczynski and Sacchi, 1987, *Anal. Biochem.*, 162: 156).

Preferably, the cartilage samples are finely powdered under liquid nitrogen and total RNA is extracted using TRIzol® reagent (GIBCO/BRL).

Alternatively, RNA is isolated from blood by the following protocol. Lysis Buffer is added to blood sample in a ratio of 3 parts Lysis Buffer to 1 part blood (Lysis Buffer (1 L) 0.6 g EDTA; 1.0 g $KHCO_2$, 8.2 g $NH_4Cl$ adjusted to pH 7.4 (using NaOH)). Sample is mixed and placed on ice for 5-10 minutes until transparent. Lysed sample is centrifuged at 1000 rpm for 10 minutes at 4° C., and supernatant is aspirated. Pellet is resuspended in 5 ml Lysis Buffer, and centrifuged again at 1000 rpm for 10 minutes at 4° C. Pelleted cells are homogenized using TRIzol® (GIBCO/BRL) in a ratio of approximately 6 ml of TRIzol® for every 10 ml of the original blood sample and vortexed well. Samples are left for 5 minutes at room temperature. RNA is extracted using 1.2 ml of chloroform per 1 ml of TRIzol®. Sample is centrifuged at 12,000×g for 5 minutes at 4° C. and upper layer is collected. To upper layer, isopropanol is added in ratio of 0.5 ml per 1 ml of TRIzol®. Sample is left overnight at −20° C. or for one hour at −20° C. RNA is pelleted in accordance with known methods, RNA pellet air dried, and pellet resuspended in DEPC treated $ddH_2O$. RNA samples can also be stored in 75% ethanol where the samples are stable at room temperature for transportation.

Alternatively, RNA is isolated from synovial fluid using TRIzol® reagent (GIBCO/BRL).

Purity and integrity of RNA is assessed by absorbance at 260/280 nm and agarose gel electrophoresis followed by inspection under ultraviolet light.

Construction of cDNA Libraries cDNA libraries are constructed according to methods well known in the art (see for example Ausubel, supra, and Sambrook, supra, incorporated herein by reference).

In one aspect, cDNA samples, i.e., DNA that is complementary to RNA such as mRNA are prepared. The preparation of cDNA is well-known and well-documented in the prior art.

cDNA may be prepared according to the following method. Total cellular RNA is isolated (as described) and passed through a column of oligo(dT)-cellulose to isolate polyA RNA. The bound polyA mRNAs are eluted from the column with a low ionic strength buffer. To produce cDNA molecules, short deoxythymidine oligonucleotides (12-20 nucleotides)

are hybridized to the polyA tails to be used as primers for reverse transcriptase, an enzyme that uses RNA as a template for DNA synthesis. Alternatively, or additionally, mRNA species are primed from many positions by using short oligonucleotide fragments comprising numerous sequences complementary to the mRNA of interest as primers for cDNA synthesis. The resultant RNA-DNA hybrid is converted to a double stranded DNA molecule by a variety of enzymatic steps well-known in the art (Watson et al., 1992, *Recombinant DNA*, 2nd edition, Scientific American Books, New York).

To construct a cDNA library, the poly (A)⁺ RNA fraction may be isolated by oligo-dT cellulose chromatography (Pharmacia), and 3-5 ug poly (A)⁺ RNA is used to construct a cDNA library in the λ ZAP Express vector (Stratagene). Alternatively, cDNA libraries may be constructed into λTriplEx2 vector through a PCR-based method, using SMART (Switching Mechanism At 5' end of RNA Transcript) cDNA Library Construction Kit (Clontech). First-strand cDNA is synthesized with an Xho I-oligo (dT) adapter-primer in the presence of 5'-methyl dCTP. After second-strand synthesis and ligation of EcoRI adapters, the cDNAs are digested with Xho I, resulting in cDNA flanked by EcoRI sites at the 5'-ends and Xho I sites at the 3' ends. Digested cDNAs are size-fractionated in Sephacryl S-500 spin columns (Stratagene), then ligated into the λ ZAP Express vector predigested with EcoRI and Xho I. The resulting DNA/cDNA concatomers are packaged using Gigapack Gold packaging extracts. After titration, aliquots of primary packaging mix are stored in 7% DMSO at −80° C. as primary library stocks, and the rest are amplified to establish stable library stocks.

From the amplified library, phage plaques are plated onto an appropriate medium. Preferably, phage plaques are plated at a density of 200-500 pfu/150 mm plate onto an *Escherichia coli* XL1-blue MRF' lawn with IPTG/X-gal for color selection. The plaques are then randomly picked and positive inserts are identified by polymerase chain reaction (PCR), according to methods well known in the art and described hereinbelow. Preferably, plaques are picked into 75 ul suspension media buffer (100 mM NaCl, 10 mM MgSO₄, 1 mM Tris, pH7.5, 0.02% gelatin). Phage elutes (5 ul) may be used for PCR reactions (50 ul total volume) with 125 umol/L of each dNTP (Pharmacia), 10 pmol each of modified T3 (5'-GCCAAGCTCGAAATTAACCCTCACTAAAGGG-3') (SEQ ID NO: 58,993) and T7 (5'-CCAGTGAATTG-TAATACGACTCACTATAGGGCG-3') (SEQ ID NO: 58,994) primers, and 2 U of Taq DNA polymerase (Pharmacia). Reactions are cycled in a DNA Thermal Cycler (Perkin-Elmer) [denaturation at 95° C. for 5 minutes, followed by 30 cycles of amplification (94° C., 45 seconds; 55° C., 30 seconds; 72° C., 3 minutes) and a terminal isothermal extension (72° C., 3 minutes)]. Agarose gel electrophoresis is used to assess the presence and purity of inserts.

The PCR product is then subjected to DNA sequencing using known methods (see Ausubel et al., supra and Sambrook et al., supra). Methods of sequencing employ such enzymes as the Klenow fragment of DNA polymerase I, Sequenase® (US Biochemical Corp, Cleveland, Ohio), Taq polymerase (Perkin Elmer, Norwalk, Conn.), thermostable T7 polymerase (Amersham, Chicago, Ill.), or combinations of recombinant polymerases and proofreading exonucleases such as the ELONGASE Amplification System (Gibco BRL, Gaithersburg, Md.). Preferably, the process is automated with machines such as the Hamilton Micro Lab 2200 (Hamilton, Reno Nev.), Peltier Thermal Cycler (PTC200; MJ Research, Watertown, Mass.), the ABI 377 DNA sequencers (Perkin Elmer), and the PE Biosystems ABI Prism 3700 DNA Analyzer.

PCR products are first subjected to DNA sequencing reactions using specific primers, BigDye™ Terminator Cycle Sequencing v2.0 Ready Reaction (PE Biosystems), Tris MgCl buffer and water in a thermocycler. Sequencing reactions were incubated at 94° C. for 2 minutes, followed by 25 cycles of 94° C., 30 seconds; 55° C., 20 seconds; and 72° C., 1 minute; and 15 cycles of 94° C., 30 seconds; and 72° C. for 1 minute; and 72° C. for 5 minutes. Reactions were then put on hold at 4° C. until purified using methods well known in the prior art (i.e. alcohol precipitation or ethanol precipitation). Automated sequencing is preferably carried out with a PE Biosystems ABI Prism 3700 DNA Analyzer.

PCR

In one aspect, nucleic acid sequences of the invention are amplified by the polymerase chain reaction (PCR). PCR methods are well-known to those skilled in the art.

PCR provides a method for rapidly amplifying a particular nucleic acid sequence by using multiple cycles of DNA replication catalyzed by a thermostable, DNA-dependent DNA polymerase to amplify the target sequence of interest. PCR requires the presence of a nucleic acid to be amplified, two single-stranded oligonucleotide primers flanking the sequence to be amplified, a DNA polymerase, deoxyribonucleoside triphosphates, a buffer and salts.

The method of PCR is well known in the art. PCR, is performed as described in Mullis and Faloona, 1987, *Methods Enzymol.*, 155: 335, herein incorporated by reference.

PCR is performed using template DNA (at least 1 fg; more usefully, 1-1000 ng) and at least 25 pmol of oligonucleotide primers. A typical reaction mixture includes: 2 μl of DNA, 25 pmol of oligonucleotide primer, 2.5 μl of 10H PCR buffer 1 (Perkin-Elmer, Foster City, Calif.), 0.4 μl of 1.25 μM dNTP, 0.15 μl (or 2.5 units) of Taq DNA polymerase (Perkin Elmer, Foster City, Calif.) and deionized water to a total volume of 25 μl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

Several techniques for detecting PCR products quantitatively without electrophoresis may be useful according to the invention. One of these techniques, for which there are commercially available kits such as Taqman™ (Perkin Elmer, Foster City, Calif.), is performed with a transcript-specific antisense probe. This probe is specific for the PCR product (e.g. a nucleic acid fragment derived from a gene) and is prepared with a quencher and fluorescent reporter probe complexed to the 5' end of the oligonucleotide. Different fluorescent markers are attached to different reporters, allowing for measurement of two products in one reaction. When Taq DNA polymerase is activated, it cleaves off the fluorescent reporters of the probe bound to the template by virtue of its 5'-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions are performed in 96 well plates so that samples derived from many individuals are processed and measured simultaneously. The Taqman™ system has the additional advantage of not requiring gel electrophoresis and allows for quantification when used with a standard curve.

Nucleic acid Sequences Useful According to the Invention

The invention provides for isolated nucleic acid sequences including ESTs which can be used as probes, arrayed on microarrays, and/or used for the development of therapies to treat osteoarthritis.

In one aspect, cartilage gene expression profiles at different developmental stages are identified. Another aspect of the invention is to monitor cartilage gene expression profiles of osteoarthritis patients diagnosed with different stages of osteoarthritis. A third aspect of the invention is to screen for potential therapeutic agents which alter the gene expression profile of diseased cartilage cells. The invention therefore provides for nucleic acid sequences that are present at each of the following developmental and disease stages: normal, fetal, mild osteoarthritic, moderate osteoarthritic, marked osteoarthritic and severe osteoarthritic. The invention also provides for nucleic acid sequences that are differentially expressed in any two of the following developmental and disease stages: normal, fetal, mild osteoarthritic, moderate osteoarthritic, marked osteoarthritic and severe osteoarthritic.

Nucleic acids useful according to the invention are prepared by isolating cartilage tissue samples from a developmental or disease stage (normal, fetal, mild osteoarthritic, moderate osteoarthritic, marked osteoarthritic and severe osteoarthritic), preparing a cDNA library (as described above), and performing large-scale partial sequencing (described herein) of the cDNA library to generate Expressed Sequence Tags (ESTs). An EST useful according to the invention is preferably in the range of 50-1000 nucleotides and most preferably 50-500 nucleotides in length.

The invention provides for nucleic acid sequences or ESTs that are categorized as "novel" or "known", including "known sequences with a function" and "known sequences without a known function", all defined herein.

Nucleic Acid Members and Probes

In one aspect, the invention provides nucleic acid members and probes that bind specifically to a target nucleic acid sequence (e.g., present in a cartilage nucleic acid sample).

Nucleic acid members are stably associated with a solid support to comprise an array according to the invention. The length of a nucleic acid member can range from 50 to 6000 nucleotides, 100 to 500 nucleotides, and in other embodiments, from 500 to 1500 nucleotides. The nucleic acid members may be single or double stranded, and/or may be PCR fragments amplified from cDNA.

The invention also provides for nucleic acid sequences comprising a probe. In a certain embodiment, a probe is labeled, according to methods known in the art. A probe according to the invention is 50 to 5000 nucleotides, more preferably 100-500 nucleotides and most preferably 50 to 250 nucleotides in length. The probe may be single or double stranded, and may be a PCR fragment amplified from cDNA.

The nucleic acid members and probes according to the invention can be used to detect target sequences such as chondrocyte enriched or chondrocyte-specific sequences, and preferably sequences whose presence in a sample are indicative, or diagnostic or prognostic, of a stage of osteoarthritis.

The target nucleic acid sequences to be analyzed are preferably from human cartilage, blood or synovial fluid and preferably comprise RNA or nucleic acid corresponding to RNA, (i.e., cDNA or amplified products of RNA or cDNAs).

Data Acquisition and Analysis of EST Sequences

The invention provides for EST sequences including "novel sequences", "novel expressed sequence tags (ESTs)" and "known sequences" including "known sequences with a function" and "known sequences with no known function".

The generated EST sequences are searched against available databases, including the "nt", "nr", "est", "gss" and "htg" databases available through NCBI to determine putative identities for ESTs matching to known genes or other ESTs. Relative EST frequency level can then be calculated using known methods. Functional characterization of ESTs with known gene matches are made according to any known method. Preferably, generated EST sequences are compared to the non-redundant Genbank/EMBL/DDBJ and dbEST databases using the BLAST algorithm (8). A minimum value of $P=10^{-10}$ and nucleotide sequence identity >95%, where the sequence identity is non-contiguous or scattered, are required for assignments of putative identities for ESTs matching to known genes or to other ESTs. Construction of a non-redundant list of genes represented in the EST set is done with the help of Unigene, Entrez and PubMed at the National Center for Biotechnology Information (NCBI) site (at www.ncbi.nlm.nih.gov/). Relative gene expression frequency is calculated by dividing the number of EST copies for each gene by the total number of ESTs analyzed.

Genes are identified from ESTs according to known methods. To identify novel genes from an EST sequence, the EST should preferably be at least 100 nucleotides in length, and more preferably 150 nucleotides in length, for annotation. Preferably, the EST exhibits open reading frame characteristics (i.e., can encode a putative polypeptide).

Because of the completion of the Human Genome Project, a specific EST which matches with a genomic sequence can be mapped onto a specific chromosome based on the chromosomal location of the genomic sequence. However, no function may be known for the protein encoded by the sequence and the EST would then be considered "novel" in a functional sense. In one aspect, the invention is used to identify a novel EST which is part of a larger known sequence for which no function is known is used to determine the function of a gene comprising the EST (e.g., such as the role of expression products produced by the gene in chondrogenesis and/or in a pathology affecting chondrocytes). Alternatively, or additionally, the EST can be used to identify an mRNA or polypeptide encoded by the larger sequence as a diagnostic or prognostic marker of chondrogenesis and/or of a pathology affecting chondrocytes.

Having identified an EST corresponding to a larger sequence as chondrocyte enriched or chondrocyte-specific, other portions of the larger sequence which comprises the EST can be used in assays to elucidate gene function, e.g., to isolate polypeptides encoded by the gene, to generate antibodies specifically reactive with these polypeptides, to identify binding partners of the polypeptides (receptors, ligands, agonists, antagonists and the like) and/or to detect the expression of the gene (or lack thereof) in chondrocytes in fetal, adult, normal, and/or diseased individuals.

In another aspect, the invention provides for nucleic acid sequences that do not demonstrate a "significant match" to any of the publicly known sequences in sequence databases at the time a query is done. Longer genomic segments comprising these types of novel EST sequences can be identified by probing genomic libraries, while longer expressed sequences can be identified in cDNA libraries and/or by performing polymerase extension reactions (e.g., RACE) using EST sequences to derive primer sequences as is known in the art. Longer fragments can be mapped to particular chromosomes by FISH and other techniques and their sequences compared to known sequences in genomic and/or expressed sequence databases and further functional analysis can be performed as described above.

Using the methods according to the invention, out of a total of 57,422 ESTs from the four cDNA libraries, no significant match was found for 618 sequences. The remaining sequences were characterized as shown in Table 12.

Identified genes can be catalogued according to their putative function. Functional characterization of ESTs with known gene matches is preferably made according to the categories described by Hwang et al (5). The distribution of genes in each of the subcellular categories is indicative of the dynamic state of the tissue and will provide important insights into the osteoarthritis disease process. The results of this analysis are provided in Table 19 where the total number of ESTs identified by the method in different human cartilage libraries are characterized based on the functional classification of known genes identified in each library.

Alternative methods for analyzing ESTs are also available. For example, the ESTs from each library may be assembled into contigs with sequence alignment, editing, and assembly programs such as PHRED and PHRAP (Ewing, et al., 1998, Genome Res. 3:175, incorporated herein; world wide web bozeman.genome.washington.edu/).Contig redundancy is reduced by clustering nonoverlapping sequence contigs using the EST clone identification number, which is common for the nonoverlapping 5' and 3' sequence reads for a single EST cDNA clone. In one aspect, the consensus sequence from each cluster is compared to the non-redundant Genbank/EMBL/DDBJ and dbEST databases using the BLAST algorithm with the help of unigene, Entrez and PubMed at the NCBI site.

Known Nucleic acid Sequences or ESTs and Novel Nucleic Acid Sequences or ESTs

An EST that exhibits a significant match (>65%, and preferably 90% or greater, identity) to at least one existing sequence in an existing nucleic acid sequence database is characterized as a "known" sequence according to the invention. Within this category, some known ESTs match to existing sequences which encode polypeptides with known function(s) and are referred to as a "known sequence with a function". Other "known" ESTs exhibit significant match to existing sequences which encode polypeptides of unknown function(s) and are referred to as a "known sequence with no known function".

In one aspect, the invention also provides for known nucleic acid sequences that are chondrocyte enriched or chondrocyte-specific.

EST sequences which have no significant match (less than 65% identity) to any existing sequence in the above cited available databases are categorized as novel ESTs. These novel ESTs are considered chondrocyte-specific since they are not matched to any other genes or ESTs derived from any other tissue. To identify a novel gene from an EST sequence, the EST is preferably at least 150 nucleotides in length. More preferably, the EST encodes at least part of an open reading frame, that is, a nucleic acid sequence between a translation initiation codon and a termination codon, which is potentially translated into a polypeptide sequence.

The invention provides for known and novel nucleic acid sequences that are uniquely expressed in normal, fetal, mild osteoarthritic, moderate osteoarthritic, marked osteoarthritic and severe osteoarthritic cartilage. Tables 13 and 25 show unique known genes and names of the novel sequences identified to date in the fetal, normal, mild osteoarthritic and severe osteoarthritic cDNA libraries using the methods according to the invention.

The invention also provides for known and novel nucleic acid sequences that are upregulated and downregulated in normal, fetal, mild osteoarthritic, moderate osteoarthritic, marked osteoarthritic and severe osteoarthritic cartilage. In one aspect, nucleic acid sequences are enriched in chondrocytes compared to cells which are non-chondrocytes, or in chondrocytes from individuals with osteoarthritis compared to normal individuals, or in chondrocytes from particular stages of development or disease compared to particular other stages of development or disease.

The invention also provides for nucleic acid sequences that are differentially expressed in cartilage from any two of the following developmental and disease stages: fetal, normal, mild osteoarthritic, moderate osteoarthritic, marked osteoarthritic and severe osteoarthritic.

Relative EST frequency is calculated by dividing the number of EST copies for each gene by the total number of ESTs analyzed. The chondrocyte-specific expression of a number of novel ESTs has been confirmed by methods known in the art. Useful methods for measuring gene expression in a tissue include RT PCR, Northern blot, etc.

Novel Nucleic Acid Molecules

Many of the novel nucleic acid molecules of the present invention are differentially expressed between the mild and severe osteoarthritis disease states and are thus useful as potential drug targets or markers for the osteoarthritis disease process. The invention also provides one or more nucleic acid molecules that are differentially expressed in two or more of the following developmental and disease stages: fetal, normal, mild osteoarthritic, moderate osteoarthritic, marked osteoarthritic and severe osteoarthritic. The invention further provides for one or more novel clones that are differentially expressed in two or more of the following developmental and disease stages: fetal, normal, mild osteoarthritic, moderate osteoarthritic, marked osteoarthritic and severe osteoarthritic.

Microarrays

Nucleic Acid Microarrays

Any combination of the nucleic acid sequences generated from any of the chondrocyte cDNA libraries are used for the construction of a microarray. In one embodiment, the microarray is chondrocyte-specific and is anticipated to encompass the entire spectrum of genes that are important in the osteoarthritis disease process. A microarray according to the invention preferably comprises between 10 and 20,000 nucleic acid members, and more preferably comprises at least 5000 nucleic acid members. The nucleic acid members are known or novel nucleic acid sequences described herein, or any combination thereof. A microarray according to the invention is used to confirm differential gene expression profiles of genes that are specifically expressed at different cartilage development and osteoarthritis disease stages.

The invention also provides for a microarray comprising genes that are differentially expressed between normal and mild osteoarthritis patients to allow for the identification of early risk factors for osteoarthritis development. The invention also provides for a microarray for osteoarthritis diagnosis comprising one or more nucleic acid sequences that are differentially expressed between a normal individual and a patient diagnosed with mild, moderate, marked or severe osteoarthritis. Such arrays also may be used for prognostic methods to monitor a patient's response to therapy. Preferably, an array for osteoarthritis diagnosis comprises 10-20,000 nucleic acid members and more preferably 50-15,000 nucleic acid members. In one embodiment, the above microarrays are used to identify a therapeutic agent that modulates the anabolic activity of a chondrocyte or changes (e.g., increases or decreases) the level of expression of at least one nucleic acid sequence that is differentially expressed in a chondrocyte derived from any of the following chondrocyte disease or developmental stages: fetal, normal, mild osteoarthritic, moderate osteoarthritic, marked osteoarthritic and severe osteoarthritic.

The target nucleic acid samples that are hybridized to and analyzed with a microarray of the invention are preferably from human cartilage, blood or synovial fluid. A limitation for this procedure lies in the amount of RNA available for use as a target nucleic acid sample. Preferably, at least 1 microgram of total RNA is obtained for use according to this invention. This is advantageous because the amount of RNA in synovial fluid and in many cartilage biopsy samples is very minimal.

Construction of a Microarray

In one aspect, cDNAs generated from human cartilage cDNA libraries are arrayed on a microarray. Preferably, a microarray according to the invention comprises chondrocyte enriched or chondrocyte-specific genes and includes the whole spectrum of genes that are important in the osteoarthritis disease process.

The EST frequency analysis in Table 13 (and portions thereof shown in Tables 27 and 28) shows the differential gene expression profiles for known genes. Table 13 lists the unique known genes (5,807) identified in the four cDNA libraries to date according to one embodiment of the invention. Table 27, lists genes that have been identified through EST frequency analysis as being differentially expressed between fetal and normal cDNA libraries according to one embodiment of the invention. Table 28 lists genes that have been identified through EST frequency analysis as being differentially expressed between mild and severe osteoarthritis cDNA libraries according to one embodiment of the invention. Microarrays according to the invention may be used to confirm these profiles and may also be used to show differential expression profiles between different developmental stages and osteoarthritis disease states for novel EST sequences. These novel EST sequences may be further characterized by cluster and alignment analyses to determine how many unique genes are represented by the novel EST sequences. The novel unique genes identified may provide a basis for identifying key markers in osteoarthritis disease progression and treatment.

In the subject methods, an array of nucleic acid members stably associated with the surface of a substantially solid support is contacted with a sample comprising target nucleic acids under hybridization conditions sufficient to produce a hybridization pattern of complementary nucleic acid members/target complexes in which one or more complementary nucleic acid members at unique positions on the array specifically hybridize to target nucleic acids. The identity of target nucleic acids which hybridize can be determined with reference to location of nucleic acid members on the array.

The nucleic acid members may be produced using established techniques such as polymerase chain reaction (PCR) and reverse transcription (RT). These methods are similar to those currently known in the art (see e.g., *PCR Strategies*, Michael A. Innis (Editor), et al. (1995) and *PCR: Introduction to Biotechniques Series*, C. R. Newton, A. Graham (1997)).

Amplified nucleic acids are purified by methods well known in the art (e.g., column purification or alcohol precipitation). A nucleic acid is considered pure when it has been isolated so as to be substantially free of primers and incomplete products produced during the synthesis of the desired nucleic acid. Preferably, a purified nucleic acid will also be substantially free of contaminants which may hinder or otherwise mask the specific binding activity of the molecule.

A microarray according to the invention comprises a plurality of unique nucleic acids attached to one surface of a solid support at a density exceeding 20 different nucleic acids/cm$^2$, wherein each of the nucleic acids is attached to the surface of the solid support in a non-identical pre-selected region. Each associated sample on the array comprises a nucleic acid composition, of known identity, usually of known sequence, as described in greater detail below. Any conceivable substrate may be employed in the invention.

In one embodiment, the nucleic acid attached to the surface of the solid support is DNA. In a preferred embodiment, the nucleic acid attached to the surface of the solid support is cDNA or RNA. In another preferred embodiment, the nucleic acid attached to the surface of the solid support is cDNA synthesized by polymerase chain reaction (PCR). Preferably, a nucleic acid member in the array, according to the invention, is at least 50 nucleotides in length. In one embodiment, a nucleic acid member is at least 150 nucleotides in length. Preferably, a nucleic acid member is less than 1000 nucleotides in length. More preferably, a nucleic acid member is less than 500 nucleotides in length. In one embodiment, an array comprises at least 10 different nucleic acids attached to one surface of the solid support. In another embodiment, the array comprises at least 100 different nucleic acids attached to one surface of the solid support. In yet another embodiment, the array comprises at least 10,000 different nucleic acids attached to one surface of the solid support. In yet another embodiment, the array comprises at least 15,000 different nucleic acids attached to one surface of the solid support.

In the arrays of the invention, the nucleic acid compositions are stably associated with the surface of a solid support, where the support may be a flexible or rigid solid support. By "stably associated" is meant that each nucleic acid member maintains a unique position relative to the solid support under hybridization and washing conditions. As such, the samples are non-covalently or covalently stably associated with the support surface. Examples of non-covalent association include non-specific adsorption, binding based on electrostatic interactions (e.g., ion pair interactions), hydrophobic interactions, hydrogen bonding interactions, specific binding through a specific binding pair member covalently attached to the support surface, and the like. Examples of covalent binding include covalent bonds formed between the nucleic acids and a functional group present on the surface of the rigid support (e.g., —OH), where the functional group may be naturally occurring or present as a member of an introduced linking group, as described in greater detail below The amount of nucleic acid present in each composition will be sufficient to provide for adequate hybridization and detection of target nucleic acid sequences during the assay in which the array is employed. Generally, the amount of each nucleic acid member stably associated with the solid support of the array is at least about 0.001 ng, preferably at least about 0.02 ng and more preferably at least about 0.05 ng, where the amount may be as high as 1000 ng or higher, but will usually not exceed about 20 ng. Where the nucleic acid member is "spotted" onto the solid support in a spot comprising an overall circular dimension, the diameter of the "spot" will generally range from about 10 to 5,000 μm, usually from about 20 to 2,000 μm and more usually from about 100 to 200 μm.

Control nucleic acid members may be present on the array including nucleic acid members comprising oligonucleotides or nucleic acids corresponding to genomic DNA, housekeeping genes, vector sequences, plant nucleic acid sequence, negative and positive control genes, and the like. Control nucleic acid members are calibrating or control genes whose function is not to tell whether a particular "key" gene of interest is expressed, but rather to provide other useful information, such as background or basal level of expression.

Other control nucleic acids are spotted on the array and used as target expression control nucleic acids and mismatch control nucleotides to monitor non-specific binding or cross-hybridization to a nucleic acid in the sample other than the target to which the probe is directed. Mismatch probes thus indicate whether a hybridization is specific or not. For example, if the target is present, the perfectly matched probes should be consistently brighter than the mismatched probes. In addition, if all control mismatches are present, the mismatch probes are used to detect a mutation.

Solid Substrate

An array according to the invention comprises either a flexible or rigid substrate. A flexible substrate is capable of being bent, folded or similarly manipulated without breakage. Examples of solid materials which are flexible solid supports with respect to the present invention include membranes, e.g., nylon, flexible plastic films, and the like. By "rigid" is meant that the support is solid and does not readily bend, i.e., the support is not flexible. As such, the rigid substrates of the subject arrays are sufficient to provide physical support and structure to the associated nucleic acids present thereon under the assay conditions in which the array is employed, particularly under high throughput handling conditions.

The substrate may be biological, non-biological, organic, inorganic, or a combination of any of these, existing as particles, strands, precipitates, gels, sheets, tubing, spheres, beads, containers, capillaries, pads, slices, films, plates, slides, chips, etc. The substrate may have any convenient shape, such as a disc, square, sphere, circle, etc. The substrate is preferably flat or planar but may take on a variety of alternative surface configurations. The substrate may be a polymerized Langmuir Blodgett film, functionalized glass, Si, Ge, GaAs, GaP, $SiO_2$, $SIN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those of skill in the art upon review of this disclosure.

In a preferred embodiment the substrate is flat glass or single-crystal silicon. According to some embodiments, the surface of the substrate is etched using well-known techniques to provide for desired surface features. For example, by way of formation of trenches, v-grooves, mesa structures, or the like, the synthesis regions may be more closely placed within the focus point of impinging light, be provided with reflective "mirror" structures for maximization of light collection from fluorescent sources, etc.

Surfaces on the solid substrate will usually, though not always, be composed of the same material as the substrate. Alternatively, the surface may be composed of any of a wide variety of materials, for example, polymers, plastics, resins, polysaccharides, silica or silica-based materials, carbon, metals, inorganic glasses, membranes, or any of the above-listed substrate materials. In some embodiments the surface may provide for the use of caged binding members which are attached firmly to the surface of the substrate. Preferably, the surface will contain reactive groups, which are carboxyl, amino, hydroxyl, or the like. Most preferably, the surface will be optically transparent and will have surface Si—OH functionalities, such as are found on silica surfaces.

The surface of the substrate is preferably provided with a layer of linker molecules, although it will be understood that the linker molecules are not required elements of the invention. The linker molecules are preferably of sufficient length to permit nucleic acids of the invention and on a substrate to hybridize to other nucleic acid molecules and to interact freely with molecules exposed to the substrate.

Often, the substrate is a silicon or glass surface, (poly) tetrafluoroethylene, (poly)vinylidendifluoride, polystyrene, polycarbonate, a charged membrane, such as nylon 66 or nitrocellulose, or combinations thereof. In a preferred embodiment, the solid support is glass. Preferably, at least one surface of the substrate will be substantially flat. Preferably, the surface of the solid support will contain reactive groups, including, but not limited to, carboxyl, amino, hydroxyl, thiol, or the like. In one embodiment, the surface is optically transparent. In a preferred embodiment, the substrate is a poly-lysine coated slide or Gamma amino propyl silane-coated Corning Microarray Technology-GAPS or CMT-GAP2 coated slides.

Any solid support to which a nucleic acid member may be attached may be used in the invention. Examples of suitable solid support materials include, but are not limited to, silicates such as glass and silica gel, cellulose and nitrocellulose papers, nylon, polystyrene, polymethacrylate, latex, rubber, and fluorocarbon resins such as TEFLON™.

The solid support material may be used in a wide variety of shapes including, but not limited to slides and beads. Slides provide several functional advantages and thus are a preferred form of solid support. Due to their flat surface, probe and hybridization reagents are minimized using glass slides. Slides also enable the targeted application of reagents, are easy to keep at a constant temperature, are easy to wash and facilitate the direct visualization of RNA and/or DNA immobilized on the solid support. Removal of RNA and/or DNA immobilized on the solid support is also facilitated using slides.

The particular material selected as the solid support is not essential to the invention, as long as it provides the described function. Normally, those who make or use the invention will select the best commercially available material based upon the economics of cost and availability, the expected application requirements of the final product, and the demands of the overall manufacturing process.

Spotting Method

In one aspect, the invention provides for arrays where each nucleic acid member comprising the array is spotted onto a solid support.

Preferably, spotting is carried out as follows. PCR products (~40 ul) of cDNA clones from osteoarthritis, fetal or normal cartilage cDNA libraries, in the same 96-well tubes used for amplification, are precipitated with 4 ul (1/10 volume) of 3M sodium acetate (pH 5.2) and 100 ul (2.5 volumes) of ethanol and stored overnight at −20° C. They are then centrifuged at 3,300 rpm at 4° C. for 1 hour. The obtained pellets are washed with 50 ul ice-cold 70% ethanol and centrifuged again for 30 minutes. The pellets are then air-dried and resuspended well in 20 ul 3×SSC or in 50% dimethylsulfoxide (DMSO) overnight. The samples are then spotted, either singly or in duplicate, onto slides using a robotic GMS 417 or 427 arrayer (Affymetrix, Ca).

The boundaries of the spots on the microarray may be marked with a diamond scriber (as the spots become invisible after post-processing). The arrays are rehydrated by suspending the slides over a dish of warm particle free ddH$_2$0 for approximately one minute (the spots will swell slightly but will not run into each other) and snap-dried on a 70-80° C. inverted heating block for 3 seconds. Nucleic acid is then UV crosslinked to the slide (Stratagene, Stratalinker, 65 mJ—set display to "650" which is 650×100 uJ) or the array is baked at 80 C for two to four hours prior to hybridization. The arrays are placed in a slide rack. An empty slide chamber is prepared and filled with the following solution: 3.0 grams of succinic anhydride (Aldrich) was dissolved in 189 ml of 1-methyl-2-pyrrolidinone (rapid addition of reagent is crucial); immediately after the last flake of succinic anhydride is dissolved, ~21.0 ml of 0.2 M sodium borate is mixed in and the solution is poured into the slide chamber. The slide rack is plunged rapidly and evenly in the slide chamber and vigorously shaken up and down for a few seconds, making sure the slides never leave the solution, and then mixed on an orbital shaker for 15-20 minutes. The slide rack is then gently plunged in 95° C. ddH$_2$0 for 2 minutes, followed by plunging five times in 95% ethanol. The slides are then air dried by allowing excess ethanol to drip onto paper towels. The arrays are stored in the slide box at room temperature until use.

Numerous methods may be used for attachment of the nucleic acid members of the invention to the substrate (a process referred to as "spotting"). For example, nucleic acids are attached using the techniques of, for example U.S. Pat. No. 5,807,522, which is incorporated herein by reference, for teaching methods of polymer attachment.

Alternatively, spotting may be carried out using contact printing technology as is known in the art.

Kits

The invention provides for kits for performing expression assays using the arrays of the present invention. Such kits according to the subject invention will at least comprise the arrays of the invention having associated nucleic acid members and packaging means therefore. The kits may further comprise one or more additional reagents employed in the various methods, such as: 1) primers for generating test nucleic acids; 2) dNTPs and/or rNTPs (either premixed or separate), optionally with one or more uniquely labeled dNTPs and/or rNTPs (e.g., biotinylated or Cy3 or Cy5 tagged dNTPs); 3) post synthesis labeling reagents, such as chemically active derivatives of fluorescent dyes; 4) enzymes, such as reverse transcriptases, DNA polymerases, and the like; 5) various buffer mediums, e.g., hybridization and washing buffers; 6) labeled probe purification reagents and components, like spin columns, etc.; and 7) signal generation and detection reagents, e.g., streptavidin-alkaline phosphatase conjugate, chemifluorescent or chemiluminescent substrate, and the like.

Use of a Microarray

Nucleic acid arrays according to the invention can be used in high throughput techniques that can assay a large number of nucleic acids in a sample comprising one or more target nucleic acid sequences. The arrays of the subject invention find use in a variety of applications, including gene expression analysis, diagnosis of osteoarthritis and prognosis of osteoarthritis, monitoring a patient's response to therapy, drug screening, and the like.

In one aspect, the arrays of the invention are used in, among other applications, differential gene expression assays. For example, arrays are useful in the differential expression analysis of: (a) diseased osteoarthritis and normal tissue; (b) tissues representing different stages of osteoarthritis; (c) developing cartilage (e.g., fetal cartilage); (d) chondrocyte responses to external or internal stimuli; (e) cartilage/chondrocyte response to treatment; (f) cartilage tissue engineering; (g) pharmacogenomics; and the like. The arrays are also useful in broad scale expression screening for drug discovery and research, such as the effect of a particular active agent on the expression pattern of genes in a particular cell, where such information is used to reveal drug efficacy and toxicity, environmental monitoring, disease research and the like. For example, high expression of a particular nucleic acid sequence in an osteoarthritis sample (mild, moderate, marked, or severe), which is not observed in a corresponding normal cell, can indicate an osteoarthritis-specific gene product.

For example, arrays useful in the invention can include sequences which demonstrate increased or decreased expression in patient's having osteoarthritis as compared to normal individuals. More particularly, an array useful in accordance with the invention include sequences which demonstrate increased or decreased expression in patients identified as having a particular stage of progression of the disease, for example mild osteoarthritis but not demonstrating increased or decreased expression in another stage of progression of the disease, for example severe osteoarthritis.

Arrays can be made using at least one, more preferably a majority of these sequences, as a means of diagnosing osteoarthritis, or for purposes of monitoring efficacy of treatment and of osteoarthritis.

For example an array of the invention can be used to diagnose an individual having osteoarthritis by hybridizing a sample complementary to a patient's RNA to an array comprising sequences identified as having increased or decreased expression, and comparing the level of intensity of hybridization as between this sample and a sample complementary to RNA isolated from normal individuals to a similar or identical second array.

Similarly, an array of the invention can be used to monitor the efficacy of treatment in patients who have osteoarthritis by hybridizing a sample complementary to a patient's RNA, wherein the patient has been treated so as to reduce the progression of osteoarthritis, and determining the intensity of the hybridization as compared with the intensity of hybridization of a standard sample hybridized to another array of the invention.

Additionally, an array of the invention can be utilized to identify an agent that increases or decreases the expression of a polynucleotide sequence of the invention by incubating a chondrocyte derived from a normal individual with a candidate agent, wherein said chondrocyte is isolated from a cartilage sample obtained from said normal individual less than 14 hours post-mortem; hybridizing a sample complementary to a patient's RNA to an array of the invention, and hybridizing a sample useful as a standard to another array of the invention and comparing the intensity of expression between corresponding unique positions on the arrays.

The choice of a standard sample would be well understood by a person skilled in the art, and would include a sample complementary to RNA isolated from one or more normal individuals, wherein a normal individual is an individual not suffering from osteoarthritis. A standard sample would include a sample complementary to RNA isolated from chondrocytes, or from blood, or from synovial fluid.

Target Preparation

The targets for the microarrays according to the invention are preferably derived from human cartilage, blood or synovial fluid.

A target nucleic acid is capable of binding to a nucleic acid probe or nucleic acid member of complementary, sequence through one or more types of chemical bonds, usually through complementary base pairing, usually through hydrogen bond formation.

As used herein, a "nucleic acid derived from an mRNA transcript: or a "nucleic acid corresponding to an mRNA" refers to a nucleic acid for which synthesis of the mRNA transcript or a sub-sequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from or correspond to the mRNA transcript and detection of such derived or corresponding products is indicative of or proportional to the presence and/or abundance of the original transcript in a sample. Thus, suitable target nucleic acid samples include, but are not limited to, mRNA transcripts of a gene or genes, cDNA reverse transcribed from the mRNA, cRNA transcribed from the cDNA, DNA amplified from a gene or genes, RNA transcribed from amplified DNA, and the like. The nucleic acid targets used herein are preferably derived from human cartilage, blood or synovial fluid. Preferably, the targets are nucleic acids derived from human cartilage, blood or synovial fluid extracts. Nucleic acids can be single- or double-stranded DNA, RNA, or DNA-RNA hybrids synthesized from human cartilage, blood or synovial fluid mRNA extracts using methods known in the art, for example, reverse transcription or PCR.

In the simplest embodiment, such a nucleic acid target comprises total mRNA or a nucleic acid sample corresponding to mRNA (e.g., cDNA) isolated from cartilage, blood, or synovial fluid samples. In another embodiment, total mRNA is isolated from a given sample using, for example, an acid guanidinium-phenol-chloroform extraction method and polyA+ mRNA is isolated by oligo dT column chromatography or by using (dT)n magnetic beads (see, e.g., Sambrook et al., *Molecular Cloning: A Laboratory Manual* (2nd ed.), Vols. 1-3, Cold Spring Harbor Laboratory, (1989), or Current Protocols in Molecular Biology, F. Ausubel et al., ed. Greene Publishing and Wiley-Interscience, New York (1987). In a preferred embodiment, total RNA is extracted using TRIzol® reagent (GIBCO/BRL, Invitrogen Life Technologies, Cat. No. 15596). Purity and integrity of RNA is assessed by absorbance at 260/280 nm and agarose gel electrophoresis followed by inspection under ultraviolet light.

In some embodiments, it is desirable to amplify the target nucleic acid sample prior to hybridization, for example, when synovial fluid is used. One of skill in the art will appreciate that whatever amplification method is used, if a quantitative result is desired, care must be taken to use a method that maintains or controls for the relative frequencies of the amplified nucleic acids. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid. Detailed protocols for quantitative PCR are provided in *PCR Protocols, A Guide to Methods and Applications*, Innis et al., Academic Press, Inc. N.Y., (1990).

Other suitable amplification methods include, but are not limited to polymerase chain reaction (PCR) (Innis, et al., *PCR Protocols. A Guide to Methods and Application*. Academic Press, Inc. San Diego, (1990)), ligase chain reaction (LCR) (see Wu and Wallace, 1989, *Genomics,* 4:560; Landegren, et al., 1988, *Science,* 241:1077 and Barringer, et al., 1990, *Gene,* 89:117, transcription amplification (Kwoh, et al., 1989, *Proc. Natl. Acad. Sci. USA,* 86: 1173), and self-sustained sequence replication (Guatelli, et al., 1990, *Proc. Nat. Acad. Sci. USA,* 87: 1874).

In a particularly preferred embodiment, the target nucleic acid sample mRNA is reverse transcribed with a reverse transcriptase and a primer consisting of oligo dT and a sequence encoding the phage T7 promoter to provide single-stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro transcription are well known to those of skill in the art (see, e.g., Sambrook, supra.) and this particular method is described in detail by Van Gelder, et al., 1990, *Proc. Natl. Acad. Sci. USA,* 87: 1663-1667 who demonstrate that in vitro amplification according to this method preserves the relative frequencies of the various RNA transcripts. Moreover, Eberwine et al. *Proc. Natl. Acad. Sci. USA,* 89: 3010-3014 provide a protocol that uses two rounds of amplification via in vitro transcription to achieve greater than $10^6$ fold amplification of the original starting material thereby permitting expression monitoring even where biological samples are limited.

Labeling of Target or Nucleic Acid Probe

Either the target or the probe can be labeled.

Any analytically detectable marker that is attached to or incorporated into a molecule may be used in the invention. An analytically detectable marker refers to any molecule, moiety or atom which is analytically detected and quantified.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, the entireties of which are incorporated by reference herein.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example, nick translation or end-labeling (e.g. with a labeled RNA) by kinasing of the nucleic acid and subsequent attachment (ligation) of a nucleic acid linker joining the sample nucleic acid to a label (e.g., a fluorophore).

In a preferred embodiment, the fluorescent modifications are by cyanine dyes e.g. Cy-3/Cy-5 dUTP, Cy-3/Cy-5 dCTP (Amersham Pharmacia) or alexa dyes (Khan, et al., 1998, *Cancer Res.* 58:5009-5013).

In a preferred embodiment, the two target samples used for comparison are labeled with different fluorescent dyes which produce distinguishable detection signals, for example, targets made from normal cartilage are labeled with Cy5 and targets made from mild osteoarthritis cartilage are labeled with Cy3. The differently labeled target samples are hybridized to the same microarray simultaneously. In a preferred embodiment, the labeled targets are purified using methods known in the art, e.g., by ethanol purification or column purification.

In a preferred embodiment, the target will include one or more control molecules which hybridize to control probes on the microarray to normalize signals generated from the microarray. Preferably, labeled normalization targets are nucleic acid sequences that are perfectly complementary to control oligonucleotides that are spotted onto the microarray as described above. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes, thereby normalizing the measurements.

Preferred normalization targets are selected to reflect the average length of the other targets present in the sample, however, they are selected to cover a range of lengths. The normalization control(s) also can be selected to reflect the (average) base composition of the other probes in the array, however, in a preferred embodiment, only one or a few normalization probes are used and they are selected such that they hybridize well (i.e., have no secondary structure and do not self hybridize) and do not match any target molecules.

Normalization probes are localized at any position in the array or at multiple positions throughout the array to control for spatial variation in hybridization efficiency. In a preferred embodiment, normalization controls are located at the corners or edges of the array as well as in the middle.

Hybridization Conditions

Nucleic acid hybridization involves providing a denatured probe or target nucleic acid member and target nucleic acid under conditions where the probe or target nucleic acid member and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

The invention provides for hybridization conditions comprising the Dig hybridization mix (Boehringer); or formamide-based hybridization solutions, for example as described in Ausubel et al., supra and Sambrook et al. supra.

Methods of optimizing hybridization conditions are well known to those of skill in the art (see, e.g., *Laboratory Techniques in Biochemistry and Molecular Biology*, Vol. 24: *Hybridization With Nucleic acid Probes*, P. Tijssen, ed. Elsevier, N.Y., (1993)).

Following hybridization, non-hybridized labeled or unlabeled nucleic acid is removed from the support surface, conveniently by washing, thereby generating a pattern of hybridized target nucleic acid on the substrate surface. A variety of wash solutions are known to those of skill in the art and may be used. The resultant hybridization patterns of labeled, hybridized oligonucleotides and/or nucleic acids may be visualized or detected in a variety of ways, with the particular manner of detection being chosen based on the particular label of the test nucleic acid, where representative detection means include scintillation counting, autoradiography, fluorescence measurement, calorimetric measurement, light emission measurement and the like.

Image Acquisition and Data Analysis

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding to the signal emitted by a known number of end labeled target nucleic acids to obtain a count or absolute value of the copy number of each end-labeled target that is hybridized to a particular spot on the array in the hybridization pattern.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e., data deviating from a predetermined statistical distribution, and calculating the relative binding affinity of the test nucleic acids from the remaining data. The resulting data is displayed as an image with the intensity in each region varying according to the binding affinity between associated oligonucleotides and/or nucleic acids and the test nucleic acids.

The following detection protocol is used for the simultaneous analysis of two cartilage samples to be compared, where each sample is labeled with a different fluorescent dye.

Each element of the microarray is scanned for the first fluorescent color. The intensity of the fluorescence at each array element is proportional to the expression level of that gene in the sample.

The scanning operation is repeated for the second fluorescent label. The ratio of the two fluorescent intensities provides a highly accurate and quantitative measurement of the relative gene expression level in the two tissue samples.

In a preferred embodiment, fluorescence intensities of immobilized target nucleic acid sequences were determined from images taken with a custom confocal microscope equipped with laser excitation sources and interference filters appropriate for the Cy3 and Cy5 fluors. Separate scans were taken for each fluor at a resolution of 225 $\mu m^2$ per pixel and 65,536 gray levels. Image segmentation to identify areas of hybridization, normalization of the intensities between the two fluor images, and calculation of the normalized mean fluorescent values at each target are as described (Khan, et al., 1998, *Cancer Res.* 58:5009-5013. Chen, et al., 1997, *Biomed. Optics* 2:364-374). Normalization between the images is used to adjust for the different efficiencies in labeling and detection with the two different fluors. This is achieved by equilibrating to a value of one the signal intensity ratio of a set of internal control genes spotted on the array.

In another preferred embodiment, the array is scanned in the Cy 3 and Cy5 channels and stored as separate 16-bit TIFF images. The images are incorporated and analysed using software which includes a gridding process to capture the hybridization intensity data from each spot on the array. The fluorescence intensity and background-subtracted hybridization intensity of each spot is collected and a ratio of measured mean intensities of Cy5 to Cy3 is calculated. A liner regression approach is used for normalization and assumes that a scatter plot of the measured Cy5 versus Cy3 intensities should have a scope of one. The average of the ratios is calculated and used to rescale the data and adjust the slope to one. A post-normalization cutoff of greater than 1.0 fold up- or down-regulation is used to identify differentially expressed genes.

Following detection or visualization, the hybridization pattern is used to determine quantitative information about the genetic profile of the labeled target nucleic acid sample that was contacted with the array to generate the hybridization pattern, as well as the physiological source from which the labeled target nucleic acid sample was derived. By "genetic profile" is meant information regarding the types of nucleic acids present in the sample, e.g., such as the types of genes to which they are complementary, and/or the copy number of each particular nucleic acid in the sample. From this data, one can also derive information about the physiological source from which the target nucleic acid sample was derived, such as the types of genes expressed in the tissue or cell which is the physiological source of the target, as well as the levels of expression of each gene, particularly in quantitative terms.

Where one uses the subject methods to compare target nucleic acids from two or more physiological sources, the hybridization patterns may be compared to identify differences between the patterns. Where arrays in which each of the different nucleic acid members corresponds to a known gene are employed, any discrepancies are related to a differential expression of a particular gene in the physiological sources being compared. Thus, the subject methods find use in differential gene expression assays, where one may use the subject methods in the differential expression analysis of: (a) diseased vs. normal tissue, e.g., osteoarthritic and normal tissue, (b) tissue derived from different stages of osteoarthritis; and the like.

In a particularly preferred embodiment, where it is desired to quantify the transcription level (and thereby expression) of one or more nucleic acid sequences in a sample, the target nucleic acid sample is one in which the concentration of the mRNA transcript(s) of the gene or genes, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear and still provide meaningful results. Thus, for example, an assay where a 5 fold difference in concentration of the target mRNA results in a 3- to 6-fold difference in hybridization intensity is sufficient for most purposes. Where more precise quantification is required, appropriate controls are run to correct for variations introduced in sample preparation and hybridization as described herein. In addition, serial dilutions of "standard" target mRNAs are used to prepare calibration curves according to methods well known to those of skill in the art. Of course, where simple detection of the presence or absence of a transcript is desired, no elaborate control or calibration is required.

For example, if a microarray nucleic acid member is not labeled after hybridization, this indicates that the gene comprising that nucleic acid member is not expressed in either sample. If a nucleic acid member is labeled with a single color, it indicates that a labeled gene was expressed only in one sample. The labeling of a nucleic acid member comprising an array with both colors indicates that the gene was expressed in both samples. Even genes expressed once per cell are detected (1 part in 100,000 sensitivity). A difference in expression intensity in the two samples being compared is indicative of differential expression, the ratio of the intensity in the two samples being not equal to 1.0, preferably less than 0.7 or greater than 1.2, more preferably less than 0.5 or greater than 1.5.

Many human genes are expressed at different levels in cartilage of different developmental (fetal vs. mature) or disease states. In some cases, a gene is not expressed at all in some developmental or disease states, and at high levels in others. Differential analysis of chondrocyte gene expression in differing cartilage states using an EST-based approach is used to identify genes that may play important roles in osteoarthritis pathogenesis and cartilage repair. The advantage of this method is that it can provide gene expression information on a larger scale than other methods. The cDNA clones generated by this approach is useful for future functional studies of certain genes. This type of genomic-based approach can provide important novel insights into our understanding of the osteoarthritis disease process and provide for novel diagnostic, prognostic and therapeutic approaches.

Diagnostic or Prognostic Tests

The invention also provides for diagnostic tests for detecting osteoarthritis. The invention also provides for prognostic tests for monitoring a patient's response to therapy.

According to the method of the invention, mild, moderate, marked or severe osteoarthritis is detected by obtaining a cartilage sample from a patient. In alternative embodiments, a blood or synovial fluid sample is obtained from a patient. A sample comprising nucleic acid corresponding to RNA (i.e., RNA or cDNA) is prepared from the patient cartilage (or blood or synovial fluid) sample. The sample comprising nucleic acid corresponding to RNA is hybridized to an array comprising a solid substrate and a plurality of nucleic acid members, where at least one member is differentially expressed in cartilage isolated from a patient diagnosed with mild, moderate, marked or severe osteoarthritis, as compared to a "normal individual", according to the invention. According to this diagnostic test, hybridization of the sample comprising nucleic acid corresponding to RNA to one or more nucleic acid members on the array is indicative of disease.

A patient response to therapy is monitored by using a prognostic test according to the invention. In one aspect, a prognostic test according to the invention comprises obtaining a cartilage sample from a patient prior to treatment, during the course of treatment and after treatment. Preferably, the patient is treated for at least 12 hours before a sample is taken. In alternative embodiments, blood or synovial fluid samples are obtained from a patient prior to treatment, during the course of treatment and after treatment. A sample comprising nucleic acid corresponding to RNA (i.e., RNA or cDNA) is prepared from the patient cartilage (or blood or synovial fluid) samples. The samples comprising nucleic acid corresponding to RNA are hybridized to an array comprising a solid substrate and a plurality of nucleic acid members, wherein at least one member is differentially expressed in cartilage isolated from a patient diagnosed with mild, moderate, marked or severe osteoarthritis, as compared to a normal individual, according to the invention. Arrays are selected in accordance with the diagnostic state of the patient whose treatment is being monitored. According to this prognostic test, differential hybridization of the samples comprising nucleic acid corresponding to RNA isolated prior to and after treatment to one or more nucleic acid members on the array is indicative of an effective treatment. Preferably, gene expression profiles in patients being treated changes to resemble more closely gene expression profiles in patients with less severe forms of the disease or more preferably more closely resembles gene expression profiles in normal patients. The extent of change in a gene expression profile can be further correlated with various therapeutic endpoints such as a decrease in the severity and/or occurrence of one or more symptoms associated with the disease.

Therapeutic Agents

A useful therapeutic agent according to the invention can increase or decrease the anabolic and/or the catabolic activity of a chondrocyte. Preferably, a therapeutic agent can increase or decrease the anabolic and/or catabolic activity of a chondrocyte by greater than 1.0-fold, more preferably, 1.5-5-fold, and most preferably, 5-100-fold, as compared to an untreated chondrocyte.

In one embodiment, a therapeutic agent changes (e.g., increases or decreases) the level of expression of at least one nucleic acid sequence that is differentially expressed in a chondrocyte derived from any of the following chondrocyte disease or developmental stages: fetal, normal, mild osteoarthritic, moderate osteoarthritic, marked osteoarthritic and severe osteoarthritic. Preferably, a therapeutic agent causes a change in the level of expression of a nucleic acid sequence or increase or decrease in the expression of a nucleic acid sequence that is differentially expressed in a chondrocyte derived from any of the following chondrocyte disease or developmental stages: fetal, normal, mild osteoarthritic, moderate osteoarthritic, marked osteoarthritic and severe osteoarthritic, where the change is greater than 1.0-fold, more preferably 1.5-5-fold, and most preferably 5-100-fold, more or less than the level of expression in the absence of a candidate therapeutic agent.

In another embodiment, a therapeutic agent according to the invention can ameliorate at least one of the symptoms and/or changes associated with osteoarthritis including cartilage degeneration, or pain, swelling, weakness and/or loss of functional ability in the afflicted joints, associated with cartilage degeneration.

The candidate therapeutic agent may be a synthetic compound, or a mixture of compounds, or may be a natural product (e.g. a plant extract or culture supernatant).

Candidate therapeutic agents or compounds from large libraries of synthetic or natural compounds can be screened. Numerous means are currently used for random and directed synthesis of saccharide, peptide, and nucleic acid-based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and are prepared. Alternatively, libraries of natural compounds in the form of bacterial, fungal, plant and animal extracts are available from e.g., Pan Laboratories (Bothell, Wash.) or MycoSearch (NC), or are readily produceable by methods well known in the art. Additionally, natural and synthetically produced libraries and compounds are readily modified through conventional chemical, physical, and biochemical means.

Useful compounds may be found within numerous chemical classes. Useful compounds may be organic compounds, or small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

A therapeutic agent, according to the invention, can be a gene corresponding to an EST sequence identified from any of the cDNA libraries constructed from cartilage of different development and disease stages.

Each cDNA library revealed a number of EST sequences specific to the particular stage. The ESTs are first characterized according to their putative function (Tables 2-6) and their expression is confirmed by using microarrays, as described herein. Since osteoarthritis is a chronic disease caused by an imbalance between catabolic activity and anabolic activity, that is, an increase in catabolic activity and/or a decrease in anabolic activity, normal- or fetal-specific ESTs may be important in maintaining the normal metabolic function of cartilage so as to maintain a balance between the catabolic activity and the anabolic activity. Therefore, an increased expression of a full length gene sequence corresponding to one or more of these ESTs may restore the anabolic activity in disease cartilage. Therapy involving altered gene expression (e.g., gene therapy, gene disruption, antisense therapy, and the like) is useful according to the invention.

A full-length gene sequence corresponding to one of the normal- or fetal-specific genes is cloned by methods known in the art (e.g., Ausubel et al., John Weley & Sons, Inc., 1997, *Current Protocols in Molecular Biology*). A cloned sequence is transfected into disease chondrocytes isolated from any stage of osteoarthritis (e.g., mild, moderate, marked, and severe). The ability of normal- or fetal-specific genes to complement the anabolic defect in the disease chondrocytes is accessed.

In one embodiment, this is achieved by examining the expression profile of disease chondrocytes transfected with a normal- or fetal-specific gene. A normal- or fetal-specific gene which is capable of restoring the expression profile of disease chondrocytes to more closely resemble that of normal or fetal chondrocytes is a useful candidate for treatment of osteoarthritis.

In another embodiment, the anabolic activity of disease chondrocytes transfected with a normal- or fetal-specific gene is measured as described by Westacott et al. (1996, *Semin Arthritis Rheum,* 25:254-72). A normal- or fetal-specific gene which increases the anabolic activity is useful for treatment of osteoarthritis.

Once a therapeutic gene is defined, the gene sequence is subcloned into a vector suitable for the purpose of gene therapy. Murine leukemia virus (MLV)-based retroviral vectors are one of the most widely, used gene delivery vehicles in gene therapy clinical trials and have been employed in almost 70% of approved protocols (Ali, M. et al., 1994, *Gene Ther.,* 1:367-384; Marshall, 1995, *Science,* 269:1050-1055, 1995). Other useful vectors are also known in the art (e.g., Carter and Samulski, 2000, *Int. J. Mol. Med.* 6:17-27; Lever et al., 1999, *Biochem. Soc. Trans.* 27: 841-7). Methods for gene therapy of human diseases are described in U.S. Pat. Nos. 6,190,907; 6,187,305; 6,140,087; and 6,129,705, for example, the entireties of which are incorporated by reference herein.

Dosage and Administration

Therapeutic agents of the invention are administered to a patient, preferably in a biologically compatible solution or a pharmaceutically acceptable delivery vehicle, by ingestion, injection, inhalation or any number of other methods routine in the art. The dosages administered will vary from patient to patient. A "therapeutically effective dose" is determined, for example, by the level of enhancement of function (e.g., increased or decreased chondrocyte anabolic activity, or an increase or decrease in the expression of at least one nucleic acid sequence that is differentially expressed in a chondrocyte derived from any of the following chondrocyte disease or developmental stages: fetal, normal, mild osteoarthritic, moderate osteoarthritic, marked osteoarthritic or severe osteoarthritic).

A therapeutic agent according to the invention is administered in a single dose. This dosage may be repeated daily, weekly, monthly, yearly, or as considered appropriate by the treating physician.

Pharmaceutical Compositions

The invention provides for compositions comprising a therapeutic agent according to the invention admixed with a physiologically compatible carrier. As used herein, "physiologically compatible carrier" refers to a physiologically acceptable diluent such as water, phosphate buffered saline, or saline, and further may include an adjuvant. Adjuvants such as incomplete Freund's adjuvant, aluminum phosphate, aluminum hydroxide, or alum are materials well known in the art.

The invention also provides for pharmaceutical compositions. In addition to the active ingredients, these pharmaceutical compositions may contain suitable pharmaceutically acceptable carrier preparations which is used pharmaceutically.

Pharmaceutical compositions for oral administration are formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use are obtained through a combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which are used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For nasal administration, penetrants appropriate to the particular barrier to be permeated are used in the formulation. Such penetrants are generally known in the art.

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

The pharmaceutical composition may be provided as a salt and are formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

After pharmaceutical compositions comprising a therapeutic agent of the invention formulated in a acceptable carrier have been prepared, they are placed in an appropriate container and labeled for treatment of an indicated condition with information including amount, frequency and method of administration.

Efficacy of Osteoarthritis Therapy Using Defined Therapeutic Agents

The efficacy of the therapy using any of the therapeutic agents according to the invention is determined by a medical practitioner. This determination may be related to alleviating osteoarthritis symptoms such as pain, swelling, weakness and loss of functional ability in the afflicted joint(s), and/or criteria for osteoarthritis diagnosis and staging described in Marshall (1996, supra).

The above disclosure generally describes the present invention. A more complete understanding can be obtained by reference to the following specific examples, which are provided herein for purposes of illustration only and are not intended to limit the scope of the invention.

EXAMPLES

The examples below are non-limiting and are merely representative of various aspects and features of the present invention

Example 1

RNA Extraction And Fetal cDNA Library Construction

A cDNA library was prepared from fetal cartilage. ESTs were obtained from the cDNA library and evaluated to create one or more gene expression profiles for fetal chondrocytes.

Human fetal femoral cartilage RNA was extracted from pooled specimens of aborted fetuses (8-12 weeks). Samples were finely powdered under liquid nitrogen, and total RNA was extracted using TRIzol® reagent (GIBCO/BRL). Purity and integrity of RNA was assessed by absorbance at 260/280 nm and agarose gel electrophoresis. The poly (A)+ RNA fraction was isolated by oligo-dT cellulose chromatography (Pharmacia), and 3-5 ug poly (A)+ RNA was used to construct a cDNA library in the λ ZAP Express vector (Stratagene). First-strand cDNA was synthesized with an Xho I-oligo (dT) adapter-primer in the presence of 5'-methyl dCTP. After second-strand synthesis and ligation of EcoRI adapters, the cDNA was digested with Xho I, resulting in cDNA flanked by EcoRI sites at the 5'-ends and Xho I sites at the 3'-ends. Digested cDNAs were size-fractionated in Sephacryl S-500 spin columns (Stratagene), then ligated into the λ ZAP Express vector predigested with EcoRI and Xho I. The resulting DNA/cDNA concatomers were packaged using Gigapack Gold packaging extracts. After titration, aliquots of primary packaging mix were stored in 7% DMSO at −80° C. as primary library stocks, and the rest were amplified to establish stable library stocks.

Large-Scale Sequencing of cDNA Inserts

From the amplified λ ZAP Express library, phage plaques were plated at a density of 200-500 pfu/150 mm plate onto Escherichia coli XL1-blue MRF' lawn with IPTG/X-gal for color selection. Plaques were picked into 75 ul suspension media buffer (100 mM NaCl, 10 mM MgSO$_4$, 1 mM Tris, pH7.5, 0.02% gelatin). Phage elutes (5 ul) were used for PCR reactions (50 ul total volume) with 125 umol/L of each dNTP (Pharmacia), 10 pmol each of modified T3 (5'-GC-CAAGCTCGAAATTAACCCTCACTAAAG GG-3') (SEQ ID NO: 58,993) and T7 (5'-CCAGTGAATTGTAATAC-GACTCACTATAGGGCG-3') (SEQ ID NO: 58,994) primers, and 2 U of Taq DNA polymerase (Pharmacia). Reactions were cycled in a DNA Thermal Cycler (Perkin-Elmer) [denaturation at 95° C. for 5 minutes, followed by 30 cycles of amplification (94° C., 45 seconds; 55° C., 30 seconds; 72° C., 3 minutes) and a terminal isothermal extension (72° C., 3 minutes)]. Agarose gel electrophoresis was used to assess the presence and purity of inserts. PCR products are subjected to DNA sequencing reactions using specific primers, BigDye™ Terminator Cycle Sequencing v2.0 Ready Reaction (PE Biosystems), Tris MgCl buffer and water in a thermocycler. Sequencing reactions were incubated at 94° C. for 2 minutes, followed by 25 cycles of 94° C., 30 seconds; 55° C., 20 seconds; and 72° C., 1 minute; and 15 cycles of 94° C., 30 seconds; and 72° C. for 1 minute; and 72° C. for 5 minutes. Reactions were then put on hold at 4° C. until purified through methods well known in the prior art (i.e. column purification or alcohol precipitation). Automated sequencing was carried out with a PE Biosystems ABI Prism 3700 DNA Analyzer.

Sequences were manually edited or edited using Sequencher software (GeneCodes). All edited EST sequences were compared to the non-redundant Genbank/EMBL/DDBJ and dbEST databases using the BLAST algorithm (8). A minimum value of $P=10^{-10}$ and nucleotide sequence identity >95% were required for assignments of putative identities for ESTs matching to known genes or to other ESTs. Construction of a non-redundant list of genes represented in the EST set was done with the help of Unigene, Entrez and PubMed at the National Center for Biotechnology Information (NCBI) site (at www.ncbi.nlm.nih.gov/). Relative gene expression frequency was calculated by dividing the number of EST copies for each gene by the total number of ESTs analyzed. Functional characterization of ESTs with known gene matches was made according to the categories described by Hwang et al., "A Genome-Based Resource for Molecular Cardiovascular Medicine: Toward a Compendium of Cardiovascular Genes."*Circulation* 1997; 96:4146-203).

A total of 13,398 ESTs were obtained from the human fetal cartilage cDNA library. Of these, 5,747 ESTs (41.8%) matched to known gene sequences, 1,855 ESTs (13.4%) matched to other ESTs, and 3,053 (22.0%) matched to mitochondrial, ribosomal, vector and cDNA/hypothetical protein sequences. The 209 ESTs (4.7%) that did not match to any known sequences were designated as novel. The remainder matched to genomic DNA sequences (1,948 ESTs, 13.8%) and repetitive sequences (586 ESTs, 4.3%).

The 13,398 EST sequences in the fetal library were characterized based on the functional classification of the 2,579 unique known genes they represented. The following table sets out the results of this analysis.

TABLE 2

Fetal Cartilage Library

| Putative Function | Percent (%) of Representation in the Library | Number of genes |
|---|---|---|
| Cell division | 7.06 | 182 |
| Cell signaling/communication | 15.01 | 387 |
| Cell structure/motility | 10.90 | 281 |
| Cell/organism defense | 7.60 | 196 |
| Gene/protein expression | 22.22 | 573 |
| Metabolism | 14.89 | 384 |
| Unclassified | 22.33 | 576 |
| Total known/unique genes analyzed | 100.00 | 2,579 |

Example 2

RNA Extraction and Normal Adult cDNA Library Construction

A cDNA library was prepared from normal adult cartilage. ESTs were obtained from the cDNA library and characterized to create one or more gene expression profiles for normal adult chondrocytes.

Large-Scale Sequencing of cDNA Inserts cDNA libraries were constructed into λTripleEx2 vector through a PCR-based method, using SMART (Switching Mechanism At 5' end of RNA Transcript) cDNA Library Construction Kit (Clontech). Phage plaques were randomly picked and positive inserts were identified by PCR. Agarose gel electrophoresis was used to assess the presence and purity of inserts. PCR product was then subjected to automated DNA sequencing with a 5' vector-specific forward primer and sequenced by ABI PRISM 377 DNA sequencer (Perkin Elmer) and ABI PRISM 3700 DNA Analyzer (Applied Biosystems). All generated EST sequences were searched against the nonredundant Genebank/EMBL/DDBL, dbEST and GSS databases. A minimum value of $p=10^{-10}$ and nucleotide sequence identity >90% were required for assignments of putative identities for EST-matching to known genes or other ESTs. Relative EST frequency level was calculated by dividing the EST number matched to that gene into the total number of ESTs obtained from the library.

Sequences were manually edited or edited using Sequencher software (GeneCodes). All edited EST sequences were compared to the non-redundant Genbank/EMBL/DDBJ and dbEST databases using the BLAST algorithm (8). A minimum value of $P=10^{-10}$ and nucleotide sequence identity >95% were required for assignments of putative identities for ESTs matching to known genes or to other ESTs. Construction of a non-redundant list of genes represented in the EST set was done with the help of Unigene, Entrez and PubMed at the National Center for Biotechnology Information (NCBI) site (at www.ncbi.nlm.nih.gov/). Relative gene expression frequency was calculated by dividing the number of EST copies for each gene by the total number of ESTs analyzed. Functional characterization of ESTs with known gene matches was made according to the categories described by Hwang et al (Hwang D M, Dempsey A A, Wang R X, Rezvani M, Barrans J D, Dai K S, et al. A Genome-Based Resource for Molecular Cardiovascular Medicine Toward a Compendium of Cardiovascular Genes. Circulation 1997; 96:4146-203).

A total of 17,151 ESTs were obtained from the normal cartilage cDNA library. Of these, 6,755 ESTs (44.2%) matched to 2,518 known genes. 1.4% (132 ESTs) showed no significant match and were thus designated as novel. Characterization of the 17,151 EST sequences based on functional classification of known/unique genes resulted in the following table:

TABLE 3

Normal Adult Cartilage Library

| Putative function | Percent (%) of representation in the library | Number of genes |
| --- | --- | --- |
| Cell division | 6.13 | 160 |
| Cell signaling/communication | 13.52 | 353 |
| Cell structure/motility | 9.00 | 235 |
| Cell/organism defense | 7.51 | 196 |
| Gene/protein expression | 20.08 | 524 |
| Metabolism | 13.14 | 343 |
| Unclassified | 27.09 | 707 |
| Total known/unique genes analyzed | 100.00 | 2518 |

Example 3

RNA Extraction and cDNA Library Construction from Mild Osteoarthritic Chondrocytes and Severe Osteoarthritic Chondrocytes A cDNA library was prepared from mild osteoarthritic cartilage and severe osteoarthritic cartilage. ESTs were obtained from the cDNA libraries and characterized to create one or more gene expression profiles for mild osteoarthritic chondrocytes and severe osteoarthritic chondrocytes.

Articular cartilage was obtained during either arthroscopic knee surgery or total knee replacement. The cartilage samples were obtained from either areas of very early cartilage degeneration (mild) or from sites of end stage disease (severe). cDNA libraries were constructed as described for normal adult samples (Example 2).

Large-Scale Sequencing of cDNA Inserts cDNA libraries were constructed into λTripleEx2 vector through a PCR-based method, using SMART (Switching Mechanism At 5' end of RNA Transcript) cDNA Library Construction Kit (Clontech). Phage plaques were randomly picked and positive inserts were identified by PCR. Agarose gel electrophoresis was used to assess the presence and purity of inserts. PCR product was then subjected to automated DNA sequencing with a 5' vector-specific forward primer and sequenced by ABI PRISM 377 DNA sequencer (Perkin Elmer) and ABI PRISM 3700 DNA Analyzer (Applied Biosystems). All generated EST sequences were searched against the nonredundant Genebank/EMBL/DDBL, dbEST and GSS databases. A minimum value of $p=10^{-10}$ and nucleotide sequence identity >90% were required for assignments of putative identities for EST-matching to known genes or other ESTs. Relative EST frequency level was calculated by dividing the EST number matched to that gene into the total number of ESTs obtained from the library.

Sequences were manually edited or edited using Sequencher software (GeneCodes). All edited EST sequences were compared to the non-redundant Genbank/EMBL/DDBJ and dbEST databases using the BLAST algorithm (8). A minimum value of $P=10^{-10}$ and nucleotide sequence identity >95% were required for assignments of putative identities for ESTs matching to known genes or to other ESTs.

Construction of a non-redundant list of genes represented in the EST set was done with the help of Unigene, Entrez and PubMed at the National Center for Biotechnology Information (NCBI) site (http://www.ncbi.nlm.nih.gov/). Relative gene expression frequency was calculated by dividing the number of EST copies for each gene by the total number of ESTs analyzed.

Functional characterization of ESTs with known gene matches was made according to the categories described by Hwang et al (Hwang D M, Dempsey A A, Wang R X, Rezvani M, Barrans J D, Dai K S, et al. A Genome-Based Resource for Molecular Cardiovascular Medicine: Toward a Compendium of Cardiovascular Genes. Circulation 1997; 96:4146-203).

A total of 12,651 ESTs and 14,222 ESTs were obtained from the mild and severe OA cDNA libraries (Table 4 and Table 5), respectively. About 43% of mild and 51% of severe OA ESTs matched to known genes in the database. Approximately 2.6% and 1.5% of the ESTs, respectively, resulted in no significant match and were thus designated as novel.

Characterization of the 12,651 EST sequences from the mild OA library and of the 14,222 EST sequences from the severe OA library based on functional characterization of the known genes represented resulted in the following tables:

TABLE 4

Mild OA Cartilage Library

| Putative Function | Percent (%) of Representation in the Library | Number of Genes |
|---|---|---|
| Cell division | 6.39 | 127 |
| Cell signaling/communication | 15.31 | 304 |
| Cell structure/motility | 9.16 | 182 |
| Cell/organism defense | 8.41 | 167 |
| Gene/protein expression | 21.60 | 429 |
| Metabolism | 13.95 | 277 |
| Unclassified | 22.76 | 452 |
| Total known/unique genes analyzed | 100.00 | 1938 |

TABLE 5

Severe OA Cartilage Library

| Putative Function | Percent (%) of Representation in the Library | Number of genes |
|---|---|---|
| Cell division | 6.81 | 157 |
| Cell signaling/communication | 14.14 | 326 |
| Cell structure/motility | 8.50 | 196 |
| Cell/organism defense | 7.98 | 184 |
| Gene/protein expression | 22.94 | 529 |
| Metabolism | 13.53 | 312 |
| Unclassified | 23.94 | 552 |
| Total known/unique genes analyzed | 100.00 | 2256 |

Example 4

Identification of Differentially Expressed Genes in Fetal, Normal Mild Osteoarthritic, and Severe Osteoarthritic Cartilage Genes that are differentially expressed as defined herein between normal, mild, severe and fetal cartilage were identified through relative EST frequency analysis (see Table 13). Of the 5,807 known unique genes identified in Table 13, 405 genes were found to be expressed in all four tissue types. Examples of the possible subanalyses are shown in Tables 27 and 28. Some of these genes with particularly marked differential expression are shown in FIG. 4 and Table 11. The relative frequency of ESTs representing collagens (FIG. 2 and Table 9, and FIG. 3 and Table 10) and selected extracellular matrix proteins (see FIG. 1 and Table 8) were also analyzed.

Example 5

Microarray Construction

A microarray according to the invention was constructed as follows.

PCR products (~40 ul) of cDNA clones from OA cartilage cDNA libraries, in the same 96-well tubes used for amplification, are precipitated with 4 ul (1/10 volume) of 3M sodium acetate (pH 5.2) and 100 ul (2.5 volumes) of ethanol and stored overnight at −20° C. They are then centrifuged at 3,300 rpm at 4° C. for 1 hour. The obtained pellets were washed with 50 ul ice-cold 70% ethanol and centrifuged again for 30 minutes. The pellets are then air-dried and resuspended well in 50% dimethylsulfoxide (DMSO) or 20 ul 3×SSC overnight. The samples are then deposited either singly or in duplicate onto Gamma Amino Propyl Silane (Corning CMT-GAPS or CMT-GAP2, Catalog No. 40003, 40004) or polylysine-coated slides (Sigma Cat. No. P0425) using a robotic GMS 417 or 427 arrayer (Affymetrix, CA). The boundaries of the DNA spots on the microarray are marked with a diamond scriber. The invention provides for arrays where 10-20,000 PCR products are spotted onto a solid support to prepare an array.

The arrays are rehydrated by suspending the slides over a dish of warm particle free $ddH_2O$ for approximately one minute (the spots will swell slightly but not run into each other) and snap-dried on a 70-80° C. inverted heating block for 3 seconds. DNA is then UV crosslinked to the slide (Stratagene, Stratalinker, 65 mJ—set display to "650" which is 650×100 uJ) or baked at 80 C for two to four hours. The arrays are placed in a slide rack. An empty slide chamber is prepared and filled with the following solution: 3.0 grams of succinic anhydride (Aldrich) is dissolved in 189 ml of 1-methyl-2-pyrrolidinone (rapid addition of reagent is crucial); immediately after the last flake of succinic anhydride dissolved, 21.0 ml of 0.2 M sodium borate is mixed in and the solution is poured into the slide chamber. The slide rack is plunged rapidly and evenly in the slide chamber and vigorously shaken up and down for a few seconds, making sure the slides never leave the solution, and then mixed on an orbital shaker for 15-20 minutes. The slide rack is then gently plunged in 95° C. $ddH_2O$ for 2 minutes, followed by plunging five times in 95% ethanol. The slides are then air dried by allowing excess ethanol to drip onto paper towels. The arrays are then stored in the slide box at room temperature until use.

Example 6

Target Nucleic Acid Preparation and Hybridization

Preparation of Fluorescent DNA Probe from mRNA

Fluorescently labeled target nucleic acid samples are prepared for analysis with an array of the invention.

2 μg Oligo-dT primers are annealed to 2 ug of mRNA isolated from a cartilage sample from patient diagnosed with osteoarthritis or suspected of having osteoarthritis in a total volume of 15 ul, by heating to 70° C. for 10 min, and cooled on ice. The mRNA is reverse transcribed by incubating the sample at 42° C. for 1.5-2 hours in a 100 μl volume containing a final concentration of 50 mM Tris-HCl (pH 8.3), 75 mM KCl, 3 mM MgCl2, 25 mM DTT, 25 mM unlabeled dNTPs, 400 units of Superscript II (200 U/uL, Gibco BRL), and 15 mM of Cy3 or Cy5 (Amersham). RNA is then degraded by addition of 15 μl of 0.1N NaOH, and incubation at 70° C. for 10 min. The reaction mixture is neutralized by addition of 15 μl of 0.1N HCL, and the volume is brought to 500 μl with TE (10 mM Tris, 1 mM EDTA), and 20 μg of Cot1 human DNA (Gibco-BRL) is added.

The labeled target nucleic acid sample is purified by centrifugation in a Centricon-30 micro-concentrator (Amicon). If two different target nucleic acid samples (e.g., two samples derived from different patients) are being analyzed and compared by hybridization to the same array, each target nucleic acid sample is labeled with a different fluorescent label (e.g., Cy3 and Cy5) and separately concentrated. The separately concentrated target nucleic acid samples (Cy3 and Cy5 labeled) are combined into a fresh centricon, washed with 500 μl TE, and concentrated again to a volume of less than 70 μL of 10μ g/μl polyA RNA (Sigma, #P9403) and 1 μl of 10 μg/ul tRNA (Gibco-BRL, #15401-011) is added and the volume is adjusted to 9.5 μl with distilled water. For final target nucleic acid preparation 2.1 μl 20×SSC (1.5M NaCl, 150 mM NaCltrate (pH8.0)) and 0.35 μl 10% SDS is added.

Hybridization

Labeled nucleic acid is denatured by heating for 2 min at 100° C., and incubated at 37° C. for 20-30 min before being placed on a nucleic acid array under a 22 mm×22 mm glass cover slip. Hybridization is carried out at 65° C. for 14 to 18 hours in a custom slide chamber with humidity maintained by a small reservoir of 3×SSC. The array is washed by submersion and agitation for 2-5 min in 2×SSC with 0.1% SDS, followed by 1×SSC, and 0.1×SSC. Finally, the array is dried by centrifugation for 2 min in a slide rack in a Beckman GS-6 tabletop centrifuge in Microplus carriers at 650 RPM for 2 min.

Example 7

Signal Detection and Data Generation

Following hybridization of an array with one or more labeled target nucleic acid samples, arrays are scanned immediately using a GMS Scanner 418 and Scanalyzer software (Michael Eisen, Stanford University), followed by Gene-Spring software (Silicon Genetics, CA) analysis. Alternatively, a GMS Scanner 428 and Jaguar software may be used followed by GeneSpring software analysis If one target nucleic acid sample is analyzed, the sample is labeled with one fluorescent dye (e.g., Cy3 or Cy5).

After hybridization to a microarray as described in Example 6, fluorescence intensities at the associated nucleic acid members on the microarray are determined from images taken with a custom confocal microscope equipped with laser excitation sources and interference filters appropriate for the Cy3 or Cy5 fluors.

The presence of Cy3 or Cy5 fluorescent dye on the microarray indicates hybridization of a target nucleic acid and a specific nucleic acid member on the microarray. The intensity of Cy3 or Cy5 fluorescence represents the amount of target nucleic acid which is hybridized to the nucleic acid member on the microarray, and is indicative of the expression level of the specific nucleic acid member sequence in the target sample.

When two target nucleic acid samples are being analyzed and compared (e.g., mild osteoarthritic vs severe osteoarthritic), one target nucleic acid sample (for example, mild osteoarthritic) is labeled with fluorescent dye Cy3, the other target nucleic acid sample (for example, severe osteoarthritis) is labeled with fluorescent dye Cy5.

After hybridization as described in Example 6, fluorescence intensities at the associated nucleic acid members on the microarray are determined from images taken with a custom confocal microscope equipped with laser excitation sources and interference filters appropriate for the Cy3 and Cy5 fluors. Separate scans are taken for each fluor at a resolution of 225 μm$^2$ per pixel and 65,536 gray levels. Normalization between the images is used to adjust for the different efficiencies in labeling and detection with the two different fluors. This is achieved by manual matching of the detection sensitivities to bring a set of internal control genes to nearly equal intensity followed by computational calculation of the residual scalar required for optimal intensity matching for this set of genes.

The presence of Cy3 or Cy5 fluorescent dye on the microarray indicates hybridization of a target nucleic acid and a specific nucleic acid member on the microarray. The intensities of Cy3 or Cy5 fluorescence represent the amount of target nucleic acid which is hybridized to the nucleic acid member on the microarray, and is indicative of the expression level of the specific nucleic acid member sequence in the target sample. If a nucleic acid member on the array shows no color, it indicates that the gene in that element is not expressed in either sample. If a nucleic acid member on the array shows a single color, it indicates that a labeled gene is expressed only in that cell sample. The appearance of both colors indicates that the gene is expressed in both tissue samples. The differences in Cy3 and Cy5 fluorescence intensities, after normalization, are indicative of differences of expression levels of the associated nucleic acid member sequence in the two samples for comparison. Differences in expression intensity between the two samples greater than 1.0 fold are used as an indication of differential gene expression.

The array is scanned in the Cy 3 and Cy5 channels and stored as separate 16-bit TIFF images. The images are incorporated and analysed using Scanalyzer software which includes a gridding process to capture the hybridization intensity data from each spot on the array. The fluorescence intensity and background-subtracted hybridization intensity of each spot is collected and a ratio of measured mean intensities of Cy5 to Cy3 is calculated. A liner regression approach is used for normalization and assumes that a scatter plot of the measured Cy5 versus Cy3 intensities should have a scope of one. The average of the ratios is calculated and used to rescale the data and adjust the slope to one. A post-normalization cutoff of greater than 1.0 fold up- or down-regulation is used to identify differentially expressed genes.

Analysis of a microarray comprising some of the sequences in Table 26, resulted in 36 candidate upregulated genes in the mild OA library that showed a greater than 2-fold median ratio and 47 candidate downregulated genes that showed a less than 0.2-fold median ratio (Tables 21 and 22, respectively,). A total of 38 candidate upregulated genes were also identified in the severe OA library that showed a greater than 2-fold median ratio and 51 candidate downregulated genes that showed a less than 0.2-fold median ratio (Tables 23 and 24, respectively,). According to this embodiment, the microarray was hybridized with a target nucleic acid sample derived from an individual diagnosed with mild osteoarthritis and a target nucleic acid sample derived from an individual diagnosed with severe osteoarthritis. As would be clear to a person skilled in the art, similar analysis can be performed for any of the sequences identified in Table 25, or the sequences identified in Table 14 which correspond to the genes disclosed in Table 13 using the methods disclosed herein. Table 14 lists the names of the EST sequences identified in the four cDNA libraries that represent each of the unique known genes identified in Table 13.

Example 8

Chondrocyte-Specific Gene Microarray and Diagnosis Microarray Construction

A collection of nucleic acid members are spotted on a glass slide as described in Example 5 for the construction of a mild OA diagnosis microarray. A collection of nucleic acid members are spotted on a glass slide as described in Example 5 for the construction of a severe OA diagnosis microarray. A collection of chondrocyte specific nucleic acid members are spotted on a glass slide as described in Example 5 for the construction of a chondrocyte-specific gene microarray. The nucleic acid members spotted onto the microarrays described are selected from those named in Tables 15, 16, 17 and 18. Table 15 lists the names of all of the EST sequences identified from the cDNA library constructed from fetal cartilage tissue according to one embodiment of the invention. Table 16 lists the names of all of the EST sequences identified from the cDNA library constructed from normal cartilage tissue where such tissue is obtained less than 14 hours post-mortem according to one embodiment of the invention. Table 17 lists the names of all of the EST sequences identified from the cDNA library constructed from cartilage of patients with mild osteoarthritis according to one embodiment of the invention. Table 18 lists the names of all of the EST sequences identified from the cDNA library constructed from cartilage of patients with severe osteoarthritis according to one embodiment of the invention.

Table 26 contains all of the EST identified from the four human cartilage cDNA libraries according to one embodiment of the invention. A subset of sequences in this Table was filed as a CD ROM in U.S. provisional application 60/271, 955, filed Feb. 28, 2001 and as a hard copy in U.S. provisional application 60/275,017, filed Mar. 12, 2001. The names of all of the EST sequences in Table 26 are listed in Tables 15, 16, 17 and 18.

Example 9

Diagnosis

Target nucleic acid samples are prepared from cartilage RNA extracts of an individual (as described in Example 6) and hybridized to a microarray comprising a collection of nucleic acid members where at least one member is differentially expressed in cartilage isolated from a patient diagnosed with mild, moderate, marked or severe osteoarthritis, as compared to cartilage isolated from a normal individual as defined herein (as described in Example 6). A hybridization pattern is generated and analyzed as in Example 7. For example, the hybridization of target nucleic acid samples to one or more nucleic acid members on the microarray comprising a collection of nucleic acid members where at least one member is differentially expressed in mild osteoarthritis cartilage as compared to a normal individual is indicative of a mild osteoarthritis of the individual from whom the target nucleic acid sample is derived. The hybridization of target nucleic acid samples to one or more nucleic acid members on the microarray comprising a collection of nucleic acid members differentially expressed in severe osteoarthritis cartilage as compared to the normal individual is indicative of severe osteoarthritis of the individual from whom the target nucleic acid sample is derived.

When diagnosing mild osteoarthritis, the array preferably comprises at least one sequence selected from Table 29, Table 33, Table 40 and Table 44, more preferably a majority of sequences selected from Table 29, Table 33, Table 40 and Table 44 are chosen. More preferably the array comprises at least one sequence selected from Table 33 and Table 44, more preferably the array comprises a majority of sequences selected from Table 33 and Table 44. When diagnosing severe osteoarthritis, the array preferably comprises at least one sequences selected from the sequences of Table 29, Table 37, Table 40 and Table 48. More preferably the array comprises a majority of sequences selected from Table 29, Table 37, Table 40 and Table 48. More preferably, the array comprises at least one sequence selected from the sequences of Table 37 and Table 48, more preferably, the array comprises a majority of sequences selected from the sequences of Table 37 and Table 48.

Example 10

Therapeutic Agent Screening

A candidate therapeutic agent that increases or decreases the expression of one or more nucleic acid sequences that are differentially expressed in a chondrocyte derived from any of the following chondrocyte disease or developmental stages: fetal, mild osteoarthritic, moderate osteoarthritic, marked osteoarthritic and severe osteoarthritic, is screened according to the following method.

Chondrocytes are isolated from a "normal" individual and are incubated in the presence and absence of a candidate agent for varying amounts of time (i.e., 30 min, 1 hr, 5 hr, 24 hr, 48 hr and 96 hrs). When screening for therapeutic genes, a clone of a full gene sequence corresponding to an EST in Table 14 or Table 25 is used to transfect chondrocytes. The transfected chondrocytes are cultured for varying amounts of time (i.e., 1, 2, 3, 5, 7, 10, or 14 days). Following incubation, target nucleic acid samples are prepared from the chondrocytes and hybridized to a nucleic acid probe corresponding to a nucleic acid sequence which is differentially expressed in a chondrocyte derived from at least any two of the following of: fetal, normal, mild osteoarthritic, moderate osteoarthritic and severe osteoarthritic. The nucleic acid probe is labeled, for example with a radioactive label, according to methods well-known in the art and described herein. Hybridization is carried out by northern blot, for example as described in Ausubel et al., supra or Sambrook et al., supra). The differential hybridization, as defined herein, of the probe to the target nucleic acid samples from normal relative to RNA from any one of fetal, mild osteoarthritic, moderate osteoarthritic, marked osteoarthritic and severe osteoarthritic is indicative of the level of expression of RNA corresponding to a differentially expressed chondrocyte specific nucleic acid sequence. A change in the level of expression of the probe sequence as a result of the incubation step in the presence of the candidate agent, is indicative of an agent that increases or decreases the expression of the corresponding chondrocyte specific nucleic acid sequence.

Example 11

Assessing the Integrity of Cartilage RNA Isolated Post-Mortem

The following Baboon cartilage study was preformed to evaluate the quality of freshly isolated RNA and RNA isolated at various times post-mortem.

Nine vials of baboon cartilage were obtained, and stored in liquid nitrogen till use.

Baboon cartilage from each vial was weighed and finely powdered under liquid nitrogen. The sample was then homogenized in TRIzol® reagent (0.1 g/ml TRIzol®) and total RNA was extracted. The quantity of RNA was calculated according to the $OD_{260}$ value. The appearance of two sharp bands on the RNA gel indicated that the RNA was of good quality.

RT-PCR was performed for the gene expression of collagen type II (COL2A 1), B-actin and GAPDH, using 0.1 ug total RNA from each sample.

The RNA gel pattern clearly shows that the RNA was not degraded up to 12 hours post-mortem (Table 6). Therefore stable RNA should be expected from the biopsy sample within 12 hours after death.

TABLE 6

Integrity Of Cartilage RNA Isolated Post-Mortem

| Sample No. | Time Taken | Weight (g) | Total RNA (ug)- Based on OD260 | RNA Gel (non Dil) | Col2A1 | b-actin | GAPDH |
|---|---|---|---|---|---|---|---|
| 1 | Fresh | 0.175 | 8 | OK | ++ | ++ | ++ |
| 2 | 1 hr pm | 0.29 | 9 | OK | ++ | ++ | ++ |
| 3 | 2 hr | 0.29 | 11.36 | OK | ++ | +/− | +/− |
| 4 | 3 hr | 0.25 | 2.8 | OK | ++ | +/− | +/− |
| 5 | 6 hr | 0.53 | 8.0 | OK | ++ | + | +/− |
| 6 | 8 hr | 0.18 | 5.26 | OK | ++ | + | − |
| 7 | 10 hr | 0.38 | 9.35 | OK | ++ | + | +/− |
| 8 | 12 hr | 0.20 | 6.7 | OK | ++ | +/− | − |
| 9 | 24 hr | 0.41 | 9.35 | SMEAR | +/− | − | − |

Collagen type II is abundant and specific to normal articular cartilage. Its mRNA level was comparable among all the samples except #9 (24 hours post-mortem). It should be noted that samples taken earlier will better reflect the natural in vivo state.

Example 12

Expressed Sequence Tags (ESTs) Analysis of Human Chondrocyte Gene Expression in Mild and Severe Osteoarthritic Cartilage Large-scale partial sequencing of cDNA libraries obtained from human fetal cartilage was performed to identify expressed sequence tags (ESTs) corresponding to genes that might play critical roles in OA progression. Large scale sequencing of cDNA libraries from human normal, mild and severe OA cartilage was also performed and a total of over 44,000 ESTs from the three cDNA libraries were analyzed.

Normal cartilage was obtained from the donor program of Department of Orthopaedics and Rehabilitation, University of Miami. OA cartilage samples were obtained from either areas of very early cartilage degeneration (mild) or from sites of end stage disease (severe) during either arthroscopic knee surgery or total knee replacement. Total RNA from cartilage was extracted using TRIzol® reagent (GIBCO). cDNA libraries were constructed into λTriplEx2 vector through a PCR-based method, using SMART (switching Mechanism At 5' end of RNA Transcript) cDNA Library Construction Kit (Clontech) as described above. Phage plaques were randomly picked and positive inserts were identified by PCR. Agarose gel electrophoresis was used to assess the presence and purity of inserts. PCR product was then subjected to automated DNA sequencing with a 5' vector-specific forward primer and sequenced by ABI PRISM 377 DNA sequencer (Perkin Elmer) and ABI PRISM 3700 DNA Analyzer (Applied Biosystems). All generated EST sequences were searched against the nonredundant Genebank/EMBL/DDBL, dbEST and GSS databases. A minimum value of $p=10^{-10}$ and nucleotide sequence identity >90% were required for assignments of putative identities for EST-matching to known genes or other ESTs. Relative EST frequency level was calculated by dividing the EST number matched to that gene into the total number of ESTs obtained from the library.

A total of 17,151 ESTs, 12,651 ESTs and 14,222 ESTs were obtained from normal, mild and severe OA cDNA libraries respectively and used for gene expression profiling. About 44% of the total ESTs from these three cDNA libraries matched to known genes in the database, and about 0.9% of the ESTs (409) resulted in no significant match to known sequences and were thus designated as novel. Nonredundancy analysis of the known gene matches resulted in the identification of 2,518 unique genes in normal, 1,938 in mild and 2,256 in severe OA cartilage. Differentially expressed known genes amongst fetal (22), normal, mild, and severe OA cartilage (23) were identified by examining relative EST frequency levels as shown in Table 13.

Some of the genes with particularly marked differential expression are shown in FIG. 4 and Table 11 provided herewith. Heat shock protein 90 (HSP90) was the gene with the most abundant ESTs matches in mild OA. Its transcript level was low in fetal cartilage. Beta-2 microglobulin (B2M) level was higher in diseased cartilage than normal cartilage, and significantly higher in diseased cartilage than in fetal cartilage. Its EST levels in mild and severe OA were similar. Osteoblast specific factor 2 (OSF-2 pl) was highly expressed in severe OA compared to fetal, mild and normal cartilage. Another differentially expressed gene was megakaryocyte stimulating factor (MSF, also known as superficial zone protein, or proteoglycan 4). It had a significantly higher expression in mild OA than in severe OA.

Figure 3:
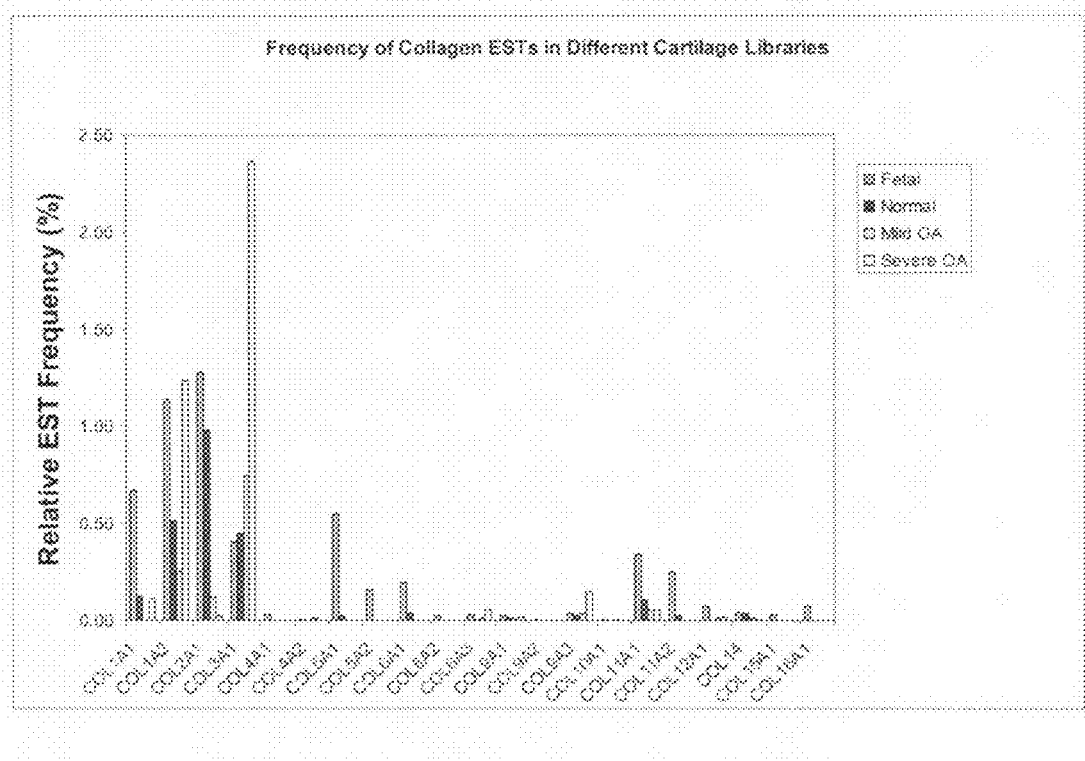
FIG. 3 is a graph according to one embodiment of the invention showing the relative EST levels of specific collagen types among the fetal, normal, mild osteoarthritic and severe osteoarthritic cartilage cDNA libraries.
Figure 4:
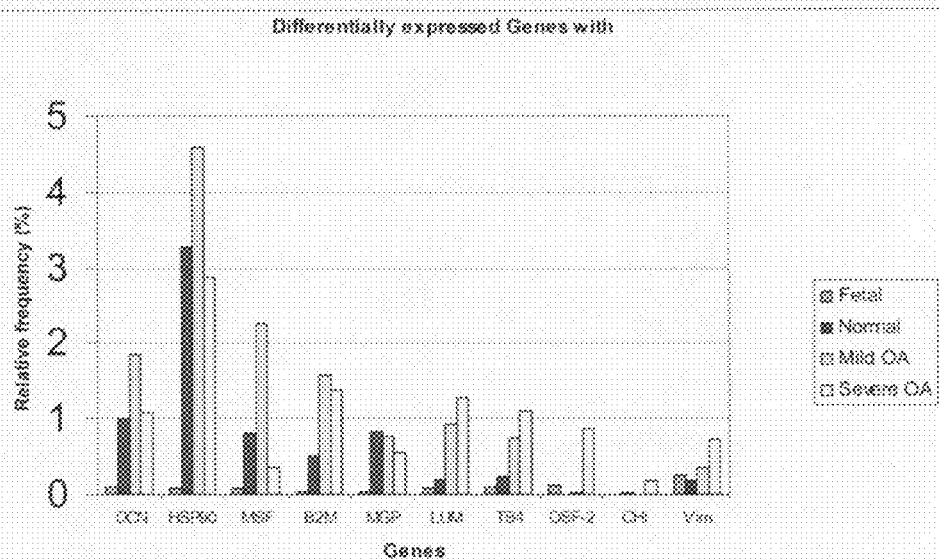
FIG. 4 is a graph according to one embodiment of the invention showing the relative EST frequency level of selected chondrocyte genes among the fetal, normal, mild osteoarthritic and severe osteoarthritic cDNA libraries. Legend: DCN=decorin/chondroitin dermatan sulfate proteoglycan (PG40), HSP90=heatshock protein 90/alpha gene sequence, MSF=megakaryocyte stimulating factor/proteoglycan 4/superficial zone protein, B2M=beta 2 microglobulin, MGP=matrix Gla protein, LUM=lumican, TB4=thymosin beta 4, OSF-2=mRNA for osteoblast specific factor 2, CHI=chitinase, Vim=vimentin.
Figure 5:
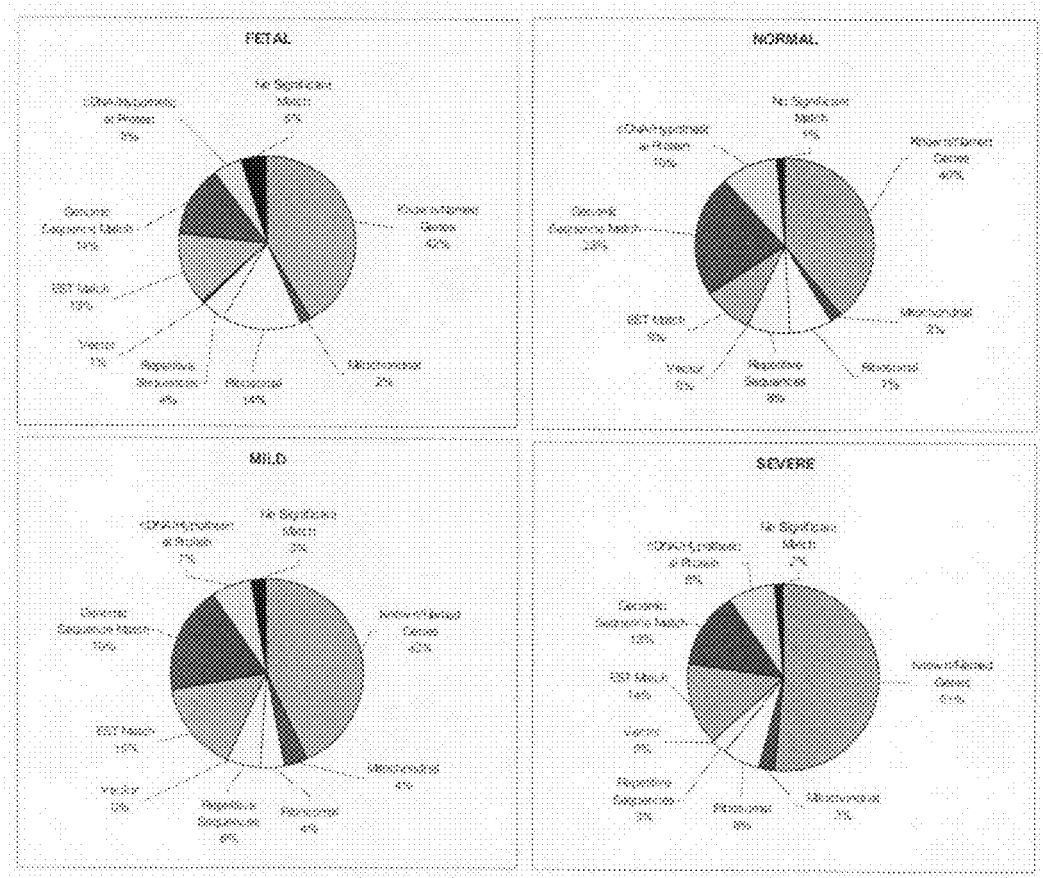
FIG. 5 is a graphical representation of the data presented in Table 12 according to one embodiment of the invention.
Figure 6:
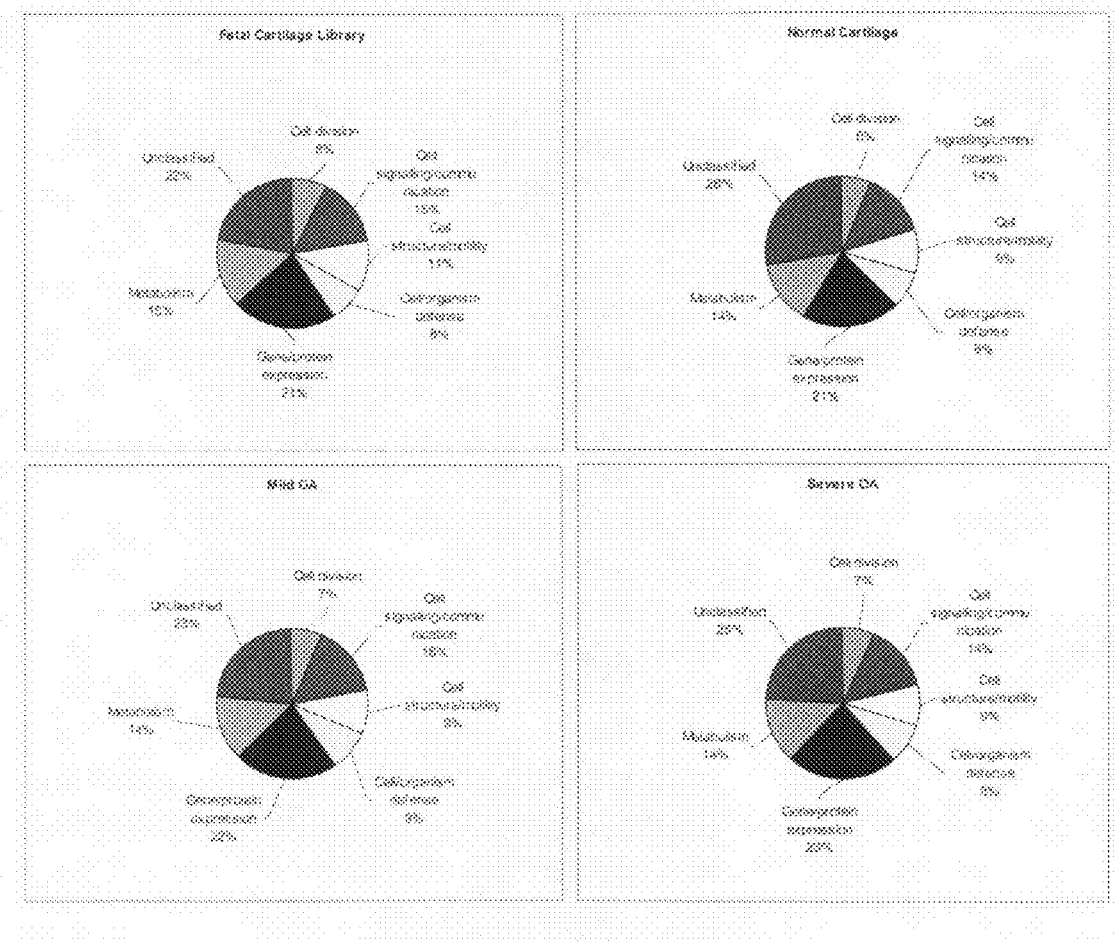
FIG. 6 is a graphical representation of the data presented in Table 19 according to one embodiment of the invention.

The relative frequency of ESTs representing the collagens was also analyzed as shown in FIG. 3 and Table 10.

Figure 2:
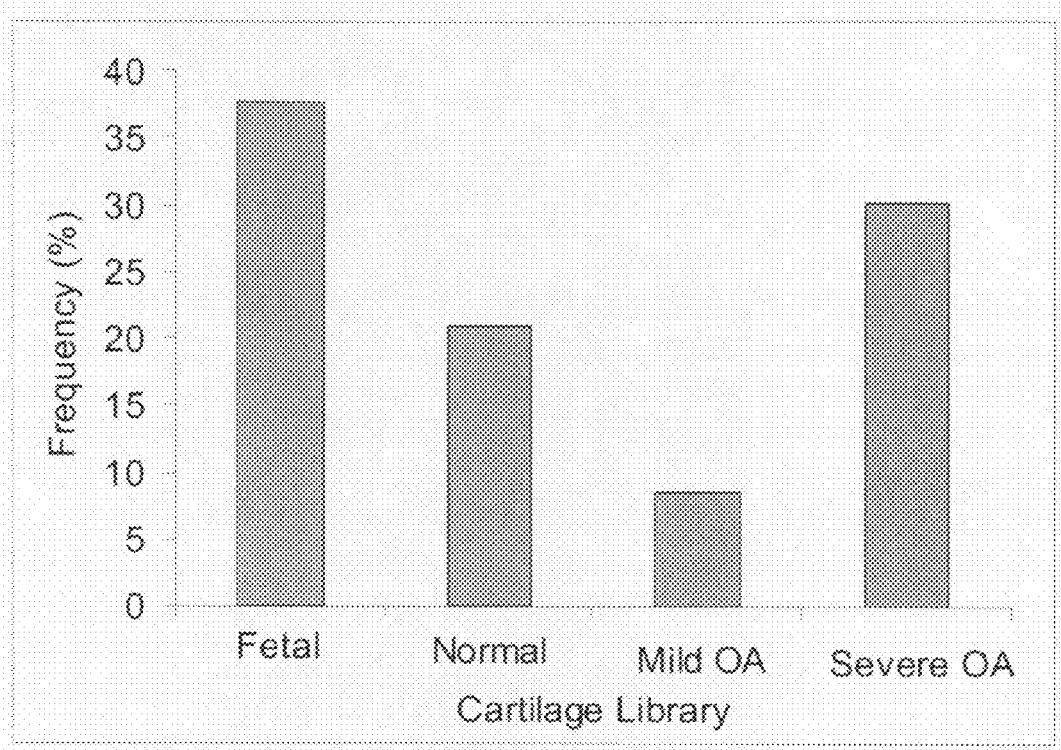
FIG. 2 is a graph according to one embodiment of the invention showing the relative EST frequency level of collagens among the fetal, normal, mild osteoarthritic and severe osteoarthritic cartilage cDNA libraries.

Noncollagenous matrix protein profiles showed higher EST levels of decorin (DCN), fibronectin (FN), lumican (LUM) and matrix Gla protein (MGP) in both mild and severe OA cartilage as shown in FIG. 1 and Table 8, and in FIG. 4 and Table 11 provided herewith.

Example 13

Microarray Analysis of Beta-2 Microglobulin (B2M) Expression in Human Osteoarthritis As discussed above, Beta-2 microglobulin (B2M) had a high EST expression level in mild and severe OA cartilage. B2M is a nonglycosylated polypeptide that is elevated in inflammatory and malignant diseases. It has been shown to induce stromelysin and cyclooxygenase-2 synthesis in human synovial fibroblasts (24, 25).

B2M expression during different stages of osteoarthritis was evaluated. Human OA synovial fluid (SF) was collected from human knee joint by aspiration at arthroscopy or total knee replacement. Normal samples were collected from volunteers with no history of knee injury or arthritis. Organ culture was performed as follows: human severe OA cartilage slices were cultured at one slice/well in a 24-well plate in DMEM (Dulbecco's modified Eagle medium), with 10% FCS, 100 units/ml penicillin and 100 mg/ml streptomycin (DMEM++) at 37° C. in a humidified atmosphere of 5% $CO_2$. Cultured medium (20 ul) was then collected at different time points for B2M testing. B2M levels in synovial fluid and cartilage organ cultured medium were measured using a B2M enzyme immunoassay test kit (ALPCO). Statistical significance was assessed by Student's t-test with P values less than 0.05 being considered significant. Cell culture of chondrocytes from patients with severe OA was performed as follows. Chondrocytes were derived from cartilage from patients with severe OA through collagenase type II digestion. Cells were then seeded at $6.5 \times 10^4$/well ($3.2 \times 10^4$/ml) in a 6-well plate and treated with or without 10 ug/ml B2M (Sigma) for 72 hr. Microarrays containing 5184 chondrocyte-specific cDNA clones were used for gene expression profiling.

Figure 7:
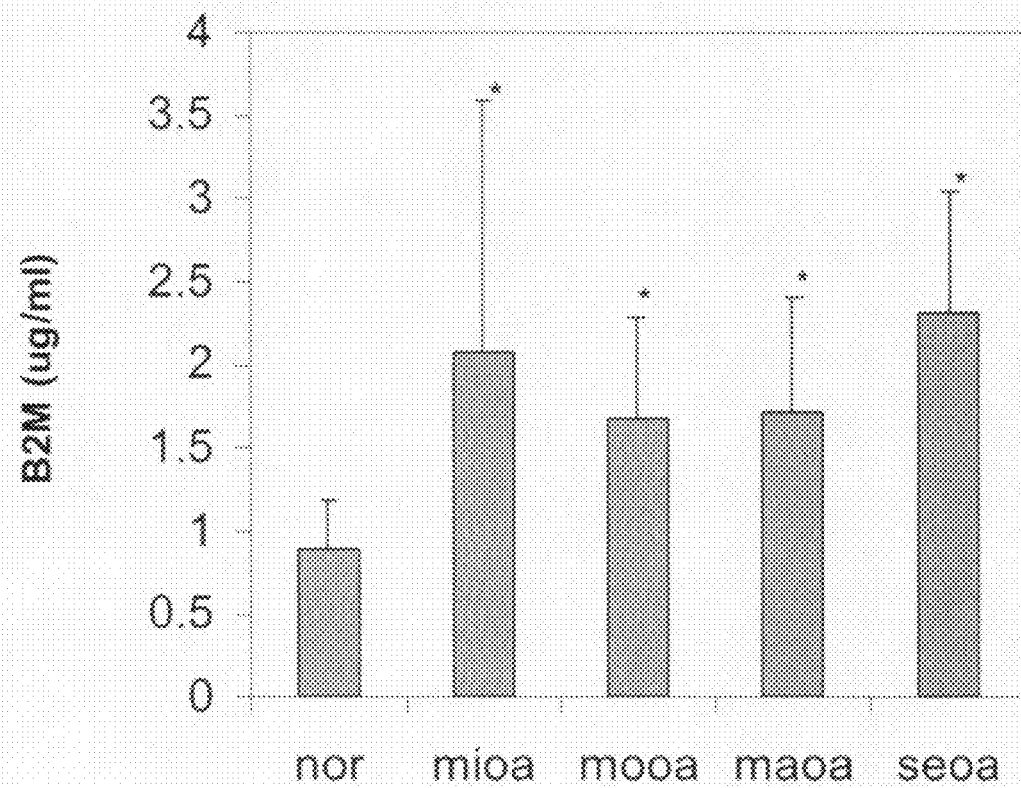
FIG. 7 is a bar graph showing the level of beta-2 microglobulin (B2M) in synovial fluid from normal individuals and patients with different stages of osteoarthritis according to one embodiment of the invention. Legend: nor=normal individual, mioa=patient with mild osteoarthritis, mooa=patient with moderate osteoarthritis, maoa=patient with marked osteoarthritis, seoa=patient with severe osteoarthritis.

The average B2M levels detected in normal (nor), mild (mioa), moderate (mooa), marked (maoa) and severe OA (seoa) synovial fluid are shown in FIG. 7. B2M in osteoarthritis synovial fluid is significantly higher than that in normal. However, no significant difference was found in B2M levels among different osteoarthritis stages.

Figure 8:
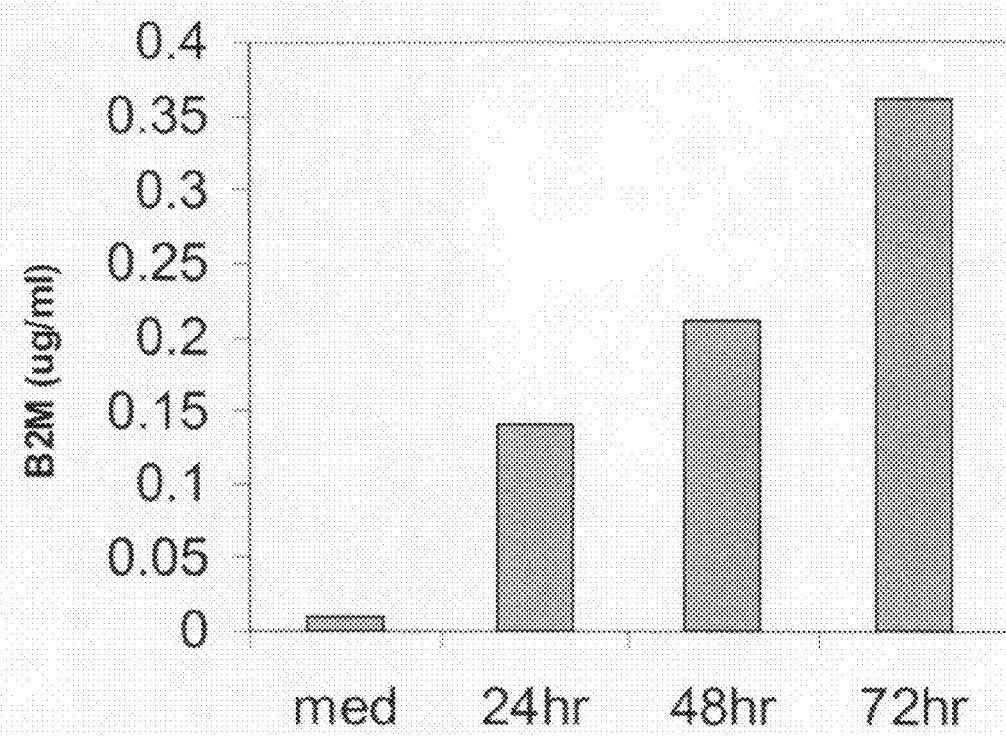
FIG. 8 is a bar graph showing the level of beta 2 microglobulin (B2M) in medium cultured from cartilage from patients with severe osteoarthritis at varying time periods during culturing according to one embodiment of the invention.

To assess if chondrocytes contribute B2M secretion, medium from cultured severe OA cartilage was collected and tested for B2M. FIG. 8 shows the release of B2M is detectable after 24 hour culture and continues to increase during the 72 hour study period. At 72 hours, the accumulation of B2M was about 2.1 ug/g cartilage. Similar results were obtained across three experimental runs, each using cartilage from a different donor.

Figure 9:
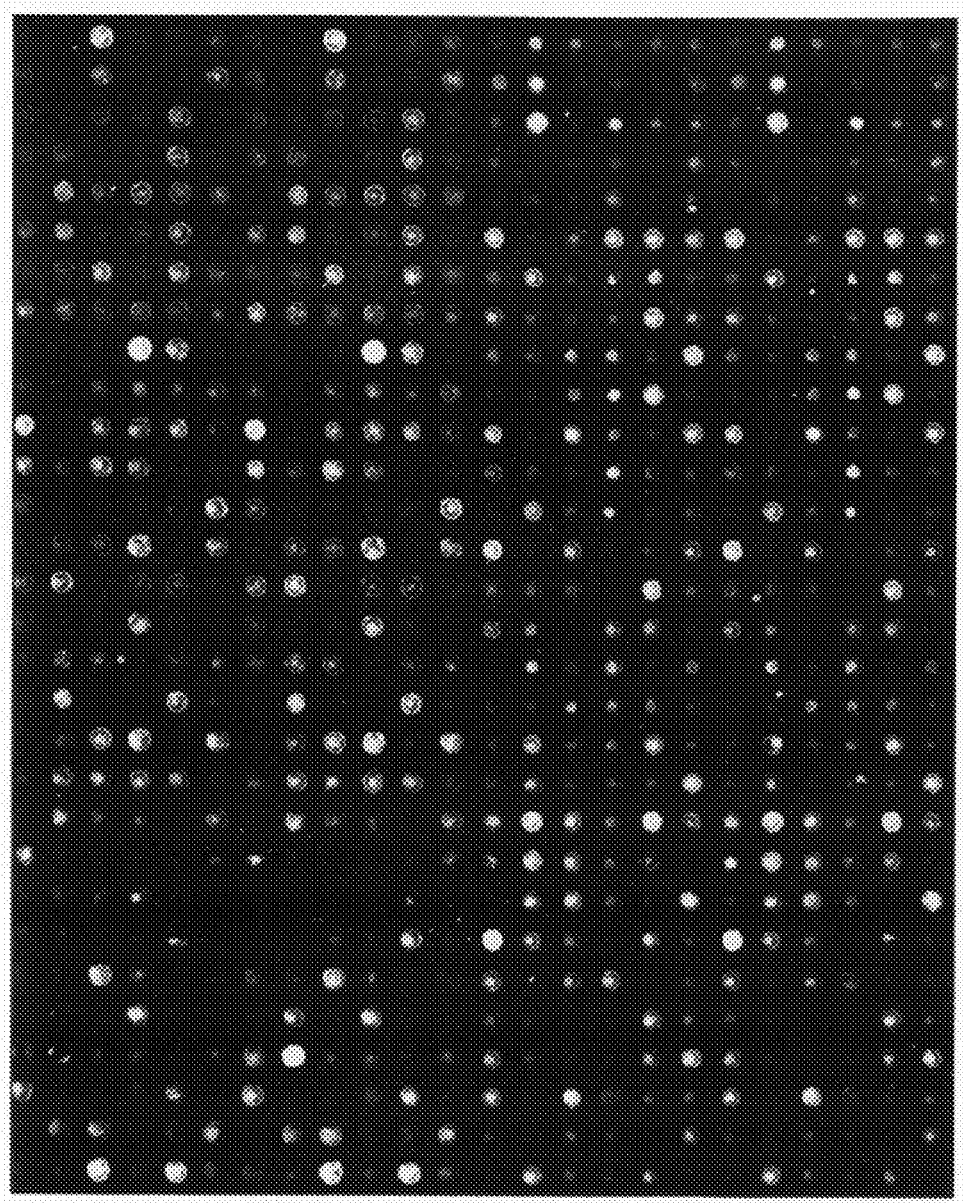
FIG. 9 is a black and white representation of a two-color fluorescent scan according to one embodiment of the invention showing genes preferentially expressed in non-B2M-treated chondrocytes and genes preferentially expressed in B2M-treated chondrocytes. B2M=beta 2 microglobulin.

Genes regulated by B2M were detected through microarray technology as described above. FIG. 9 shows a black and white representation of a two-color fluorescent scan. Cy3 labeling (which would appear as green spots) correspond to genes preferentially expressed in non-B2M treated chondrocytes, while Cy5 labeling (which would appear as reddish spots) represent genes preferentially expressed in B2M treated chondrocytes. Genes expressed at approximately equal levels would appear as yellow spots. The identity of genes was determined by the location of nucleic acid members on the array. Some of the genes that were up or down-regulated at least two-fold by B2M are listed in Table 7.

TABLE 7

Genes Regulated by B2M

| Up-Regulated | Down-Regulated |
|---|---|
| Adrenomedullin | hypothetical protein (KIAA0102) |
| chitinase precursor = YKL-39 | intersectin short form |
| collagen type III, alpha 1 | KARP-1 binding protein 2 (KAB2) |
| manganese superoxide dismutase (SOD-2) | peripheral myelin protein 22 (PMP22) |
| syntaxin 7 | putative GTP binding protein |

Example 14

Hybridization Analysis Identifying up Regulated and Down Regulated Genes in Mild and Severe Osteoarthritis Normal cartilage samples for use as a standard for determining differential expression were provided by the donor program at the Department of Orthopaedics and Rehabilitation, University of Miami. The samples were harvested within 12 hr, from the femoral condyle of patients who had died of a blunt head injury and an acute myocardial infarction.

OA cartilage samples were obtained from knee joints at arthroscopy or total knee replacement (mild n=1, severe n=2). Sequences to be tested were spotted onto a microarray as described herein.

Cartilage samples were ground into a very fine powder, and subjected to RNA isolation using TRIzol® (GIBCO). One microgram total RNA was then amplified one round using RiboAmp™ RNA Amplification Kit (Arcturus) according to the manufacturer's specifications. Two micrograms of the amplified RNA (aRNA) from each sample were used for subsequent microarray hybridization.

For each hybridization, cartilage aRNA was labeled with Cy5 while amplified human universal reference RNA (Stratagene) was parallel labeled with Cy3. The two labels were then mixed and hybridized to the 15K ChondroChip™ for overnight. The next day, the slides were washed and scanned with a GMS 428 Array Scanner (Affymetrix).

Raw scanned images of Cy3 and Cy5 fluorescence were processed using ScanAlyze 2.44 microarray image analysis software. The mean value of net intensity obtained from 72 negative control spots was used as cut-off value. Spots whose net fluorescence intensity value was less than the cut-off value in both Cy3 and Cy5 were excluded. Furthermore, to account for the incomplete hybridization on each spot, only the spots in which at least 50% of pixels (within the defined area of the spot) had fluorescence at least 1.5 times greater than local background in both Cy3 and Cy5 were considered for further analysis. To determine genes that were up- and down-regulated in normal, mild and severe OA cartilage samples, the median ratio for each spot (MART:calculated as the ratio of the median fluorescence from each pixel, minus background, in Cy5 to that in Cy3) from all the hybridizations were submitted to GeneSpring 4.1.5 (Silicon Genetics). A cut-off of two-fold up- or down-regulation relative to normal cartilage samples was used to define differentially expressed genes.

Example 15

Monitoring Drug Efficacy

The drug efficacy was monitored by comparing the expression profile of one or more differentially expressed genes between any two cartilage samples from normal and different stages of osteoarthritic. Cartilage or blood samples were taken from an individual during or after the treatment of a candidate drug as described herein above. As a comparison, cartilage or blood samples were also taken from either the same individual prior to the treatment of the drug or from another individual not treated with the drug. Nucleic acids were extracted from the samples as described and hybridized to an array of the present invention. If one or more nucleic acid members on the array were found to be expressed at different levels in the sample taken from the treated individual compared to the sample taken from the untreated individual, it was indicative of the efficacy of the drug for the treatment of osteoarthritis. Follow-up analysis (e.g., by PCR or Western blot analysis) were then followed to verify the expression differences.

Variations, modifications, and other implementations of what is described herein will occur to those of ordinary skill in the art without departing from the spirit and scope of the invention. The references provided below and referred to herein above are incorporated herein by reference in their entireties.

REFERENCES

1. Zaleske D J. Cartilage and Bone Development. Instr Course Lect 1998; 47:461
2. Buckwalter J A, Mankin H J. Articular Cartilage: Tissue Design and Chondrocyte-Matrix Interactions. Instr Course Lect 1998; 47:477-86.

3. Westacott C I, Sharif M. Cytokines in Osteoarthritis: Mediators or Markers of Joint Destruction? Semin Arthritis Rheum 1996; 25:254-72
4. Adams M D, Kerlavage A R, Fleischmann R D, Fuldner R A, Bult C J, Lee N H, et al. Initial assessment of human gene diversity and expression patterns based upon 83 million nucleotides of cDNA sequence. Nature 1995; 377 Suppl:3-174.
5. Hwang D M, Dempsey A A, Wang R X, Rezvani M, Barrans J D, Dai K S, et al. A Genome-Based Resource for Molecular Cardiovascular Medicine: Toward a Compendium of Cardiovascular Genes. Circulation 1997; 96:4146-203.
6. Mao M, Fu G, Wu J S, Zhang Q H, Zhou J, Kan L X, et al. Identification of genes expressed in human $CD34^+$ hematopoietic stem/progenitor cells by expressed sequence tags and efficient full-length cDNA cloning. Proc Natl Acad Sci 1998; 95:8175-80.
7. Hillier L D, Lennon G, Becker M, Bonaldo M F, Chiapelli B, Chissoe S, et al. Generation and analysis of 280,000 human expressed sequence tags. Genome Res. 1996; 6:807-28.
8. Altschul S F, Gish W, Miller W, Myers E W, Lipman D J. Basic local alignment search tool. J Mol Biol 1990; 215: 403-10.
9. Mundlos S, Zabel B. Developmental Expression of Human Cartilage Matrix Protein. Dev Dyn 1994; 199:241-52.
10. Nakamura S, Kamihagi K, Satakeda H, Katayama M, Pan H, Okamoto H, et al. Enhancement of SPARC (osteonectin) synthesis in arthritic cartilage. Increased levels in synovial fluids from patients with rheumatoid arthritis and regulation by growth factors and cytokines in chondrocyte cultures. Arthritis Rheum 1996; 39:539-51.
11. Eyre D R, The Collagens of Articular Cartilage. Semin Arthritis Rheum 1991; 21 (3 Suppl 2):2-11.
12. Okihana H, Yamada K. Preparation of a cDNA Library and Preliminary Assessment of 1400 Genes from Mouse Growth Cartilage. J Bone Miner Res 1999; 14:304-10.
13. Morrison E H, Ferguson M W J, Bayliss M T, Archer C W. The developmental of articular cartilage: I. The spatial and temporal patterns of collagen types. J Anat 1996; 189:9-22.
14. Treilleux I, Mallein-Gerin F, le Guellec D, Herbage D. Localization of the Expression of Type I, II, III Collagens, and Aggrecan Core Protein Genes in Developing Human Articular Cartilage. Matrix 1992; 12:221-32.
15. Eyre D R, Wu J J, Niyibizi C. The collagens of bone and cartilage: Molecular diversity and supramolecular assembly. In Cohn D V, Glorieux F H, Martin T J, editors. Calcium Regulation and Bone Metabolism. Amsterdam. The Netherlands: Elsevier; 1990. p. 188-94.
16. Birnbacher R. Amann G, Breitschopf H, Lassmann H, Suchanek G, Heinz-Erian P. Cellular localization of insulin-like growth factor II mRNA in the human fetus and the placenta: detection with a digoxigenin-labeled cRNA probe and immunocytochemistry. Pediatr Res 1998; 43:614-20.
17. Wang E, Wang J, Chin E, Zhou J, Bondy C A. Cellular patterns of insulin-like growth factor system gene expression in murine chondrogenesis and osteogenesis. Endocrinology 1995; 136:2741-51.
18. van Kleffens M, Groffen C, Rosato R R, van den Eijnde S M, van Neck J W, Lindenbergh-Kortleve D J, et al. mRNA expression patterns of the IGF system during mouse limb bud development, determined by whole mount in situ hybridization. Mol Cell Endocrinol 1998; 138:151-61.
19. Braulke T, Gotz W, Claussen M. Immunohistochemical localization of insulin-like growth factor binding protein-1, -3, and -4 in human fetal tissues and their analysis in media from fetal tissue explants. Growth Regul 1996; 6:55-65.
20. Kessler E, Takahara K, Biniaminov L, Brusel M, Greenspan D S. Bone Morphogenetic Protein-1: The Type I Procollagen C-Proteinase. Science 1996; 271:360-2.
21. Ausubel et al., John Weley & Sons, Inc., 1997, Current Protocols in Molecular Biology
22. Marshall, K. et al., 2000, 46th Annual Meeting, ORS, paper No. 919.
23. Kumar, S., et al., 2000, 46th Annual Meeting, ORS, paper No. 1031.
24. Marshall K., et al., 2002, 48th Annual meeting, ORS (submitted).
25. Migita K., et al., Biochem Biophys Res Commun 1997, 239:621-625.
26. Migita K., et al., Kidney Int 1999, 55:572-578.

Lengthy table referenced here

US07906278-20110315-T00001

Please refer to the end of the specification for access instructions.

Lengthy table referenced here

US07906278-20110315-T00002

Please refer to the end of the specification for access instructions.

Lengthy table referenced here

US07906278-20110315-T00003

Please refer to the end of the specification for access instructions.

Lengthy table referenced here

US07906278-20110315-T00004

Please refer to the end of the specification for access instructions.

Lengthy table referenced here

US07906278-20110315-T00005

Please refer to the end of the specification for access instructions.

Lengthy table referenced here

US07906278-20110315-T00006

Please refer to the end of the specification for access instructions.

Lengthy table referenced here

US07906278-20110315-T00007

Please refer to the end of the specification for access instructions.

Lengthy table referenced here

US07906278-20110315-T00008

Please refer to the end of the specification for access instructions.

Lengthy table referenced here

US07906278-20110315-T00009

Please refer to the end of the specification for access instructions.

Lengthy table referenced here

US07906278-20110315-T00010

Please refer to the end of the specification for access instructions.

Lengthy table referenced here

US07906278-20110315-T00011

Please refer to the end of the specification for access instructions.

Lengthy table referenced here

US07906278-20110315-T00012

Please refer to the end of the specification for access instructions.

Lengthy table referenced here

US07906278-20110315-T00013

Please refer to the end of the specification for access instructions.

Lengthy table referenced here

US07906278-20110315-T00014

Please refer to the end of the specification for access instructions.

Lengthy table referenced here

US07906278-20110315-T00015

Please refer to the end of the specification for access instructions.

Lengthy table referenced here

US07906278-20110315-T00016

Please refer to the end of the specification for access instructions.

Lengthy table referenced here

US07906278-20110315-T00017

Please refer to the end of the specification for access instructions.

Lengthy table referenced here

US07906278-20110315-T00018

Please refer to the end of the specification for access instructions.

Lengthy table referenced here

US07906278-20110315-T00019

Please refer to the end of the specification for access instructions.

Lengthy table referenced here

US07906278-20110315-T00020

Please refer to the end of the specification for access instructions.

Lengthy table referenced here

US07906278-20110315-T00021

Please refer to the end of the specification for access instructions.

Lengthy table referenced here

US07906278-20110315-T00022

Please refer to the end of the specification for access instructions.

Lengthy table referenced here

US07906278-20110315-T00023

Please refer to the end of the specification for access instructions.

Lengthy table referenced here

US07906278-20110315-T00024

Please refer to the end of the specification for access instructions.

Lengthy table referenced here

US07906278-20110315-T00025

Please refer to the end of the specification for access instructions.

Lengthy table referenced here

US07906278-20110315-T00026

Please refer to the end of the specification for access instructions.

Lengthy table referenced here

US07906278-20110315-T00027

Please refer to the end of the specification for access instructions.

Lengthy table referenced here

US07906278-20110315-T00028

Please refer to the end of the specification for access instructions.

Lengthy table referenced here

US07906278-20110315-T00029

Please refer to the end of the specification for access instructions.

Lengthy table referenced here

US07906278-20110315-T00030

Please refer to the end of the specification for access instructions.

Lengthy table referenced here

US07906278-20110315-T00031

Please refer to the end of the specification for access instructions.

Lengthy table referenced here

US07906278-20110315-T00032

Please refer to the end of the specification for access instructions.

Lengthy table referenced here

US07906278-20110315-T00033

Please refer to the end of the specification for access instructions.

Lengthy table referenced here
US07906278-20110315-T00034

Please refer to the end of the specification for access instructions.

Lengthy table referenced here
US07906278-20110315-T00035

Please refer to the end of the specification for access instructions.

Lengthy table referenced here
US07906278-20110315-T00036

Please refer to the end of the specification for access instructions.

Lengthy table referenced here
US07906278-20110315-T00037

Please refer to the end of the specification for access instructions.

Lengthy table referenced here
US07906278-20110315-T00038

Please refer to the end of the specification for access instructions.

Lengthy table referenced here
US07906278-20110315-T00039

Please refer to the end of the specification for access instructions.

Lengthy table referenced here
US07906278-20110315-T00040

Please refer to the end of the specification for access instructions.

Lengthy table referenced here
US07906278-20110315-T00041

Please refer to the end of the specification for access instructions.

Lengthy table referenced here
US07906278-20110315-T00042

Please refer to the end of the specification for access instructions.

Lengthy table referenced here
US07906278-20110315-T00043

Please refer to the end of the specification for access instructions.

Lengthy table referenced here
US07906278-20110315-T00044

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US07906278B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07906278B2). An electronic copy of the "Sequence Listing" will also be available from the USPTO upon request and payment of the fee set forth in 37 CFR 1.19(b)(3).

What is claimed is:

1. A method of diagnosing osteoarthritis in a human test subject, said method comprising:
    (a) determining a level of RNA encoded by an asporin (ASPN) gene in a cartilage sample of said test subject; and
    (b) comparing said level with a level of RNA encoded by said gene in control cartilage samples, wherein said control samples are samples of normal cartilage;
    whereby an increase of at least two fold in said level of step (a) relative to said level of RNA in said control cartilage samples is indicative of osteoarthritis in said human test subject.

2. A method of determining whether osteoarthritis may be present in a human test subject suspected of having osteoarthritis, said method comprising:
    (a) determining a level of RNA encoded by an asporin (ASPN) gene in a cartilage sample of said test subject; and
    (b) comparing said level with levels of RNA encoded by said gene in control cartilage samples, wherein said control samples are samples of normal cartilage,
    wherein a determination from step (b) that said gene has statistically significant differential expression between said sample of said test subject and said control samples is indicative of osteoarthritis in said test subject, said differential expression consisting of an increase of at least two fold in expression in said sample of said test subject compared to said control samples.

3. The method of claim 2, further comprising the step of isolating RNA from said cartilage sample of said test subject.

4. The method of claim 2, wherein said determining of said levels of RNA encoded by said gene in said cartilage sample of said test subject is effected using an immobilized probe.

* * * * *